US007943365B2

United States Patent
Damude et al.

(10) Patent No.: US 7,943,365 B2
(45) Date of Patent: May 17, 2011

(54) Δ-5 DESATURASES AND THEIR USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 310 days.

(21) Appl. No.: 12/111,237

(22) Filed: Apr. 29, 2008

(65) Prior Publication Data

US 2008/0274521 A1 Nov. 6, 2008

Related U.S. Application Data

(60) Provisional application No. 60/915,733, filed on May 3, 2007.

(51) Int. Cl.
*C12N 1/19* (2006.01)
*C12N 1/15* (2006.01)
*C12N 15/00* (2006.01)

(52) U.S. Cl. ................ 435/254.2; 435/254.11; 435/69.1

(58) Field of Classification Search ........................ None
See application file for complete search history.

(56) References Cited

U.S. PATENT DOCUMENTS

| | | | |
|---|---|---|---|
| 5,972,664 | A | 10/1999 | Knutzon et al. |
| 6,075,183 | A | 6/2000 | Knutzon et al. |
| 6,635,451 | B2 | 10/2003 | Mukerji |
| 7,087,432 | B2 | 8/2006 | Qiu |
| 7,125,672 | B2 | 10/2006 | Picataggio et al. |
| 7,238,482 | B2 | 7/2007 | Picataggio et al. |
| 7,335,476 | B2 | 2/2008 | Picataggio et al. |
| 2005/0136519 | A1 | 6/2005 | Picataggio et al. |
| 2006/0035351 | A1 | 2/2006 | Zhu et al. |
| 2006/0094092 | A1 | 5/2006 | Damude et al. |
| 2006/0110806 | A1 | 5/2006 | Damude et al. |
| 2006/0115881 | A1 | 6/2006 | Damude et al. |
| 2007/0207528 | A1 | 9/2007 | Picataggio et al. |
| 2007/0271632 | A1 | 11/2007 | Damude et al. |
| 2007/0277266 | A1 | 11/2007 | Damude et al. |
| 2007/0292924 | A1 | 12/2007 | Damude et al. |
| 2008/0194685 | A1 | 8/2008 | Damude et al. |
| 2008/0254191 | A1 * | 10/2008 | Damude et al. ............... 426/598 |

FOREIGN PATENT DOCUMENTS

WO WO2007136876 11/2007

OTHER PUBLICATIONS

GENBANK Accession No. AF199596.
GENBANK Accession No. AF226273.
GENBANK Accession No. AF320509.
GENBANK Accession No. AB072976.
GENBANK Accession No. AF489588.
GENBANK Accession No. AJ510244.
GENBANK Accession No. AF419297.
GENBANK Accession No. AF078796.
GENBANK Accession No. AF067654.
GENBANK Accession No. AB022097.
The following applications are commonly owned by DuPont and are reported herein: U.S. Appl. No. 12/111,228, filed Apr. 29, 2008; U.S. Appl. Nos. 60/977,174, filed Oct. 3, 2007, 60/977,177, filed Oct. 3, 2007.
International Search Report and Writtten Opinion for Corresponding PCT/US2008/062196 Mailed Aug. 6, 2008.

* cited by examiner

*Primary Examiner* — Michele K Joike

(57) ABSTRACT

The present invention relates to Δ5 desaturases, which have the ability to convert dihomo-γ-linolenic acid (DGLA; 20:3 ω-6) to arachidonic acid (ARA; 20:4 ω-6) and/or eicosatetraenoic acid (ETA; 20:4 ω-3) to eicosapentaenoic acid (EPA; 20:5 ω-3). Isolated nucleic acid fragments and recombinant constructs comprising such fragments encoding Δ5 desaturases along with a method of making long-chain polyunsaturated fatty acids (PUFAs) using these Δ5 desaturases in oleaginous yeast are disclosed.

12 Claims, 16 Drawing Sheets

Fatty Acid Composition (wt. %)

| Clone | Fatty Acid | 16:0 | 16:1 | 18:0 | 18:1 | LA | GLA | ALA | STA | EDA | SCI | DGLA | ARA |
|---|---|---|---|---|---|---|---|---|---|---|---|---|---|
| pY169-1 | None | 13.0 | 9.1 | 1.9 | 25.0 | 50.5 | 0.0 | 0.2 | 0.0 | 0.2 | 0.0 | 0.0 | 0.0 |
| pY169-2 | None | 12.8 | 9.4 | 1.7 | 23.7 | 51.9 | 0.0 | 0.2 | 0.0 | 0.2 | 0.0 | 0.0 | 0.0 |
| pY169-3 | None | 13.1 | 9.2 | 1.7 | 23.2 | 52.2 | 0.0 | 0.1 | 0.0 | 0.2 | 0.0 | 0.0 | 0.0 |
| pY169-1 | ALA | 11.1 | 7.6 | 1.0 | 32.4 | 27.4 | 0.0 | 19.3 | 0.0 | 0.1 | 0.0 | 0.0 | 0.0 |
| pY169-2 | ALA | 11.4 | 7.0 | 0.9 | 30.4 | 25.1 | 0.0 | 24.2 | 0.0 | 0.1 | 0.0 | 0.0 | 0.0 |
| pY169-3 | ALA | 11.6 | 7.3 | 1.1 | 31.8 | 27.0 | 0.0 | 20.1 | 0.0 | 0.1 | 0.0 | 0.0 | 0.0 |
| pY169-1 | EDA | 13.0 | 8.3 | 1.9 | 26.5 | 47.8 | 0.0 | 0.1 | 0.0 | 1.8 | 0.3 | 0.0 | 0.0 |
| pY169-2 | EDA | 12.8 | 8.4 | 1.9 | 24.4 | 49.4 | 0.0 | 0.1 | 0.0 | 2.4 | 0.4 | 0.0 | 0.0 |
| pY169-3 | EDA | 13.0 | 8.3 | 2.0 | 26.4 | 47.7 | 0.0 | 0.1 | 0.0 | 1.9 | 0.3 | 0.0 | 0.0 |
| pY169-1 | ERA | 12.2 | 7.6 | 1.8 | 25.4 | 43.3 | 0.0 | 5.6 | 0.0 | 0.2 | 0.0 | 0.0 | 0.0 |
| pY169-2 | ERA | 11.5 | 8.0 | 1.3 | 24.5 | 43.7 | 0.0 | 5.9 | 0.0 | 0.2 | 0.0 | 0.0 | 0.0 |
| pY169-3 | ERA | 11.8 | 7.8 | 1.5 | 24.9 | 43.9 | 0.0 | 5.6 | 0.0 | 0.2 | 0.0 | 0.0 | 0.0 |
| pY169-1 | DGLA | 12.7 | 8.3 | 1.2 | 25.3 | 46.6 | 0.4 | 0.1 | 0.0 | 0.2 | 0.0 | 2.3 | 2.7 |
| pY169-2 | DGLA | 13.3 | 7.9 | 1.1 | 25.9 | 44.8 | 0.4 | 0.1 | 0.0 | 0.2 | 0.0 | 3.2 | 3.0 |
| pY169-3 | DGLA | 12.7 | 8.1 | 1.3 | 25.6 | 46.2 | 0.3 | 0.1 | 0.0 | 0.2 | 0.0 | 2.5 | 2.7 |
| pY169-1 | ETA | 11.4 | 8.2 | 1.3 | 37.9 | 27.2 | 0.0 | 0.0 | 0.6 | 0.1 | 0.0 | 0.0 | 0.0 |
| pY169-2 | ETA | 11.6 | 8.0 | 1.1 | 38.5 | 24.6 | 0.0 | 0.0 | 0.6 | 0.1 | 0.0 | 0.0 | 0.0 |
| pY169-3 | ETA | 11.4 | 8.2 | 1.3 | 38.3 | 26.7 | 0.0 | 0.0 | 0.5 | 0.1 | 0.0 | 0.0 | 0.0 |
| pY169-1 | DPA | 13.2 | 7.0 | 1.7 | 24.9 | 47.8 | 0.0 | 0.1 | 0.2 | 0.3 | 0.0 | 0.0 | 0.0 |
| pY169-2 | DPA | 13.0 | 7.3 | 1.5 | 24.7 | 47.2 | 0.0 | 0.1 | 0.2 | 0.3 | 0.0 | 0.0 | 0.0 |
| pY169-3 | DPA | 13.2 | 7.1 | 1.6 | 27.1 | 45.7 | 0.0 | 0.1 | 0.2 | 0.2 | 0.0 | 0.0 | 0.0 |

| Clone | Fatty Acid | ERA | JUP | ETA | EPA | DPA | DHA |
|---|---|---|---|---|---|---|---|
| pY169-1 | None | 0.0 | 0.0 | 0.0 | 0.0 | 0.0 | 0.1 |
| pY169-2 | None | 0.0 | 0.0 | 0.0 | 0.0 | 0.0 | 0.2 |
| pY169-3 | None | 0.0 | 0.0 | 0.0 | 0.0 | 0.0 | 0.2 |
| pY169-1 | ALA | 0.5 | 0.0 | 0.0 | 0.0 | 0.0 | 0.5 |
| pY169-2 | ALA | 0.6 | 0.0 | 0.0 | 0.0 | 0.0 | 0.3 |
| pY169-3 | ALA | 0.5 | 0.0 | 0.0 | 0.0 | 0.0 | 0.4 |
| pY169-1 | EDA | 0.0 | 0.0 | 0.1 | 0.0 | 0.0 | 0.2 |
| pY169-2 | EDA | 0.0 | 0.0 | 0.0 | 0.0 | 0.0 | 0.2 |
| pY169-3 | EDA | 0.0 | 0.0 | 0.0 | 0.0 | 0.0 | 0.2 |
| pY169-1 | ERA | 3.1 | 0.3 | 0.0 | 0.0 | 0.0 | 0.3 |
| pY169-2 | ERA | 4.2 | 0.4 | 0.0 | 0.0 | 0.0 | 0.3 |
| pY169-3 | ERA | 3.7 | 0.3 | 0.0 | 0.0 | 0.0 | 0.2 |
| pY169-1 | DGLA | 0.0 | 0.0 | 0.0 | 0.0 | 0.0 | 0.2 |
| pY169-2 | DGLA | 0.0 | 0.0 | 0.0 | 0.0 | 0.0 | 0.2 |
| pY169-3 | DGLA | 0.0 | 0.0 | 0.0 | 0.0 | 0.0 | 0.2 |
| pY169-1 | ETA | 0.0 | 0.0 | 8.3 | 4.8 | 0.0 | 0.3 |
| pY169-2 | ETA | 0.0 | 0.0 | 10.5 | 4.8 | 0.0 | 0.2 |
| pY169-3 | ETA | 0.0 | 0.0 | 8.5 | 4.7 | 0.0 | 0.1 |
| pY169-1 | DPA | 0.0 | 0.0 | 0.0 | 1.2 | 3.6 | 0.0 |
| pY169-2 | DPA | 0.0 | 0.0 | 0.0 | 1.4 | 4.4 | 0.0 |
| pY169-3 | DPA | 0.0 | 0.0 | 0.0 | 1.2 | 3.6 | 0.0 |

FIG. 7B

Continued from Fig. 7A

| Clone | Fatty Acid | % desat | Average % desat | Ratio n-6/n-3 | Ratio Prod/By-Prod |
|---|---|---|---|---|---|
| pY169-1 | None | 0.0 | 0.0 | | |
| pY169-2 | None | 0.0 | | | |
| pY169-3 | None | 0.0 | | | |
| pY169-1 | ALA | 0.0 | 0.0 | | |
| pY169-2 | ALA | 0.0 | | | |
| pY169-3 | ALA | 0.0 | | | |
| pY169-1 | EDA | 16.2 | 15.4 | 1.7 | |
| pY169-2 | EDA | 15.0 | | | |
| pY169-3 | EDA | 15.1 | | | |
| pY169-1 | ERA | 9.6 | 8.8 | | |
| pY169-2 | ERA | 8.5 | | | |
| pY169-3 | ERA | 8.4 | | | |
| pY169-1 | DGLA | 53.3 | 51.5 | 1.5 | 3.3 |
| pY169-2 | DGLA | 49.0 | | | |
| pY169-3 | DGLA | 52.1 | | | |
| pY169-1 | ETA | 36.9 | 34.7 | | 3.9 |
| pY169-2 | ETA | 31.5 | | | |
| pY169-3 | ETA | 35.6 | | | |
| pY169-1 | DPA | 0.0 | 0.0 | | |
| pY169-2 | DPA | 0.0 | | | |
| pY169-3 | DPA | 0.0 | | | |

FIG. 7C

SEQUENCE LISTING

```
<160> NUMBER OF SEQ ID NOS: 44

<210> SEQ ID NO 1
<211> LENGTH: 1350
<212> TYPE: DNA
<213> ORGANISM: Euglena gracilis
<220> FEATURE:
<221> NAME/KEY: CDS
<222> LOCATION: (1)..(1350)
<223> OTHER INFORMATION: delta-5 desaturase
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: WO2007/136671
<311> PATENT FILING DATE: 2007-05-16
<312> PUBLICATION DATE: 2007-11-29
<313> RELEVANT RESIDUES IN SEQ ID NO: (1)..(1350)
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: US-2007-0292924-A1
<311> PATENT FILING DATE: 2007-05-15
<312> PUBLICATION DATE: 2007-12-20
<313> RELEVANT RESIDUES IN SEQ ID NO: (1)..(1350)

<400> SEQUENCE: 1

atg gct ctc agt ctt acc aca gaa cag ctg tta gaa cgc cct gat ttg       48
Met Ala Leu Ser Leu Thr Thr Glu Gln Leu Leu Glu Arg Pro Asp Leu
1               5                   10                  15

gtt gcg att gat ggc atc ctc tac gac ctt gaa ggg ctt gcc aaa gtt       96
Val Ala Ile Asp Gly Ile Leu Tyr Asp Leu Glu Gly Leu Ala Lys Val
            20                  25                  30

cat cca gga gga gat ttg att ctc gct tct ggt gcc tct gat gcc tcc      144
His Pro Gly Gly Asp Leu Ile Leu Ala Ser Gly Ala Ser Asp Ala Ser
        35                  40                  45

cct ctc ttt tat tca atg cat cca tac gtc aaa ccg gag aat tcc aaa      192
Pro Leu Phe Tyr Ser Met His Pro Tyr Val Lys Pro Glu Asn Ser Lys
    50                  55                  60

ttg ctt caa cag ttc gtc cga ggg aag cat gac cgc acc tcg aag gac      240
Leu Leu Gln Gln Phe Val Arg Gly Lys His Asp Arg Thr Ser Lys Asp
65                  70                  75                  80

att gtc tac acg tat gat tct ccc ttc gca caa gac gtt aag cgg aca      288
Ile Val Tyr Thr Tyr Asp Ser Pro Phe Ala Gln Asp Val Lys Arg Thr
                85                  90                  95

atg cgc gag gtg atg aaa ggg agg aac tgg tac gca acc cct ggc ttc      336
Met Arg Glu Val Met Lys Gly Arg Asn Trp Tyr Ala Thr Pro Gly Phe
            100                 105                 110

tgg ctg cgc acc gtt ggg atc atc gcc gtg acg gcc ttt tgc gag tgg      384
Trp Leu Arg Thr Val Gly Ile Ile Ala Val Thr Ala Phe Cys Glu Trp
        115                 120                 125

cac tgg gct acc acg ggg atg gtg ctg tgg ggc ctg ttg act gga ttc      432
His Trp Ala Thr Thr Gly Met Val Leu Trp Gly Leu Leu Thr Gly Phe
    130                 135                 140

atg cac atg cag atc ggc tta tcc atc cag cat gat gcg tcc cac ggg      480
Met His Met Gln Ile Gly Leu Ser Ile Gln His Asp Ala Ser His Gly
145                 150                 155                 160
```

```
gcc atc agc aag aag cct tgg gtc aac gcc ctc ttc gcc tac ggc att      528
Ala Ile Ser Lys Lys Pro Trp Val Asn Ala Leu Phe Ala Tyr Gly Ile
                165                 170                 175

gac gtc atc gga tcg tcc cgg tgg att tgg ctg cag tcg cac atc atg      576
Asp Val Ile Gly Ser Ser Arg Trp Ile Trp Leu Gln Ser His Ile Met
            180                 185                 190

cgg cac cac acc tac acc aac cag cac ggc ctc gac ctg gat gcg gag      624
Arg His His Thr Tyr Thr Asn Gln His Gly Leu Asp Leu Asp Ala Glu
        195                 200                 205

tcg gca gag ccg ttc ctg gtg ttc cac aac tac ccc gcc gca aac acc      672
Ser Ala Glu Pro Phe Leu Val Phe His Asn Tyr Pro Ala Ala Asn Thr
    210                 215                 220

gcc cga aag tgg ttc cac cgc ttc caa gct tgg tac atg tac ctt gtg      720
Ala Arg Lys Trp Phe His Arg Phe Gln Ala Trp Tyr Met Tyr Leu Val
225                 230                 235                 240

ctg ggg gca tac ggg gta tcg ctg gtg tac aac ccg ctc tac att ttc      768
Leu Gly Ala Tyr Gly Val Ser Leu Val Tyr Asn Pro Leu Tyr Ile Phe
                245                 250                 255

cgg atg cag cac aat gac acc atc cca gag tct gtc acg gcc atg cgg      816
Arg Met Gln His Asn Asp Thr Ile Pro Glu Ser Val Thr Ala Met Arg
            260                 265                 270

gag aat ggc ttt ctg cgg cgc tac cgc aca ctt gca ttc gtg atg cga      864
Glu Asn Gly Phe Leu Arg Arg Tyr Arg Thr Leu Ala Phe Val Met Arg
        275                 280                 285

gct ttc ttc atc ttc cgg acc gca ttc ttg ccc tgg tac ctc act ggg      912
Ala Phe Phe Ile Phe Arg Thr Ala Phe Leu Pro Trp Tyr Leu Thr Gly
    290                 295                 300

acc tca ttg ctg atc acc att cct ctg gtg ccc act gca act ggt gcc      960
Thr Ser Leu Leu Ile Thr Ile Pro Leu Val Pro Thr Ala Thr Gly Ala
305                 310                 315                 320

ttc ttg acg ttc ttc ttc att ttg tcc cac aat ttt gat ggc tcc gaa     1008
Phe Leu Thr Phe Phe Phe Ile Leu Ser His Asn Phe Asp Gly Ser Glu
                325                 330                 335

cgg atc ccc gac aag aac tgc aag gtt aag agc tct gag aag gac gtt     1056
Arg Ile Pro Asp Lys Asn Cys Lys Val Lys Ser Ser Glu Lys Asp Val
            340                 345                 350

gag gct gac caa att gac tgg tat cgg gcg cag gtg gag acg tcc tcc     1104
Glu Ala Asp Gln Ile Asp Trp Tyr Arg Ala Gln Val Glu Thr Ser Ser
        355                 360                 365

aca tac ggt ggc ccc atc gcc atg ttc ttc act ggc ggt ctc aat ttc     1152
Thr Tyr Gly Gly Pro Ile Ala Met Phe Phe Thr Gly Gly Leu Asn Phe
    370                 375                 380

cag atc gag cac cac ctc ttt ccc cgg atg tcg tct tgg cac tac ccc     1200
Gln Ile Glu His His Leu Phe Pro Arg Met Ser Ser Trp His Tyr Pro
385                 390                 395                 400

ttc gtc cag cag gcg gtc cgg gag tgt tgc gaa cgc cat gga gtg cga     1248
Phe Val Gln Gln Ala Val Arg Glu Cys Cys Glu Arg His Gly Val Arg
                405                 410                 415

tat gtt ttc tac cct acc atc gtc ggc aac atc atc tcc acc ctg aag     1296
Tyr Val Phe Tyr Pro Thr Ile Val Gly Asn Ile Ile Ser Thr Leu Lys
            420                 425                 430

tac atg cat aag gtg ggt gtc gtc cac tgc gtg aag gac gca cag gat     1344
Tyr Met His Lys Val Gly Val Val His Cys Val Lys Asp Ala Gln Asp
        435                 440                 445

tcc tga                                                             1350
Ser
```

<210> SEQ ID NO 2
<211> LENGTH: 449
<212> TYPE: PRT

<213> ORGANISM: Euglena gracilis

<400> SEQUENCE: 2

Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
    210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
    290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
        355                 360                 365

Thr Tyr Gly Gly Pro Ile Ala Met Phe Phe Thr Gly Gly Leu Asn Phe
    370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg

-continued

```
                405                 410                 415

Tyr Val Phe Tyr Pro Thr Ile Val Gly Asn Ile Ile Ser Thr Leu Lys
            420                 425                 430

Tyr Met His Lys Val Gly Val Val His Cys Val Lys Asp Ala Gln Asp
        435                 440                 445

Ser


<210> SEQ ID NO 3
<211> LENGTH: 1524
<212> TYPE: DNA
<213> ORGANISM: Euglena anabaena

<400> SEQUENCE: 3

acccagtgta cacctttgac agtcccttcg cccaggatgt caagcagagc gttcgggagg      60

tcatgaaggg gcgcaactgg tacgccacgc ccggcttttg gctgcggacc gcgctgatca     120

tcgcgtgcac tgccataggc gaatggtatt ggatcactac cggggcagtg atgtggggca     180

tcttcaccgg gtacttccac agccagattg ggttggcgat tcaacacgat gcctctcacg     240

gagccatcag caaaaagccc tgggtgaacg cctttttcgc ctacggcatc gacgccattg     300

gatcctcccg ctggatctgg ctgcagtccc acattatgcg ccaccacacc tacaccaacc     360

agcatggcct ggacctggac gctgcctcgg cggagccgtt cattttgttc cactcctacc     420

cggcaacaaa tgcgtcacga aagtggtacc atcggttcca ggcgtggtac atgtacatcg     480

ttttggggat gtatggtgtg tcgatggtgt acaatccgat gtacttgttc acgatgcagc     540

acaacgacac aatcccagag gccacctctc ttagaccagg cagcttttc aaccggcagc      600

gcgccttcgc cgtttccctc cgcctactgt tcatcttccg caacgccttc ctcccctggt     660

acatcgcggg cgcctctccg ctgctcacca tcctgctggt gccaacggtc acaggcatct     720

tcttgacatt tgtttttgtg ctgtcccata actttgaagg cgctgagcgg accccgaaa      780

agaactgcaa ggccaaaagg gccaaggagg ggaaggaggt ccgcgatgta gaggaggacc     840

gggtggactg gtaccgggcg caggccgaga ccgcggcgac ctacgggggc agcgtcggga     900

tgatgctgac cggcggtttg aacctgcaga tcgagcacca cttgttcccc cgcatgtcct     960

cttggcacta ccccttcatc caagatacgg tgcgggaatg ttgcaagcgc catggcgtgc    1020

gctacacata ctacccgacc atcctggaga atataatgtc cacgctccgc tacatgcaga    1080

aggtgggcgt ggcccacaca attcaggatg cccaggaatt ctgagtgagt tcgatccgca    1140

tcgacgtcta ccatttttga tgctgtctat tcctgttttc agtcacctcc agcattctca    1200

tggctggtga ccactgcccc tctaacccat tgtgacacac cgccaaagac tttgcctctt    1260

ttttttccct ttcttttgtc ctcggggtgc tttggccggt gtttactcgc cttgcagtcc    1320

ccgcaaacga ccgacgttta agctccgttg ttgactgggc cgctcgtaaa cccatctgca    1380

ggttgaggct cccatggaga attgtgatgg ctgattagga ggtggcgggg catacatgcc    1440

tcgacactca aagccgggcg gcttctggat tcgaaaacgc aaatgggcgc tttggaaaaa    1500

aaaaaaaaaa aaaaaaaaaa aaaa                                           1524


<210> SEQ ID NO 4
<211> LENGTH: 32
<212> TYPE: DNA
<213> ORGANISM: Artificial Sequence
<220> FEATURE:
<223> OTHER INFORMATION: oligonucleotide YL794

<400> SEQUENCE: 4
```

-continued

```
tttccatggc tctcagtctt accacagaac ag                                   32


<210> SEQ ID NO 5
<211> LENGTH: 27
<212> TYPE: DNA
<213> ORGANISM: Artificial Sequence
<220> FEATURE:
<223> OTHER INFORMATION: oligonucleotide YL797

<400> SEQUENCE: 5

gtacatgtac caagcttgga agcggtg                                         27


<210> SEQ ID NO 6
<211> LENGTH: 27
<212> TYPE: DNA
<213> ORGANISM: Artificial Sequence
<220> FEATURE:
<223> OTHER INFORMATION: oligonucleotide YL796

<400> SEQUENCE: 6

caccgcttcc aagcttggta catgtac                                         27


<210> SEQ ID NO 7
<211> LENGTH: 39
<212> TYPE: DNA
<213> ORGANISM: Artificial Sequence
<220> FEATURE:
<223> OTHER INFORMATION: oligonucleotide YL795

<400> SEQUENCE: 7

tttgcggccg cttaggaatc ctgtgcgtcc ttcacgcag                            39


<210> SEQ ID NO 8
<211> LENGTH: 8165
<212> TYPE: DNA
<213> ORGANISM: Artificial Sequence
<220> FEATURE:
<223> OTHER INFORMATION: plasmid pZUF17

<400> SEQUENCE: 8

gtacgagccg gaagcataaa gtgtaaagcc tggggtgcct aatgagtgag ctaactcaca      60

ttaattgcgt tgcgctcact gcccgctttc cagtcgggaa acctgtcgtg ccagctgcat     120

taatgaatcg gccaacgcgc ggggagaggc ggtttgcgta ttgggcgctc ttccgcttcc     180

tcgctcactg actcgctgcg ctcggtcgtt cggctgcggc gagcggtatc agctcactca     240

aaggcggtaa tacggttatc cacagaatca ggggataacg caggaaagaa catgtgagca     300

aaaggccagc aaaaggccag gaaccgtaaa aaggccgcgt tgctggcgtt tttccatagg     360

ctccgccccc ctgacgagca tcacaaaaat cgacgctcaa gtcagaggtg gcgaaacccg     420

acaggactat aaagatacca ggcgtttccc cctggaagct ccctcgtgcg ctctcctgtt     480

ccgaccctgc cgcttaccgg atacctgtcc gcctttctcc cttcgggaag cgtggcgctt     540

tctcatagct cacgctgtag gtatctcagt tcggtgtagg tcgttcgctc caagctgggc     600

tgtgtgcacg aaccccccgt tcagcccgac cgctgcgcct tatccggtaa ctatcgtctt     660

gagtccaacc cggtaagaca cgacttatcg ccactggcag cagccactgg taacaggatt     720

agcagagcga ggtatgtagg cggtgctaca gagttcttga agtggtggcc taactacggc     780

tacactagaa ggacagtatt tggtatctgc gctctgctga agccagttac cttcggaaaa     840

agagttggta gctcttgatc cggcaaacaa accaccgctg gtagcggtgg tttttttgtt     900

tgcaagcagc agattacgcg cagaaaaaaa ggatctcaag aagatccttt gatcttttct     960
```

-continued

```
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
```

-continued

```
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tcccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg ggcagtgaa    5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
```

-continued gggttggcgg cgtatttgtg tcccaaaaaa cagccccaat tgccccggag aagacggcca 5820
ggccgcctag atgacaaatt caacaactca cagctgactt tctgccattg ccactagggg 5880
ggggcctttt tatatggcca agccaagctc tccacgtcgg ttgggctgca cccaacaata 5940
aatgggtagg gttgcaccaa caaagggatg ggatgggggg tagaagatac gaggataacg 6000
gggctcaatg gcacaaataa gaacgaatac tgccattaag actcgtgatc cagcgactga 6060
caccattgca tcatctaagg gcctcaaaac tacctcggaa ctgctgcgct gatctggaca 6120
ccacagaggt tccgagcact ttaggttgca ccaaatgtcc caccaggtgc aggcagaaaa 6180
cgctggaaca gcgtgtacag tttgtcttaa caaaaagtga gggcgctgag gtcgagcagg 6240
gtggtgtgac ttgttatagc ctttagagct gcgaaagcgc gtatggattt ggctcatcag 6300
gccagattga gggtctgtgg acacatgtca tgttagtgta cttcaatcgc cccctggata 6360
tagccccgac aataggccgt ggcctcattt ttttgccttc cgcacatttc cattgctcgg 6420
tacccacacc ttgcttctcc tgcacttgcc aaccttaata ctggtttaca ttgaccaaca 6480
tcttacaagc ggggggcttg tctagggtat atataaacag tggctctccc aatcggttgc 6540
cagtctcttt tttcctttct ttccccacag attcgaaatc taaactacac atcacacaat 6600
gcctgttact gacgtcctta agcgaaagtc cggtgtcatc gtcggcgacg atgtccgagc 6660
cgtgagtatc cacgacaaga tcagtgtcga gacgacgcgt tttgtgtaat gacacaatcc 6720
gaaagtcgct agcaacacac actctctaca caaactaacc cagctctcca tggctgagga 6780
taagaccaag gtcgagttcc ctaccctgac tgagctgaag cactctatcc ctaacgcttg 6840
ctttgagtcc aacctcggac tctcgctcta ctacactgcc cgagcgatct tcaacgcatc 6900
tgcctctgct gctctgctct acgctgcccg atctactccc ttcattgccg ataacgttct 6960
gctccacgct ctggtttgcg ccacctacat ctacgtgcag ggtgtcatct tctggggttt 7020
ctttaccgtc ggtcacgact gtggtcactc tgccttctcc cgataccact ccgtcaactt 7080
catcattggc tgcatcatgc actctgccat tctgactccc ttcgagtcct ggcgagtgac 7140
ccaccgacac catcacaaga acactggcaa cattgataag gacgagatct tctaccctca 7200
tcggtccgtc aaggacctcc aggacgtgcg acaatgggtc tacaccctcg gaggtgcttg 7260
gtttgtctac ctgaaggtcg gatatgctcc tcgaaccatg tcccactttg acccctggga 7320
ccctctcctg cttcgacgag cctccgctgt catcgtgtcc ctcggagtct gggctgcctt 7380
cttcgctgcc tacgcctacc tcacatactc gctcggcttt gccgtcatgg gcctctacta 7440
ctatgctcct ctctttgtct ttgcttcgtt cctcgtcatt actaccttct tgcatcacaa 7500
cgacgaagct actccctggt acggtgactc ggagtggacc tacgtcaagg gcaacctgag 7560
ctccgtcgac cgatcgtacg gagctttcgt ggacaacctg tctcaccaca ttggcaccca 7620
ccaggtccat cacttgttcc ctatcattcc ccactacaag ctcaacgaag ccaccaagca 7680
ctttgctgcc gcttaccctc acctcgtgag acgtaacgac gagcccatca ttactgcctt 7740
cttcaagacc gctcacctct ttgtcaacta cggagctgtg cccgagactg ctcagatttt 7800
caccctcaaa gagtctgccg ctgcagccaa ggccaagagc gactaagcgg ccgcaagtgt 7860
ggatggggaa gtgagtgccc ggttctgtgt gcacaattgg caatccaaga tggatggatt 7920
caacacaggg atatagcgag ctacgtggtg gtgcgaggat atagcaacgg atatttatgt 7980
ttgacacttg agaatgtacg atacaagcac tgtccaagta caatactaaa catactgtac 8040
atactcatac tcgtacccgg gcaacggttt cacttgagtg cagtggctag tgctcttact 8100
cgtacagtgt gcaatactgc gtatcatagt ctttgatgta tatcgtattc attcatgtta 8160

-continued gttgc 8165

<210> SEQ ID NO 9
<211> LENGTH: 8438
<212> TYPE: DNA
<213> ORGANISM: Artificial Sequence
<220> FEATURE:
<223> OTHER INFORMATION: plasmid pDMW367

<400> SEQUENCE: 9
catggctctc agtcttacca cagaacagct gttagaacgc cctgatttgg ttgcgattga 60
tggcatcctc tacgaccttg aagggcttgc caaagttcat ccaggaggag atttgattct 120
cgcttctggt gcctctgatg cctcccctct cttttattca atgcatccat acgtcaaacc 180
ggagaattcc aaattgcttc aacagttcgt ccgagggaag catgaccgca cctcgaagga 240
cattgtctac acgtatgatt ctcccttcgc acaagacgtt aagcggacaa tgcgcgaggt 300
gatgaaaggg aggaactggt acgcaacccc tggcttctgg ctgcgcaccg ttgggatcat 360
cgccgtgacg gccttttgcg agtggcactg ggctaccacg gggatggtgc tgtggggcct 420
gttgactgga ttcatgcaca tgcagatcgg cttatccatc cagcatgatg cgtcccacgg 480
ggccatcagc aagaagcctt gggtcaacgc cctcttcgcc tacggcattg acgtcatcgg 540
atcgtcccgg tggatttggc tgcagtcgca catcatgcgg caccacacct acaccaacca 600
gcacggcctc gacctggatg cggagtcggc agagccgttc ctggtgttcc acaactaccc 660
cgccgcaaac accgcccgaa agtggttcca ccgcttccaa gcttggtaca tgtaccttgt 720
gctgggggca tacggggtat cgctggtgta caacccgctc tacattttcc ggatgcagca 780
caatgacacc atcccagagt ctgtcacggc catgcgggaa aatggctttc tgcggcgcta 840
ccgcacactt gcattcgtga tgcgagcttt cttcatcttc cggaccgcat tcttgccctg 900
gtacctcact gggacctcat tgctgatcac cattcctctg gtgcccaccg caactggtgc 960
cttcttgacg ttcttcttca ttttgtccca caattttgat ggctccgaac ggatccccga 1020
caagaactgc aaggttaaga gatctgagaa ggacgttgag gctgaccaaa ttgactggta 1080
tcgggcgcag gtggagacgt cctccacata cggtggcccc atcgccatgt tcttcactgg 1140
cggtctcaat ttccagatcg agcaccacct ctttccccgg atgtcgtctt ggcactaccc 1200
cttcgtccag caggcggtcc gggagtgttg cgaacgccat ggagtgcgat atgttttcta 1260
ccctaccatc gtcggcaaca tcatctccac cctgaagtac atgcataagg tgggtgtcgt 1320
ccactgcgtg aaggacgcac aggattccta agcggccgca agtgtggatg gggaagtgag 1380
tgcccggttc tgtgtgcaca attggcaatc caagatggat ggattcaaca cagggatata 1440
gcgagctacg tggtggtgcg aggatatagc aacggatatt tatgtttgac acttgagaat 1500
gtacgataca agcactgtcc aagtacaata ctaaacatac tgtacatact catactcgta 1560
cccgggcaac ggtttcactt gagtgcagtg gctagtgctc ttactcgtac agtgtgcaat 1620
actgcgtatc atagtctttg atgtatatcg tattcattca tgttagttgc gtacgagccg 1680
gaagcataaa gtgtaaagcc tggggtgcct aatgagtgag ctaactcaca ttaattgcgt 1740
tgcgctcact gcccgctttc cagtcgggaa acctgtcgtg ccagctgcat taatgaatcg 1800
gccaacgcgc ggggagaggc ggtttgcgta ttgggcgctc ttccgcttcc tcgctcactg 1860
actcgctgcg ctcggtcgtt cggctgcggc gagcggtatc agctcactca aaggcggtaa 1920
tacggttatc cacagaatca ggggataacg caggaaagaa catgtgagca aaaggccagc 1980
aaaaggccag gaaccgtaaa aaggccgcgt tgctggcgtt tttccatagg ctccgccccc 2040

-continued

```
ctgacgagca tcacaaaaat cgacgctcaa gtcagaggtg gcgaaacccg acaggactat   2100
aaagatacca ggcgtttccc cctggaagct ccctcgtgcg ctctcctgtt ccgaccctgc   2160
cgcttaccgg atacctgtcc gcctttctcc cttcgggaag cgtggcgctt tctcatagct   2220
cacgctgtag gtatctcagt tcggtgtagg tcgttcgctc caagctgggc tgtgtgcacg   2280
aaccccccgt tcagcccgac cgctgcgcct tatccggtaa ctatcgtctt gagtccaacc   2340
cggtaagaca cgacttatcg ccactggcag cagccactgg taacaggatt agcagagcga   2400
ggtatgtagg cggtgctaca gagttcttga agtggtggcc taactacggc tacactagaa   2460
ggacagtatt tggtatctgc gctctgctga agccagttac cttcggaaaa agagttggta   2520
gctcttgatc cggcaaacaa accaccgctg gtagcggtgg tttttttgtt tgcaagcagc   2580
agattacgcg cagaaaaaaa ggatctcaag aagatccttt gatcttttct acggggtctg   2640
acgctcagtg gaacgaaaac tcacgttaag ggattttggt catgagatta tcaaaaagga   2700
tcttcaccta gatcctttta aattaaaaat gaagttttaa atcaatctaa agtatatatg   2760
agtaaacttg gtctgacagt taccaatgct taatcagtga ggcacctatc tcagcgatct   2820
gtctatttcg ttcatccata gttgcctgac tccccgtcgt gtagataact acgatacggg   2880
agggcttacc atctggcccc agtgctgcaa tgataccgcg agacccacgc tcaccggctc   2940
cagatttatc agcaataaac cagccagccg gaagggccga gcgcagaagt ggtcctgcaa   3000
ctttatccgc ctccatccag tctattaatt gttgccggga agctagagta agtagttcgc   3060
cagttaatag tttgcgcaac gttgttgcca ttgctacagg catcgtggtg tcacgctcgt   3120
cgtttggtat ggcttcattc agctccggtt cccaacgatc aaggcgagtt acatgatccc   3180
ccatgttgtg caaaaaagcg gttagctcct tcggtcctcc gatcgttgtc agaagtaagt   3240
tggccgcagt gttatcactc atggttatgg cagcactgca taattctctt actgtcatgc   3300
catccgtaag atgcttttct gtgactggtg agtactcaac caagtcattc tgagaatagt   3360
gtatgcggcg accgagttgc tcttgcccgg cgtcaatacg ggataatacc gcgccacata   3420
gcagaacttt aaaagtgctc atcattggaa aacgttcttc ggggcgaaaa ctctcaagga   3480
tcttaccgct gttgagatcc agttcgatgt aacccactcg tgcacccaac tgatcttcag   3540
catcttttac tttcaccagc gtttctgggt gagcaaaaac aggaaggcaa aatgccgcaa   3600
aaaagggaat aagggcgaca cggaaatgtt gaatactcat actcttcctt tttcaatatt   3660
attgaagcat ttatcagggt tattgtctca tgagcggata catatttgaa tgtatttaga   3720
aaaataaaca aataggggtt ccgcgcacat ttccccgaaa agtgccacct gacgcgccct   3780
gtagcggcgc attaagcgcg gcgggtgtgg tggttacgcg cagcgtgacc gctacacttg   3840
ccagcgccct agcgcccgct cctttcgctt tcttcccttc ctttctcgcc acgttcgccg   3900
gctttccccg tcaagctcta aatcgggggc tccctttagg gttccgattt agtgctttac   3960
ggcacctcga ccccaaaaaa cttgattagg gtgatggttc acgtagtggg ccatcgccct   4020
gatagacggt ttttcgccct ttgacgttgg agtccacgtt ctttaatagt ggactcttgt   4080
tccaaactgg aacaacactc aaccctatct cggtctattc ttttgattta taagggattt   4140
tgccgatttc ggcctattgg ttaaaaaatg agctgattta acaaaaattt aacgcgaatt   4200
ttaacaaaat attaacgctt acaatttcca ttcgccattc aggctgcgca actgttggga   4260
agggcgatcg gtgcgggcct cttcgctatt acgccagctg gcgaaagggg gatgtgctgc   4320
aaggcgatta agttgggtaa cgccagggtt ttcccagtca cgacgttgta aaacgacggc   4380
cagtgaattg taatacgact cactataggg cgaattgggt accgggcccc ccctcgaggt   4440
```

-continued

```
cgatggtgtc gataagcttg atatcgaatt catgtcacac aaaccgatct tcgcctcaag   4500
gaaacctaat tctacatccg agagactgcc gagatccagt ctacactgat taattttcgg   4560
gccaataatt taaaaaaatc gtgttatata atattatatg tattatatat atacatcatg   4620
atgatactga cagtcatgtc ccattgctaa atagacagac tccatctgcc gcctccaact   4680
gatgttctca atatttaagg ggtcatctcg cattgtttaa taataaacag actccatcta   4740
ccgcctccaa atgatgttct caaaatatat tgtatgaact tatttttatt acttagtatt   4800
attagacaac ttacttgctt tatgaaaaac acttcctatt taggaaacaa tttataatgg   4860
cagttcgttc atttaacaat ttatgtagaa taaatgttat aaatgcgtat gggaaatctt   4920
aaatatggat agcataaatg atatctgcat tgcctaattc gaaatcaaca gcaacgaaaa   4980
aaatcccttg tacaacataa atagtcatcg agaaatatca actatcaaag aacagctatt   5040
cacacgttac tattgagatt attattggac gagaatcaca cactcaactg tctttctctc   5100
ttctagaaat acaggtacaa gtatgtacta ttctcattgt tcatacttct agtcatttca   5160
tcccacatat tccttggatt tctctccaat gaatgacatt ctatcttgca aattcaacaa   5220
ttataataag atataccaaa gtagcggtat agtggcaatc aaaaagcttc tctggtgtgc   5280
ttctcgtatt tatttttatt ctaatgatcc attaaaggta tatatttatt tcttgttata   5340
taatcctttt gtttattaca tgggctggat acataaaggt attttgattt aatttttttgc  5400
ttaaattcaa tcccccctcg ttcagtgtca actgtaatgg taggaaatta ccatactttt   5460
gaagaagcaa aaaaaatgaa agaaaaaaaa aatcgtattt ccaggttaga cgttccgcag   5520
aatctagaat gcggtatgcg gtacattgtt cttcgaacgt aaaagttgcg ctccctgaga   5580
tattgtacat ttttgctttt acaagtacaa gtacatcgta caactatgta ctactgttga   5640
tgcatccaca acagtttgtt ttgttttttt ttgttttttt tttttctaat gattcattac   5700
cgctatgtat acctacttgt acttgtagta agccgggtta ttggcgttca attaatcata   5760
gacttatgaa tctgcacggt gtgcgctgcg agttactttt agcttatgca tgctacttgg   5820
gtgtaatatt gggatctgtt cggaaatcaa cggatgctca atcgatttcg acagtaatta   5880
attaagtcat acacaagtca gctttcttcg agcctcatat aagtataagt agttcaacgt   5940
attagcactg tacccagcat ctccgtatcg agaaacacaa caacatgccc cattggacag   6000
atcatgcgga tacacaggtt gtgcagtatc atacatactc gatcagacag gtcgtctgac   6060
catcatacaa gctgaacaag cgctccatac ttgcacgctc tctatataca cagttaaatt   6120
acatatccat agtctaacct ctaacagtta atcttctggt aagcctccca gccagccttc   6180
tggtatcgct tggcctcctc aataggatct cggttctggc cgtacagacc tcggccgaca   6240
attatgatat ccgttccggt agacatgaca tcctcaacag ttcggtactg ctgtccgaga   6300
gcgtctccct tgtcgtcaag acccaccccg ggggtcagaa taagccagtc ctcagagtcg   6360
ccccttaggtc ggttctgggc aatgaagcca accacaaact cggggtcgga tcgggcaagc  6420
tcaatggtct gcttggagta ctcgccagtg gccagagagc ccttgcaaga cagctcggcc   6480
agcatgagca gacctctggc cagcttctcg ttgggagagg ggactaggaa ctccttgtac   6540
tgggagttct cgtagtcaga gacgtcctcc ttcttctgtt cagagacagt ttcctcggca   6600
ccagctcgca ggccagcaat gattccggtt ccgggtacac cgtgggcgtt ggtgatatcg   6660
gaccactcgg cgattcggtg acaccggtac tggtgcttga cagtgttgcc aatatctgcg   6720
aactttctgt cctcgaacag gaagaaaccg tgcttaagag caagttcctt gagggggagc   6780
acagtgccgg cgtaggtgaa gtcgtcaatg atgtcgatat gggttttgat catgcacaca   6840
```

-continued taaggtccga ccttatcggc aagctcaatg agctccttgg tggtggtaac atccagagaa 6900
gcacacaggt tggttttctt ggctgccacg agcttgagca ctcgagcggc aaaggcggac 6960
ttgtggacgt tagctcgagc ttcgtaggag ggcattttgg tggtgaagag gagactgaaa 7020
taaatttagt ctgcagaact ttttatcgga accttatctg gggcagtgaa gtatatgtta 7080
tggtaatagt tacgagttag ttgaacttat agatagactg gactatacgg ctatcggtcc 7140
aaattagaaa gaacgtcaat ggctctctgg gcgtcgcctt tgccgacaaa aatgtgatca 7200
tgatgaaagc cagcaatgac gttgcagctg atattgttgt cggccaaccg cgccgaaaac 7260
gcagctgtca gacccacagc ctccaacgaa gaatgtatcg tcaaagtgat ccaagcacac 7320
tcatagttgg agtcgtactc caaaggcggc aatgacgagt cagacagata ctcgtcgact 7380
caggcgacga cggaattcct gcagcccatc tgcagaattc aggagagacc gggttggcgg 7440
cgtatttgtg tcccaaaaaa cagccccaat tgccccggag aagacggcca ggccgcctag 7500
atgacaaatt caacaactca cagctgactt tctgccattg ccactagggg ggggcctttt 7560
tatatggcca agccaagctc tccacgtcgg ttgggctgca cccaacaata aatgggtagg 7620
gttgcaccaa caaagggatg ggatgggggg tagaagatac gaggataacg gggctcaatg 7680
gcacaaataa gaacgaatac tgccattaag actcgtgatc cagcgactga caccattgca 7740
tcatctaagg gcctcaaaac tacctcggaa ctgctgcgct gatctggaca ccacagaggt 7800
tccgagcact ttaggttgca ccaaatgtcc caccaggtgc aggcagaaaa cgctggaaca 7860
gcgtgtacag tttgtcttaa caaaaagtga gggcgctgag gtcgagcagg gtggtgtgac 7920
ttgttatagc ctttagagct gcgaaagcgc gtatggattt ggctcatcag gccagattga 7980
gggtctgtgg acacatgtca tgttagtgta cttcaatcgc cccctggata tagccccgac 8040
aataggccgt ggcctcattt ttttgccttc cgcacatttc cattgctcgg tacccacacc 8100
ttgcttctcc tgcacttgcc aaccttaata ctggtttaca ttgaccaaca tcttacaagc 8160
ggggggcttg tctagggtat atataaacag tggctctccc aatcggttgc cagtctcttt 8220
tttcctttct ttccccacag attcgaaatc taaactacac atcacacaat gcctgttact 8280
gacgtcctta agcgaaagtc cggtgtcatc gtcggcgacg atgtccgagc cgtgagtatc 8340
cacgacaaga tcagtgtcga gacgacgcgt tttgtgtaat gacacaatcc gaaagtcgct 8400
agcaacacac actctctaca caaactaacc cagctctc 8438

<210> SEQ ID NO 10
<211> LENGTH: 18
<212> TYPE: DNA
<213> ORGANISM: Artificial Sequence
<220> FEATURE:
<223> OTHER INFORMATION: M13F universal primer

<400> SEQUENCE: 10
tgtaaaacga cggccagt 18

<210> SEQ ID NO 11
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 11
gtaatacgac tcactatagg gc 22

<210> SEQ ID NO 12

<211> LENGTH: 1362
<212> TYPE: DNA
<213> ORGANISM: Euglena anabaena
<220> FEATURE:
<221> NAME/KEY: misc_feature
<222> LOCATION: (1)..(1362)
<223> OTHER INFORMATION: delta-5 desaturase

<400> SEQUENCE: 12

```
atggccacca tctctttgac tactgagcaa cttttagaac acccagaact ggttgcaatt     60

gatggggtgt tgtacgatct cttcggactg gcgaaagtgc atccaggtgg caacctcatt    120

gaagccgccg gtgcctccga cggaaccgcc ctgttctact ccatgcaccc tggagtgaag    180

ccagagaatt cgaagctgct gcagcaattt gcccgaggca aacacgaacg aagctcgaag    240

gacccagtgt acacctttga cagtcccttc gcccaggatg tcaagcagag cgttcgggag    300

gtcatgaagg ggcgcaactg gtacgccacg cccggctttt ggctgcggac cgcgctgatc    360

atcgcgtgca ctgccatagg cgaatggtat tggatcacta ccggggcagt gatgtggggc    420

atcttcaccg ggtacttcca cagccagatt gggttggcga ttcaacacga tgcctctcac    480

ggagccatca gcaaaaagcc ctgggtgaac gccttttttcg cctacggcat cgacgccatt    540

ggatcctccc gctggatctg gctgcagtcc cacattatgc gccaccacac ctacaccaac    600

cagcatggcc tggacctgga cgctgcctcg gcggagccgt tcattttgtt ccactcctac    660

ccggcaacaa atgcgtcacg aaagtggtac catcggttcc aggcgtggta catgtacatc    720

gttttgggga tgtatggtgt gtcgatggtg tacaatccga tgtacttgtt cacgatgcag    780

cacaacgaca caatcccaga ggccacctct cttagaccag gcagcttttt caaccggcag    840

cgcgccttcg ccgtttccct ccgcctactg ttcatcttcc gcaacgcctt cctcccctgg    900

tacatcgcgg gcgcctctcc gctgctcacc atcctgctgg tgccaacggt cacaggcatc    960

ttcttgacat ttgtttttgt gctgtcccat aactttgaag gcgctgagcg gaccccccgaa   1020

aagaactgca aggccaaaag ggccaaggag gggaaggagg tccgcgatgt agaggaggac   1080

cgggtggact ggtaccgggc gcaggccgag accgcggcga cctacggggg cagcgtcggg   1140

atgatgctga ccggcggttt gaacctgcag atcgagcacc acttgttccc ccgcatgtcc   1200

tcttggcact accccttcat ccaagatacg gtgcgggaat gttgcaagcg ccatggcgtg   1260

cgctacacat actacccgac catcctggag aatataatgt ccacgctccg ctacatgcag   1320

aaggtgggcg tggcccacac aattcaggat gcccaggaat tc                       1362
```

<210> SEQ ID NO 13
<211> LENGTH: 454
<212> TYPE: PRT
<213> ORGANISM: Euglena anabaena

<400> SEQUENCE: 13

```
Met Ala Thr Ile Ser Leu Thr Thr Glu Gln Leu Leu Glu His Pro Glu
1               5                   10                  15

Leu Val Ala Ile Asp Gly Val Leu Tyr Asp Leu Phe Gly Leu Ala Lys
            20                  25                  30

Val His Pro Gly Gly Asn Leu Ile Glu Ala Ala Gly Ala Ser Asp Gly
        35                  40                  45

Thr Ala Leu Phe Tyr Ser Met His Pro Gly Val Lys Pro Glu Asn Ser
    50                  55                  60

Lys Leu Leu Gln Gln Phe Ala Arg Gly Lys His Glu Arg Ser Ser Lys
65                  70                  75                  80

Asp Pro Val Tyr Thr Phe Asp Ser Pro Phe Ala Gln Asp Val Lys Gln
```

```
                85                  90                  95

Ser Val Arg Glu Val Met Lys Gly Arg Asn Trp Tyr Ala Thr Pro Gly
            100                 105                 110

Phe Trp Leu Arg Thr Ala Leu Ile Ile Ala Cys Thr Ala Ile Gly Glu
        115                 120                 125

Trp Tyr Trp Ile Thr Thr Gly Ala Val Met Trp Gly Ile Phe Thr Gly
    130                 135                 140

Tyr Phe His Ser Gln Ile Gly Leu Ala Ile Gln His Asp Ala Ser His
145                 150                 155                 160

Gly Ala Ile Ser Lys Lys Pro Trp Val Asn Ala Phe Phe Ala Tyr Gly
                165                 170                 175

Ile Asp Ala Ile Gly Ser Ser Arg Trp Ile Trp Leu Gln Ser His Ile
            180                 185                 190

Met Arg His His Thr Tyr Thr Asn Gln His Gly Leu Asp Leu Asp Ala
        195                 200                 205

Ala Ser Ala Glu Pro Phe Ile Leu Phe His Ser Tyr Pro Ala Thr Asn
    210                 215                 220

Ala Ser Arg Lys Trp Tyr His Arg Phe Gln Ala Trp Tyr Met Tyr Ile
225                 230                 235                 240

Val Leu Gly Met Tyr Gly Val Ser Met Val Tyr Asn Pro Met Tyr Leu
                245                 250                 255

Phe Thr Met Gln His Asn Asp Thr Ile Pro Glu Ala Thr Ser Leu Arg
            260                 265                 270

Pro Gly Ser Phe Phe Asn Arg Gln Arg Ala Phe Ala Val Ser Leu Arg
        275                 280                 285

Leu Leu Phe Ile Phe Arg Asn Ala Phe Leu Pro Trp Tyr Ile Ala Gly
    290                 295                 300

Ala Ser Pro Leu Leu Thr Ile Leu Leu Val Pro Thr Val Thr Gly Ile
305                 310                 315                 320

Phe Leu Thr Phe Val Phe Val Leu Ser His Asn Phe Glu Gly Ala Glu
                325                 330                 335

Arg Thr Pro Glu Lys Asn Cys Lys Ala Lys Arg Ala Lys Glu Gly Lys
            340                 345                 350

Glu Val Arg Asp Val Glu Glu Asp Arg Val Asp Trp Tyr Arg Ala Gln
        355                 360                 365

Ala Glu Thr Ala Ala Thr Tyr Gly Gly Ser Val Gly Met Met Leu Thr
    370                 375                 380

Gly Gly Leu Asn Leu Gln Ile Glu His His Leu Phe Pro Arg Met Ser
385                 390                 395                 400

Ser Trp His Tyr Pro Phe Ile Gln Asp Thr Val Arg Glu Cys Cys Lys
                405                 410                 415

Arg His Gly Val Arg Tyr Thr Tyr Tyr Pro Thr Ile Leu Glu Asn Ile
            420                 425                 430

Met Ser Thr Leu Arg Tyr Met Gln Lys Val Gly Val Ala His Thr Ile
        435                 440                 445

Gln Asp Ala Gln Glu Phe
    450
```

<210> SEQ ID NO 14
<211> LENGTH: 4276
<212> TYPE: DNA
<213> ORGANISM: Artificial Sequence
<220> FEATURE:
<223> OTHER INFORMATION: plasmid pLF119

<400> SEQUENCE: 14

```
gtacaaagtt ggcattataa gaaagcattg cttatcaatt tgttgcaacg aacaggtcac     60
tatcagtcaa aataaaatca ttatttgcca tccagctgat atcccctata gtgagtcgta    120
ttacatggtc atagctgttt cctggcagct ctggcccgtg tctcaaaatc tctgatgtta    180
cattgcacaa gataaaaata tatcatcatg ttagaaaaac tcatcgagca tcaaatgaaa    240
ctgcaattta ttcatatcag gattatcaat accatatttt tgaaaaagcc gtttctgtaa    300
tgaaggagaa aactcaccga ggcagttcca taggatggca agatcctggt atcggtctgc    360
gattccgact cgtccaacat caatacaacc tattaatttc ccctcgtcaa aaataaggtt    420
atcaagtgag aaatcaccat gagtgacgac tgaatccggt gagaatggca aaagcttatg    480
catttctttc cagacttgtt caacaggcca gccattacgc tcgtcatcaa aatcactcgc    540
atcaaccaaa ccgttattca ttcgtgattg cgcctgagcg agacgaaata cgcgatcgct    600
gttaaaagga caattacaaa caggaatcga atgcaaccgg cgcaggaaca ctgccagcgc    660
atcaacaata ttttcacctg aatcaggata ttcttctaat acctggaatg ctgttttccc    720
ggggatcgca gtggtgagta accatgcatc atcaggagta cggataaaat gcttgatggt    780
cggaagaggc ataaattccg tcagccagtt tagtctgacc atctcatctg taacatcatt    840
ggcaacgcta cctttgccat gtttcagaaa caactctggc gcatcgggct tcccatacaa    900
tcgatagatt gtcgcacctg attgcccgac attatcgcga gcccatttat acccatataa    960
atcagcatcc atgttggaat ttaatcgcgg cctcgagcaa gacgtttccc gttgaatatg   1020
gctcatagat cttttctcca tcactgatag ggagtggtaa aataactcca tcaatgatag   1080
agtgtcaaca acatgaccaa aatcccttaa cgtgagttac gcgtattaat tgcgttgcgc   1140
tcactgcccg ctttccagtc gggaaacctg tcgtgccagc tgcattaatg aatcggccaa   1200
cgcgcgggga gaggcggttt gcgtattggg cgctcttccg cttcctcgct cactgactcg   1260
ctgcgctcgg tcgttcggct gcggcgagcg gtatcagctc actcaaaggc ggtaatacgg   1320
ttatccacag aatcagggga taacgcagga aagaacatgt gagcaaaagg ccagcaaaag   1380
gccaggaacc gtaaaaaggc cgcgttgctg gcgtttttcc ataggctccg cccccctgac   1440
gagcatcaca aaaatcgacg ctcaagtcag aggtggcgaa acccgacagg actataaaga   1500
taccaggcgt ttccccctgg aagctccctc gtgcgctctc ctgttccgac cctgccgctt   1560
accggatacc tgtccgcctt tctcccttcg ggaagcgtgg cgctttctca atgctcacgc   1620
tgtaggtatc tcagttcggt gtaggtcgtt cgctccaagc tgggctgtgt gcacgaaccc   1680
cccgttcagc ccgaccgctg cgccttatcc ggtaactatc gtcttgagtc caacccggta   1740
agacacgact tatcgccact ggcagcagcc actggtaaca ggattagcag agcgaggtat   1800
gtaggcggtg ctacagagtt cttgaagtgg tggcctaact acggttacac tagaagaaca   1860
gtatttggta tctgcgctct gctgaagcca gttaccttcg gaaaaagagt tggtagctct   1920
tgatccggca aacaaaccac cgctggtagc ggtggttttt ttgtttgcaa gcagcagatt   1980
acgcgcagaa aaaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca aataatgatt   2400
```

-continued ttattttgac tgatagtgac ctgttcgttg caacaaattg atgagcaatg ctttttata 2460 atgccaactt tgtacaaaaa agttggattt tttttcggga tggccaccat ctctttgact 2520
actgagcaac ttttagaaca cccagaactg gttgcaattg atggggtgtt gtacgatctc 2580
ttcggactgg cgaaagtgca tccaggtggc aacctcattg aagccgccgg tgcctccgac 2640
ggaaccgccc tgttctactc catgcaccct ggagtgaagc cagagaattc gaagctgctg 2700
cagcaatttg cccgaggcaa acacgaacga agctcgaagg acccagtgta cacctttgac 2760
agtcccttcg cccaggatgt caagcagagc gttcgggagg tcatgaaggg gcgcaactgg 2820
tacgccacgc ccggcttttg gctgcggacc gcgctgatca tcgcgtgcac tgccataggc 2880
gaatggtatt ggatcactac cggggcagtg atgtggggca tcttcaccgg gtacttccac 2940
agccagattg ggttggcgat tcaacacgat gcctctcacg gagccatcag caaaaagccc 3000
tgggtgaacg cctttttcgc ctacggcatc gacgccattg gatcctcccg ctggatctgg 3060
ctgcagtccc acattatgcg ccaccacacc tacaccaacc agcatggcct ggacctggac 3120
gctgcctcgg cggagccgtt cattttgttc cactcctacc cggcaacaaa tgcgtcacga 3180
aagtggtacc atcggttcca ggcgtggtac atgtacatcg ttttggggat gtatggtgtg 3240
tcgatggtgt acaatccgat gtacttgttc acgatgcagc acaacgacac aatcccagag 3300
gccacctctc ttagaccagg cagctttttc aaccggcagc gcgccttcgc cgtttccctc 3360
cgcctactgt tcatcttccg caacgccttc ctcccctggt acatcgcggg cgcctctccg 3420
ctgctcacca tcctgctggt gccaacggtc acaggcatct tcttgacatt tgtttttgtg 3480
ctgtcccata actttgaagg cgctgagcgg accccgaaa agaactgcaa ggccaaaagg 3540
gccaaggagg ggaaggaggt ccgcgatgta gaggaggacc gggtggactg gtaccgggcg 3600
caggccgaga ccgcggcgac ctacgggggc agcgtcggga tgatgctgac cggcggtttg 3660
aacctgcaga tcgagcacca cttgttcccc cgcatgtcct cttggcacta cccccttcatc 3720 caagatacgg tgcgggaatg ttgcaagcgc catggcgtgc gctacacata ctacccgacc 3780
atcctggaga atataatgtc cacgctccgc tacatgcaga aggtgggcgt ggcccacaca 3840
attcaggatg cccaggaatt ctgagtgagt tcgatccgca tcgacgtcta ccatttttga 3900
tgctgtctat tcctgttttc agtcacctcc agcattctca tggctggtga ccactgcccc 3960
tctaacccat tgtgacacac cgccaaagac tttgcctctt ttttttccct ttcttttgtc 4020
ctcggggtgc tttggccggt gtttactcgc cttgcagtcc ccgcaaacga ccgacgttta 4080
agctccgttg ttgactgggc cgctcgtaaa cccatctgca ggttgaggct cccatggaga 4140
attgtgatgg ctgattagga ggtggcgggg catacatgcc tcgacactca aagccgggcg 4200
gcttctggat tcgaaaacgc aaatgggcgc tttggaaaaa aaaaaaaaaa aaaaaaaaaa 4260
aaaacccaac tttctt 4276

<210> SEQ ID NO 15
<211> LENGTH: 476
<212> TYPE: PRT
<213> ORGANISM: Thalassiosira pseudonana

<400> SEQUENCE: 15

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asn Asp Pro Ala Thr Gln
            20                  25                  30

Ser Val Arg Thr Leu Lys Ser Leu Lys Gly Asn Glu Val Val Ile Asn

-continued

```
        35                  40                  45

Gly Thr Ile Tyr Asp Ile Ala Asp Phe Val His Pro Gly Gly Glu Val
    50                  55                  60

Val Lys Phe Phe Gly Gly Asn Asp Val Thr Ile Gln Tyr Asn Met Ile
65                  70                  75                  80

His Pro Tyr His Thr Gly Lys His Leu Glu Lys Met Lys Ala Val Gly
                85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Phe Tyr Ile Ala Leu
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175

Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
        195                 200                 205

Thr Asp Leu Ile Gly Ser Asn Lys Trp Asn Trp Met Ala Gln His Trp
    210                 215                 220

Thr His His Ala Tyr Thr Asn His Ser Glu Lys Asp Pro Asp Ser Phe
225                 230                 235                 240

Ser Ser Glu Pro Met Phe Ala Phe Asn Asp Tyr Pro Ile Gly His Pro
                245                 250                 255

Lys Arg Lys Trp Trp His Arg Phe Gln Gly Gly Tyr Phe Leu Phe Met
            260                 265                 270

Leu Gly Leu Tyr Trp Leu Pro Thr Val Phe Asn Pro Gln Phe Ile Asp
        275                 280                 285

Leu Arg Gln Arg Gly Ala Gln Tyr Val Gly Ile Gln Met Glu Asn Asp
    290                 295                 300

Phe Ile Val Lys Arg Arg Lys Tyr Ala Val Ala Leu Arg Met Met Tyr
305                 310                 315                 320

Ile Tyr Leu Asn Ile Val Ser Pro Phe Met Asn Asn Gly Leu Ser Trp
                325                 330                 335

Ser Thr Phe Gly Ile Ile Met Leu Met Gly Ile Ser Glu Ser Leu Thr
            340                 345                 350

Leu Ser Val Leu Phe Ser Leu Ser His Asn Phe Ile Asn Ser Asp Arg
        355                 360                 365

Asp Pro Thr Ala Asp Phe Lys Lys Thr Gly Glu Gln Val Cys Trp Phe
    370                 375                 380

Lys Ser Gln Val Glu Thr Ser Ser Thr Tyr Gly Gly Phe Ile Ser Gly
385                 390                 395                 400

Cys Leu Thr Gly Gly Leu Asn Phe Gln Val Glu His His Leu Phe Pro
                405                 410                 415

Arg Met Ser Ser Ala Trp Tyr Pro Tyr Ile Ala Pro Thr Val Arg Glu
            420                 425                 430

Val Cys Lys Lys His Gly Met Ser Tyr Ala Tyr Tyr Pro Trp Ile Gly
        435                 440                 445

Gln Asn Leu Val Ser Thr Phe Lys Tyr Met His Arg Ala Gly Ser Gly
    450                 455                 460
```

```
Ala Asn Trp Glu Leu Lys Pro Leu Ser Gly Ser Ala
465                 470                 475


<210> SEQ ID NO 16
<211> LENGTH: 469
<212> TYPE: PRT
<213> ORGANISM: Phaeodactylum tricornutum

<400> SEQUENCE: 16

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365
```

```
Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465


<210> SEQ ID NO 17
<211> LENGTH: 9472
<212> TYPE: DNA
<213> ORGANISM: Artificial Sequence
<220> FEATURE:
<223> OTHER INFORMATION: plasmid pDMW263

<400> SEQUENCE: 17

catggcatgg atggtacgtc ctgtagaaac cccaacccgt gaaatcaaaa aactcgacgg     60

cctgtgggca ttcagtctgg atcgcgaaaa ctgtggaatt gatcagcgtt ggtgggaaag    120

cgcgttacaa gaaagccggg caattgctgt gccaggcagt tttaacgatc agttcgccga    180

tgcagatatt cgtaattatg cgggcaacgt ctggtatcag cgcgaagtct ttataccgaa    240

aggttgggca ggccagcgta tcgtgctgcg tttcgatgcg gtcactcatt acggcaaagt    300

gtgggtcaat aatcaggaag tgatggagca tcagggcggc tatacgccat ttgaagccga    360

tgtcacgccg tatgttattg ccgggaaaag tgtacgtatc accgtttgtg tgaacaacga    420

actgaactgg cagactatcc cgccgggaat ggtgattacc gacgaaaacg gcaagaaaaa    480

gcagtcttac ttccatgatt tctttaacta tgccgggatc catcgcagcg taatgctcta    540

caccacgccg aacacctggg tggacgatat caccgtggtg acgcatgtcg cgcaagactg    600

taaccacgcg tctgttgact ggcaggtggt ggccaatggt gatgtcagcg ttgaactgcg    660

tgatgcggat caacaggtgg ttgcaactgg acaaggcact agcgggactt tgcaagtggt    720

gaatccgcac ctctggcaac cgggtgaagg ttatctctat gaactgtgcg tcacagccaa    780

aagccagaca gagtgtgata tctacccgct tcgcgtcggc atccggtcag tggcagtgaa    840

gggcgaacag ttcctgatta accacaaacc gttctacttt actggctttg gtcgtcatga    900

agatgcggac ttacgtggca aaggattcga taacgtgctg atggtgcacg accacgcatt    960

aatggactgg attggggcca actcctaccg tacctcgcat tacccttacg ctgaagagat   1020

gctcgactgg gcagatgaac atggcatcgt ggtgattgat gaaactgctg ctgtcggctt   1080

taacctctct ttaggcattg gtttcgaagc gggcaacaag ccgaaagaac tgtacagcga   1140

agaggcagtc aacggggaaa ctcagcaagc gcacttacag gcgattaaag agctgatagc   1200

gcgtgacaaa aaccacccaa gcgtggtgat gtggagtatt gccaacgaac cggatacccg   1260

tccgcaagtg cacgggaata tttcgccact ggcggaagca acgcgtaaac tcgacccgac   1320

gcgtccgatc acctgcgtca atgtaatgtt ctgcgacgct cacaccgata ccatcagcga   1380

tctctttgat gtgctgtgcc tgaaccgtta ttacggatgg tatgtccaaa gcggcgattt   1440

ggaaacggca gagaaggtac tggaaaaaga acttctggcc tggcaggaga aactgcatca   1500
```

gccgattatc atcaccgaat acggcgtgga tacgttagcc gggctgcact caatgtacac 1560
cgacatgtgg agtgaagagt atcagtgtgc atggctggat atgtatcacc gcgtctttga 1620
tcgcgtcagc gccgtcgtcg gtgaacaggt atggaatttc gccgattttg cgacctcgca 1680
aggcatattg cgcgttggcg gtaacaagaa agggatcttc actcgcgacc gcaaaccgaa 1740
gtcggcggct tttctgctgc aaaaacgctg gactggcatg aacttcggtg aaaaaccgca 1800
gcagggaggc aaacaatgat taattaacta gagcggccgc caccgcggcc cgagattccg 1860
gcctcttcgg ccgccaagcg acccgggtgg acgtctagag gtacctagca attaacagat 1920
agtttgccgg tgataattct cttaacctcc cacactcctt tgacataacg atttatgtaa 1980
cgaaactgaa atttgaccag atattgtgtc cgcggtggag ctccagcttt tgttcccttt 2040
agtgagggtt aatttcgagc ttggcgtaat catggtcata gctgtttcct gtgtgaaatt 2100
gttatccgct cacaattcca cacaacatac gagccggaag cataaagtgt aaagcctggg 2160
gtgcctaatg agtgagctaa ctcacattaa ttgcgttgcg ctcactgccc gctttccagt 2220
cgggaaacct gtcgtgccag ctgcattaat gaatcggcca acgcgcgggg agaggcggtt 2280
tgcgtattgg gcgctcttcc gcttcctcgc tcactgactc gctgcgctcg gtcgttcggc 2340
tgcggcgagc ggtatcagct cactcaaagg cggtaatacg gttatccaca gaatcagggg 2400
ataacgcagg aaagaacatg tgagcaaaag gccagcaaaa ggccaggaac cgtaaaaagg 2460
ccgcgttgct ggcgtttttc cataggctcc gcccccctga cgagcatcac aaaaatcgac 2520
gctcaagtca gaggtggcga aacccgacag gactataaag ataccaggcg tttccccctg 2580
gaagctccct cgtgcgctct cctgttccga ccctgccgct taccggatac ctgtccgcct 2640
ttctcccttc gggaagcgtg gcgctttctc atagctcacg ctgtaggtat ctcagttcgg 2700
tgtaggtcgt tcgctccaag ctgggctgtg tgcacgaacc ccccgttcag cccgaccgct 2760
gcgccttatc cggtaactat cgtcttgagt ccaacccggt aagacacgac ttatcgccac 2820
tggcagcagc cactggtaac aggattagca gagcgaggta tgtaggcggt gctacagagt 2880
tcttgaagtg gtggcctaac tacggctaca ctagaaggac agtatttggt atctgcgctc 2940
tgctgaagcc agttaccttc ggaaaaagag ttggtagctc ttgatccggc aaacaaacca 3000
ccgctggtag cggtggtttt tttgtttgca agcagcagat tacgcgcaga aaaaaaggat 3060
ctcaagaaga tcctttgatc ttttctacgg ggtctgacgc tcagtggaac gaaaactcac 3120
gttaagggat tttggtcatg agattatcaa aaaggatctt cacctagatc cttttaaatt 3180
aaaaatgaag ttttaaatca atctaaagta tatatgagta aacttggtct gacagttacc 3240
aatgcttaat cagtgaggca cctatctcag cgatctgtct atttcgttca tccatagttg 3300
cctgactccc cgtcgtgtag ataactacga tacgggaggg cttaccatct ggccccagtg 3360
ctgcaatgat accgcgagac ccacgctcac cggctccaga tttatcagca ataaaccagc 3420
cagccggaag ggccgagcgc agaagtggtc ctgcaacttt atccgcctcc atccagtcta 3480
ttaattgttg ccgggaagct agagtaagta gttcgccagt taatagtttg cgcaacgttg 3540
ttgccattgc tacaggcatc gtggtgtcac gctcgtcgtt tggtatggct tcattcagct 3600
ccggttccca acgatcaagg cgagttacat gatcccccat gttgtgcaaa aaagcggtta 3660
gctccttcgg tcctccgatc gttgtcagaa gtaagttggc cgcagtgtta tcactcatgg 3720
ttatggcagc actgcataat tctcttactg tcatgccatc cgtaagatgc ttttctgtga 3780
ctggtgagta ctcaaccaag tcattctgag aatagtgtat gcggcgaccg agttgctctt 3840
gcccggcgtc aatacgggat aataccgcgc cacatagcag aactttaaaa gtgctcatca 3900

-continued

```
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata gacggttttt cgccctttga   4500
cgttggagtc cacgttcttt aatagtggac tcttgttcca aactggaaca acactcaacc   4560
ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
atagggcgaa ttgggtaccg ggccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga aatcttaaat atggatagca taaatgatat   5400
ctgcattgcc taattcgaaa tcaacagcaa cgaaaaaaat cccttgtaca acataaatag   5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat ccttttgttt attacatggg   5820
ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacattttt gcttttacaa   6060
gtacaagtac atcgtacaac tatgtactac tgttgatgca tccacaacag tttgttttgt   6120
tttttttgt ttttttttt tctaatgatt cattaccgct atgtatacct acttgtactt   6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
```

-continued

```
aatcaacgga tgctcaaccg atttcgacag taataatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
taaaacaaat gaaaagaaat acagttcttt gtatcatttg taacaattac cctgtacaaa   6600
ctaaggtatt gaaatcccac aatattccca aagtccaccc ctttccaaat tgtcatgcct   6660
acaactcata taccaagcac taacctacca aacaccacta aaaccccaca aaatatatct   6720
taccgaatat acagtaacaa gctaccacca cactcgttgg gtgcagtcgc cagcttaaag   6780
atatctatcc acatcagcca caactccctt cctttaataa accgactaca cccttggcta   6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg cccttttat agagtcttat    7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
ttgagcatca tggcggcaga cagaatggtg gcaatggggt tgaccttctg cttgccgaga   7320
tcgggggcag atccgtgaca gggctcgtac agaccgaacg cctcgttggt gtcgggcaga   7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg   7800
atgaagtcgg tgccctcaac gtttcggatg ggggagagat cggcgagctt gggcgacagc   7860
agctggcagg gtcgcaggtt ggcgtacagg ttcaggtcct ttcgcagctt gaggagaccc   7920
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaacagt   8520
gtacgcagat ctactataga ggaacattta aattgccccg gagaagacgg ccaggccgcc   8580
tagatgacaa attcaacaac tcacagctga ctttctgcca ttgccactag gggggggcct   8640
ttttatatgg ccaagccaag ctctccacgt cggttgggct gcacccaaca ataaatgggt   8700
```

```
agggttgcac caacaaaggg atgggatggg gggtagaaga tacgaggata acggggctca   8760
atggcacaaa taagaacgaa tactgccatt aagactcgtg atccagcgac tgacaccatt   8820
gcatcatcta agggcctcaa aactacctcg gaactgctgc gctgatctgg acaccacaga   8880
ggttccgagc actttaggtt gcaccaaatg tcccaccagg tgcaggcaga aaacgctgga   8940
acagcgtgta cagtttgtct taacaaaaag tgagggcgct gaggtcgagc agggtggtgt   9000
gacttgttat agcctttaga gctgcgaaag cgcgtatgga tttggctcat caggccagat   9060
tgagggtctg tggacacatg tcatgttagt gtacttcaat cgccccctgg atatagcccc   9120
gacaataggc cgtggcctca ttttttgcc ttccgcacat ttccattgct cgatacccac   9180
accttgcttc tcctgcactt gccaacctta atactggttt acattgacca acatcttaca   9240
agcgggggc ttgtctaggg tatatataaa cagtggctct cccaatcggt tgccagtctc   9300
tttttccttt tctttcccca cagattcgaa atctaaacta cacatcacag aattccgagc   9360
cgtgagtatc cacgacaaga tcagtgtcga gacgacgcgt tttgtgtaat gacacaatcc   9420
gaaagtcgct agcaacacac actctctaca caaactaacc cagctctggt ac           9472
```

<210> SEQ ID NO 18
<211> LENGTH: 7879
<212> TYPE: DNA
<213> ORGANISM: Artificial Sequence
<220> FEATURE:
<223> OTHER INFORMATION: plasmid pDMW237

<400> SEQUENCE: 18

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
```

-continued

```
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
```

-continued aatcacacac tcaactgtct ttctctcttc tagaaataca ggtacaagta tgtactattc 3780
tcattgttca tacttctagt catttcatcc cacatattcc ttggatttct ctccaatgaa 3840
tgacattcta tcttgcaaat tcaacaatta taataagata taccaaagta gcggtatagt 3900
ggcaatcaaa aagcttctct ggtgtgcttc tcgtatttat ttttattcta atgatccatt 3960
aaaggtatat atttatttct tgttatataa tccttttgtt tattacatgg gctggataca 4020
taaaggtatt ttgatttaat tttttgctta aattcaatcc cccctcgttc agtgtcaact 4080
gtaatggtag gaaattacca tacttttgaa gaagcaaaaa aaatgaaaga aaaaaaaaat 4140
cgtatttcca ggttagacgt tccgcagaat ctagaatgcg gtatgcggta cattgttctt 4200
cgaacgtaaa agttgcgctc cctgagatat tgtacatttt tgcttttaca agtacaagta 4260
catcgtacaa ctatgtacta ctgttgatgc atccacaaca gtttgttttg tttttttttg 4320 ttttttttt ttctaatgat tcattaccgc tatgtatacc tacttgtact tgtagtaagc 4380
cgggttattg gcgttcaatt aatcatagac ttatgaatct gcacggtgtg cgctgcgagt 4440
tacttttagc ttatgcatgc tacttgggtg taatattggg atctgttcgg aaatcaacgg 4500
atgctcaatc gatttcgaca gtaattaatt aagtcataca caagtcagct ttcttcgagc 4560
ctcatataag tataagtagt tcaacgtatt agcactgtac ccagcatctc cgtatcgaga 4620
aacacaacaa catgccccat tggacagatc atgcggatac acaggttgtg cagtatcata 4680
catactcgat cagacaggtc gtctgaccat catacaagct gaacaagcgc tccatacttg 4740
cacgctctct atatacacag ttaaattaca tatccatagt ctaacctcta acagttaatc 4800
ttctggtaag cctcccagcc agccttctgg tatcgcttgg cctcctcaat aggatctcgg 4860
ttctggccgt acagacctcg gccgacaatt atgatatccg ttccggtaga catgacatcc 4920
tcaacagttc ggtactgctg tccgagagcg tctcccttgt cgtcaagacc caccccgggg 4980
gtcagaataa gccagtcctc agagtcgccc ttaggtcggt tctgggcaat gaagccaacc 5040
acaaactcgg ggtcggatcg ggcaagctca atggtctgct tggagtactc gccagtggcc 5100
agagagccct tgcaagacag ctcggccagc atgagcagac ctctggccag cttctcgttg 5160
ggagagggga ctaggaactc cttgtactgg gagttctcgt agtcagagac gtcctccttc 5220
ttctgttcag agacagtttc ctcggcacca gctcgcaggc cagcaatgat tccggttccg 5280
ggtacaccgt gggcgttggt gatatcggac cactcggcga ttcggtgaca ccggtactgg 5340
tgcttgacag tgttgccaat atctgcgaac tttctgtcct cgaacaggaa gaaaccgtgc 5400
ttaagagcaa gttccttgag ggggagcaca gtgccggcgt aggtgaagtc gtcaatgatg 5460
tcgatatggg ttttgatcat gcacacataa ggtccgacct tatcggcaag ctcaatgagc 5520
tccttggtgg tggtaacatc cagagaagca cacaggttgg ttttcttggc tgccacgagc 5580
ttgagcactc gagcggcaaa ggcggacttg tggacgttag ctcgagcttc gtaggagggc 5640 atttggtgg tgaagaggag actgaaataa atttagtctg cagaactttt tatcggaacc 5700
ttatctgggg cagtgaagta tatgttatgg taatagttac gagttagttg aacttataga 5760
tagactggac tatacggcta tcggtccaaa ttagaaagaa cgtcaatggc tctctgggcg 5820
tcgcctttgc cgacaaaaat gtgatcatga tgaaagccag caatgacgtt gcagctgata 5880
ttgttgtcgg ccaaccgcgc cgaaaacgca gctgtcagac ccacagcctc caacgaagaa 5940
tgtatcgtca aagtgatcca agcacactca tagttggagt cgtactccaa aggcggcaat 6000
gacgagtcag acagatactc gtcgactcag gcgacgacgg aattcctgca gcccatctgc 6060
agaattcagg agagaccggg ttggcggcgt atttgtgtcc caaaaaacag ccccaattgc 6120
cccggagaag acggccaggc cgcctagatg acaaattcaa caactcacag ctgactttct 6180
gccattgcca ctaggggggg gcctttttat atggccaagc caagctctcc acgtcggttg 6240
ggctgcaccc aacaataaat gggtagggtt gcaccaacaa agggatggga tgggggtag 6300 aagatacgag gataacgggg ctcaatggca caaataagaa cgaatactgc cattaagact 6360
cgtgatccag cgactgacac cattgcatca tctaagggcc tcaaaactac ctcggaactg 6420
ctgcgctgat ctggacacca cagaggttcc gagcacttta ggttgcacca aatgtcccac 6480
caggtgcagg cagaaaacgc tggaacagcg tgtacagttt gtcttaacaa aaagtgaggg 6540
cgctgaggtc gagcagggtg gtgtgacttg ttatagcctt tagagctgcg aaagcgcgta 6600
tggatttggc tcatcaggcc agattgaggg tctgtggaca catgtcatgt tagtgtactt 6660
caatcgcccc ctggatatag ccccgacaat aggccgtggc ctcatttttt tgccttccgc 6720
acatttccat tgctcggtac ccacaccttg cttctcctgc acttgccaac cttaatactg 6780
gtttacattg accaacatct tacaagcggg gggcttgtct agggtatata taaacagtgg 6840
ctctcccaat cggttgccag tctctttttt cctttctttc cccacagatt cgaaatctaa 6900
actacacatc acacaatgcc tgttactgac gtccttaagc gaaagtccgg tgtcatcgtc 6960
ggcgacgatg tccgagccgt gagtatccac gacaagatca gtgtcgagac gacgcgtttt 7020
gtgtaatgac acaatccgaa agtcgctagc aacacacact ctctacacaa actaacccag 7080
ctctccatgg ctctggccaa cgacgctggc gagcgaatct gggctgccgt caccgatccc 7140
gaaatcctca ttggcacctt ctcctacctg ctcctgaagc ctctcctgcg aaactctggt 7200
ctcgtggacg agaagaaagg agcctaccga acctccatga tctggtacaa cgtcctcctg 7260
gctctcttct ctgccctgtc cttctacgtg actgccaccg ctctcggctg ggactacggt 7320
actggagcct ggctgcgaag acagaccggt gatactcccc agcctctctt tcagtgtccc 7380
tctcctgtct gggactccaa gctgttcacc tggactgcca aggccttcta ctattctaag 7440
tacgtggagt acctcgacac cgcttggctg gtcctcaagg gcaagcgagt gtcctttctg 7500
caggccttcc atcactttgg agctccctgg gacgtctacc tcggcattcg actgcacaac 7560
gagggtgtgt ggatcttcat gttctttaac tcgttcattc acaccatcat gtacacctac 7620
tatggactga ctgccgctgg ctacaagttc aaggccaagc ctctgatcac tgccatgcag 7680
atttgccagt tcgtcggtgg ctttctcctg gtctgggact acatcaacgt tccctgcttc 7740
aactctgaca agggcaagct gttctcctgg gctttcaact acgcctacgt cggatctgtc 7800
tttctcctgt tctgtcactt cttttaccag gacaacctgg ccaccaagaa atccgctaag 7860
gctggtaagc agctttagc 7879

<210> SEQ ID NO 19
<211> LENGTH: 7783
<212> TYPE: DNA
<213> ORGANISM: Artificial Sequence
<220> FEATURE:
<223> OTHER INFORMATION: plasmid pY115

<400> SEQUENCE: 19
catggctctg gccaacgacg ctggcgagcg aatctgggct gccgtcaccg atcccgaaat 60
cctcattggc accttctcct acctgctcct gaagcctctc ctgcgaaact ctggtctcgt 120
ggacgagaag aaaggagcct accgaacctc catgatctgg tacaacgtcc tcctggctct 180
cttctctgcc ctgtccttct acgtgactgc caccgctctc ggctgggact acggtactgg 240
agcctggctg cgaagacaga ccggtgatac tccccagcct ctctttcagt gtccctctcc 300

-continued

```
tgtctgggac tccaagctgt tcacctggac tgccaaggcc ttctactatt ctaagtacgt    360
ggagtacctc gacaccgctt ggctggtcct caagggcaag cgagtgtcct ttctgcaggc    420
cttccatcac tttggagctc cctgggacgt ctacctcggc attcgactgc acaacgaggg    480
tgtgtggatc ttcatgttct ttaactcgtt cattcacacc atcatgtaca cctactatgg    540
actgactgcc gctggctaca agttcaaggc caagcctctg atcactgcca tgcagatttg    600
ccagttcgtc ggtggctttc tcctggtctg ggactacatc aacgttccct gcttcaactc    660
tgacaagggc aagctgttct cctgggcttt caactacgcc tacgtcggat ctgtctttct    720
cctgttctgt cacttctttt accaggacaa cctggccacc aagaaatccg ctaaggctgg    780
taagcagctt tagcggccgc aagtgtggat ggggaagtga gtgcccggtt ctgtgtgcac    840
aattggcaat ccaagatgga tggattcaac acagggatat agcgagctac gtggtggtgc    900
gaggatatag caacggatat ttatgtttga cacttgagaa tgtacgatac aagcactgtc    960
caagtacaat actaaacata ctgtacatac tcatactcgt acccgggcaa cggtttcact   1020
tgagtgcagt ggctagtgct cttactcgta cagtgtgcaa tactgcgtat catagtcttt   1080
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta aagtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
```

-continued

```
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg tttttcgccc   3480
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttatttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct taaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
agtagcggta tagtggcaat caaaaagctt ctctggtgtg cttctcgtat ttatttttat   4740
tctaatgatc cattaaaggt atatatttat ttcttgttat ataatccttt tgtttattac   4800
atgggctgga tacataaagg tattttgatt taatttttttg cttaaattca atcccccctc   4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca tttttgcttt   5040
tacaagtaca agtacatcgt acaactatgt actactgttg atgcatccac aacagtttgt   5100
```

-continued

```
tttgtttttt tttgtttttt ttttttctaa tgattcatta ccgctatgta tacctacttg   5160
tacttgtagt aagccgggtt attggcgttc aattaatcat agacttatga atctgcacgg   5220
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
tctaacagtt aatcttctgg taagcctccc agccagcctt ctggtatcgc ttggcctcct   5640
caataggatc tcggttctgg ccgtacagac ctcggccgac aattatgata tccgttccgg   5700
tagacatgac atcctcaaca gttcggtact gctgtccgag agcgtctccc ttgtcgtcaa   5760
gacccacccc gggggtcaga ataagccagt cctcagagtc gcccttaggt cggttctggg   5820
caatgaagcc aaccacaaac tcggggtcgg atcgggcaag ctcaatggtc tgcttggagt   5880
actcgccagt ggccagagag cccttgcaag acagctcggc cagcatgagc agacctctgg   5940
ccagcttctc gttgggagag gggactagga actccttgta ctgggagttc tcgtagtcag   6000
agacgtcctc cttcttctgt tcagagacag tttcctcggc accagctcgc aggccagcaa   6060
tgattccggt tccgggtaca ccgtgggcgt tggtgatatc ggaccactcg gcgattcggt   6120
gacaccggta ctggtgcttg acagtgttgc caatatctgc gaactttctg tcctcgaaca   6180
ggaagaaacc gtgcttaaga gcaagttcct tgagggggag cacagtgccg gcgtaggtga   6240
agtcgtcaat gatgtcgata tgggttttga tcatgcacac ataaggtccg accttatcgg   6300
caagctcaat gagctccttg gtggtggtaa catccagaga agcacacagg ttggttttct   6360
tggctgccac gagcttgagc actcgagcgg caaaggcgga cttgtggacg ttagctcgag   6420
cttcgtagga gggcattttg gtggtgaaga ggagactgaa ataaatttag tctgcagaac   6480
tttttatcgg aaccttatct ggggcagtga agtatatgtt atggtaatag ttacgagtta   6540
gttgaactta tagatagact ggactatacg gctatcggtc caaattagaa agaacgtcaa   6600
tggctctctg ggcgtcgcct ttgccgacaa aaatgtgatc atgatgaaag ccagcaatga   6660
cgttgcagct gatattgttg tcggccaacc gcgccgaaaa cgcagctgtc agacccacag   6720
cctccaacga agaatgtatc gtcaaagtga tccaagcaca ctcatagttg gagtcgtact   6780
ccaaaggcgg caatgacgag tcagacagat actcgtcgac gtttaaacag tgtacgcaga   6840
tctactatag aggaacattt aaattgcccc ggagaagacg gccaggccgc ctagatgaca   6900
aattcaacaa ctcacagctg actttctgcc attgccacta ggggggggcc tttttatatg   6960
gccaagccaa gctctccacg tcggttgggc tgcacccaac aataaatggg tagggttgca   7020
ccaacaaagg gatgggatgg ggggtagaag atacgaggat aacggggctc aatggcacaa   7080
ataagaacga atactgccat taagactcgt gatccagcga ctgacaccat tgcatcatct   7140
aagggcctca aaactacctc ggaactgctg cgctgatctg gacaccacag aggttccgag   7200
cactttaggt tgcaccaaat gtcccaccag gtgcaggcag aaaacgctgg aacagcgtgt   7260
acagtttgtc ttaacaaaaa gtgagggcgc tgaggtcgag cagggtggtg tgacttgtta   7320
tagcctttag agctgcgaaa gcgcgtatgg atttggctca tcaggccaga ttgagggtct   7380
gtggacacat gtcatgttag tgtacttcaa tcgcccctg gatatagccc cgacaatagg   7440
ccgtggcctc atttttttgc cttccgcaca tttccattgc tcgataccca caccttgctt   7500
```

ctcctgcact tgccaacctt aatactggtt tacattgacc aacatcttac aagcgggggg 7560
cttgtctagg gtatatataa acagtggctc tcccaatcgg ttgccagtct cttttttcct 7620
ttctttcccc acagattcga aatctaaact acacatcaca gaattccgag ccgtgagtat 7680
ccacgacaag atcagtgtcg agacgacgcg ttttgtgtaa tgacacaatc cgaaagtcgc 7740
tagcaacaca cactctctac acaaactaac ccagctctgg tac 7783

<210> SEQ ID NO 20
<211> LENGTH: 19
<212> TYPE: DNA
<213> ORGANISM: Artificial Sequence
<220> FEATURE:
<223> OTHER INFORMATION: oligonucleotide oYFBA1

<400> SEQUENCE: 20
acgcagatct actatagag 19

<210> SEQ ID NO 21
<211> LENGTH: 27
<212> TYPE: DNA
<213> ORGANISM: Artificial Sequence
<220> FEATURE:
<223> OTHER INFORMATION: oligonucleotide oYFBA1-6

<400> SEQUENCE: 21
agcggccgct ggtaccagag ctgggtt 27

<210> SEQ ID NO 22
<211> LENGTH: 6992
<212> TYPE: DNA
<213> ORGANISM: Artificial Sequence
<220> FEATURE:
<223> OTHER INFORMATION: plasmid pY158

<400> SEQUENCE: 22
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc ggcaacggtt tcacttgagt gcagtggcta 240
gtgctcttac tcgtacagtg tgcaatactg cgtatcatag tctttgatgt atatcgtatt 300
cattcatgtt agttgcgtac gagccggaag cataaagtgt aaagcctggg gtgcctaatg 360
agtgagctaa ctcacattaa ttgcgttgcg ctcactgccc gctttccagt cgggaaacct 420
gtcgtgccag ctgcattaat gaatcggcca acgcgcgggg agaggcggtt tgcgtattgg 480
gcgctcttcc gcttcctcgc tcactgactc gctgcgctcg gtcgttcggc tgcggcgagc 540
ggtatcagct cactcaaagg cggtaatacg gttatccaca gaatcagggg ataacgcagg 600
aaagaacatg tgagcaaaag gccagcaaaa ggccaggaac cgtaaaaagg ccgcgttgct 660
ggcgtttttc cataggctcc gcccccctga cgagcatcac aaaaatcgac gctcaagtca 720
gaggtggcga aacccgacag gactataaag ataccaggcg tttccccctg gaagctccct 780
cgtgcgctct cctgttccga ccctgccgct taccggatac ctgtccgcct ttctcccttc 840
gggaagcgtg gcgctttctc atagctcacg ctgtaggtat ctcagttcgg tgtaggtcgt 900
tcgctccaag ctgggctgtg tgcacgaacc ccccgttcag cccgaccgct gcgccttatc 960
cggtaactat cgtcttgagt ccaacccggt aagacacgac ttatcgccac tggcagcagc 1020
cactggtaac aggattagca gagcgaggta tgtaggcggt gctacagagt tcttgaagtg 1080

```
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaaggat ctcaagaaga   1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aagggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggccccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat ttcgggccca ataatttaaa aaaatcgtgt tatataatat   3240
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
tgaacttatt tttattactt agtattatta gacaacttac ttgctttatg aaaaacactt   3480
```

```
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat cccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct   3780
cattgttcat acttctagtc atttcatccc acatattcct tggatttctc tccaatgaat   3840
gacattctat cttgcaaatt caacaattat aataagatat accaaagtag cggtatagtg   3900
gcaatcaaaa agcttctctg gtgtgcttct cgtatttatt tttattctaa tgatccatta   3960
aaggtatata tttatttctt gttatataat ccttttgttt attacatggg ctggatacat   4020
aaaggtattt tgatttaatt ttttgcttaa attcaatccc ccctcgttca gtgtcaactg   4080
taatggtagg aaattaccat acttttgaag aagcaaaaaa aatgaaagaa aaaaaaaatc   4140
gtatttccag gttagacgtt ccgcagaatc tagaatgcgg tatgcggtac attgttcttc   4200
gaacgtaaaa gttgcgctcc ctgagatatt gtacattttt gcttttacaa gtacaagtac   4260
atcgtacaac tatgtactac tgttgatgca tccacaacag tttgttttgt ttttttttgt   4320
ttttttttt tctaatgatt cattaccgct atgtatacct acttgtactt gtagtaagcc   4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt tcttcgagcc   4560
tcatataagt ataagtagtt caacgtatta gcactgtacc cagcatctcc gtatcgagaa   4620
acacaacaac atgccccatt ggacagatca tgcggataca caggttgtgc agtatcatac   4680
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
caacagttcg gtactgctgt ccgagagcgt ctcccttgtc gtcaagaccc accccggggg   4980
tcagaataag ccagtcctca gagtcgccct taggtcggtt ctgggcaatg aagccaacca   5040
caaactcggg gtcggatcgg gcaagctcaa tggtctgctt ggagtactcg ccagtggcca   5100
gagagccctt gcaagacagc tcggccagca tgagcagacc tctggccagc ttctcgttgg   5160
gagaggggac taggaactcc ttgtactggg agttctcgta gtcagagacg tcctccttct   5220
tctgttcaga gacagtttcc tcggcaccag ctcgcaggcc agcaatgatt ccggttccgg   5280
gtacaccgtg ggcgttggtg atatcggacc actcggcgat tcggtgacac cggtactggt   5340
gcttgacagt gttgccaata tctgcgaact ttctgtcctc gaacaggaag aaaccgtgct   5400
taagagcaag ttccttgagg gggagcacag tgccggcgta ggtgaagtcg tcaatgatgt   5460
cgatatgggt tttgatcatg cacacataag gtccgacctt atcggcaagc tcaatgagct   5520
ccttggtggt ggtaacatcc agagaagcac acaggttggt tttcttggct gccacgagct   5580
tgagcactcg agcggcaaag gcggacttgt ggacgttagc tcgagcttcg taggagggca   5640
ttttggtggt gaagaggaga ctgaaataaa tttagtctgc agaacttttt atcggaacct   5700
tatctggggc agtgaagtat atgttatggt aatagttacg agttagttga acttatagat   5760
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
```

```
tgttgtcggc caaccgcgcc gaaaacgcag ctgtcagacc cacagcctcc aacgaagaat   5940

gtatcgtcaa agtgatccaa gcacactcat agttggagtc gtactccaaa ggcggcaatg   6000

acgagtcaga cagatactcg tcgacgttta aacagtgtac gcagatctac tatagaggaa   6060

catttaaatt gccccggaga agacggccag gccgcctaga tgacaaattc aacaactcac   6120

agctgacttt ctgccattgc cactaggggg gggccttttt atatggccaa gccaagctct   6180

ccacgtcggt tgggctgcac ccaacaataa atgggtaggg ttgcaccaac aaagggatgg   6240

gatggggggt agaagatacg aggataacgg ggctcaatgg cacaaataag aacgaatact   6300

gccattaaga ctcgtgatcc agcgactgac accattgcat catctaaggg cctcaaaact   6360

acctcggaac tgctgcgctg atctggacac cacagaggtt ccgagcactt taggttgcac   6420

caaatgtccc accaggtgca ggcagaaaac gctggaacag cgtgtacagt ttgtcttagc   6480

aaaaagtgaa ggcgctgagg tcgagcaggg tggtgtgact tgttatagcc tttagagctg   6540

cgaaagcgcg tatggatttg gctcatcagg ccagattgag ggtctgtgga cacatgtcat   6600

gttagtgtac ttcaatcgcc ccctggatat agccccgaca ataggccgtg gcctcatttt   6660

tttgccttcc gcacatttcc attgctcgat acccacacct tgcttctcct gcacttgcca   6720

accttaatac tggtttacat tgaccaacat cttacaagcg gggggcttgt ctagggtata   6780

tataaacagt ggctctccca atcggttgcc agtctctttt ttcctttctt tccccacaga   6840

ttcgaaatct aaactacaca tcacagaatt ccgagccgtg agtatccacg acaagatcag   6900

tgtcgagacg acgcgttttg tgtaatgaca caatccgaaa gtcgctagca acacacactc   6960

tctacacaaa ctaacccagc tctggtacca gc                                  6992
```

```
<210> SEQ ID NO 23
<211> LENGTH: 8707
<212> TYPE: DNA
<213> ORGANISM: Artificial Sequence
<220> FEATURE:
<223> OTHER INFORMATION: plasmid pY159

<400> SEQUENCE: 23
```

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc ggcaacggtt tcacttgagt gcagtggcta    240

gtgctcttac tcgtacagtg tgcaatactg cgtatcatag tctttgatgt atatcgtatt    300

cattcatgtt agttgcgtac gagccggaag cataaagtgt aaagcctggg gtgcctaatg    360

agtgagctaa ctcacattaa ttgcgttgcg ctcactgccc gctttccagt cgggaaacct    420

gtcgtgccag ctgcattaat gaatcggcca acgcgcgggg agaggcggtt tgcgtattgg    480

gcgctcttcc gcttcctcgc tcactgactc gctgcgctcg gtcgttcggc tgcggcgagc    540

ggtatcagct cactcaaagg cggtaatacg gttatccaca gaatcagggg ataacgcagg    600

aaagaacatg tgagcaaaag gccagcaaaa ggccaggaac cgtaaaaagg ccgcgttgct    660

ggcgtttttc cataggctcc gcccccctga cgagcatcac aaaaatcgac gctcaagtca    720

gaggtggcga aacccgacag gactataaag ataccaggcg tttccccctg gaagctccct    780

cgtgcgctct cctgttccga ccctgccgct taccggatac ctgtccgcct ttctcccttc    840

gggaagcgtg gcgctttctc atagctcacg ctgtaggtat ctcagttcgg tgtaggtcgt    900

tcgctccaag ctgggctgtg tgcacgaacc ccccgttcag cccgaccgct gcgccttatc    960
```

-continued

```
cggtaactat cgtcttgagt ccaacccggt aagacacgac ttatcgccac tggcagcagc   1020
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaaggat ctcaagaaga   1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aagggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggccccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat ttcgggccaa ataatttaaa aaaatcgtgt tatataatat   3240
tatatgtatt atatatatac atcatgatga tactgacagt catgtcccat tgctaaatag   3300
acagactcca tctgccgcct ccaactgatg ttctcaatat ttaaggggtc atctcgcatt   3360
```

gtttaataat aaacagactc catctaccgc ctccaaatga tgttctcaaa atatattgta 3420
tgaacttatt tttattactt agtattatta gacaacttac ttgctttatg aaaaacactt 3480
cctatttagg aaacaattta taatggcagt tcgttcattt aacaatttat gtagaataaa 3540
tgttataaat gcgtatggga aatcttaaat atggatagca taaatgatat ctgcattgcc 3600
taattcgaaa tcaacagcaa cgaaaaaaat cccttgtaca acataaatag tcatcgagaa 3660
atatcaacta tcaaagaaca gctattcaca cgttactatt gagattatta ttggacgaga 3720
atcacacact caactgtctt tctctcttct agaaatacag gtacaagtat gtactattct 3780
cattgttcat acttctagtc atttcatccc acatattcct tggatttctc tccaatgaat 3840
gacattctat cttgcaaatt caacaattat aataagatat accaaagtag cggtatagtg 3900
gcaatcaaaa agcttctctg gtgtgcttct cgtatttatt tttattctaa tgatccatta 3960
aaggtatata tttatttctt gttatataat ccttttgttt attacatggg ctggatacat 4020
aaaggtattt tgatttaatt ttttgcttaa attcaatccc ccctcgttca gtgtcaactg 4080
taatggtagg aaattaccat acttttgaag aagcaaaaaa aatgaaagaa aaaaaaaatc 4140
gtatttccag gttagacgtt ccgcagaatc tagaatgcgg tatgcggtac attgttcttc 4200
gaacgtaaaa gttgcgctcc ctgagatatt gtacattttt gcttttacaa gtacaagtac 4260
atcgtacaac tatgtactac tgttgatgca tccacaacag tttgttttgt tttttttgt 4320 ttttttttt tctaatgatt cattaccgct atgtatacct acttgtactt gtagtaagcc 4380
gggttattgg cgttcaatta atcatagact tatgaatctg cacggtgtgc gctgcgagtt 4440
acttttagct tatgcatgct acttgggtgt aatattggga tctgttcgga aatcaacgga 4500
tgctcaatcg atttcgacag taattaatta agtcatacac aagtcagctt tcttcgagcc 4560
tcatataagt ataagtagtt caacgtatta gcactgtacc cagcatctcc gtatcgagaa 4620
acacaacaac atgccccatt ggacagatca tgcggataca caggttgtgc agtatcatac 4680
atactcgatc agacaggtcg tctgaccatc atacaagctg aacaagcgct ccatacttgc 4740
acgctctcta tatacacagt taaattacat atccatagtc taacctctaa cagttaatct 4800
tctggtaagc ctcccagcca gccttctggt atcgcttggc ctcctcaata ggatctcggt 4860
tctggccgta cagacctcgg ccgacaatta tgatatccgt tccggtagac atgacatcct 4920
caacagttcg gtactgctgt ccgagagcgt ctcccttgtc gtcaagaccc accccggggg 4980
tcagaataag ccagtcctca gagtcgccct taggtcggtt ctgggcaatg aagccaacca 5040
caaactcggg gtcggatcgg gcaagctcaa tggtctgctt ggagtactcg ccagtggcca 5100
gagagccctt gcaagacagc tcggccagca tgagcagacc tctggccagc ttctcgttgg 5160
gagaggggac taggaactcc ttgtactggg agttctcgta gtcagagacg tcctccttct 5220
tctgttcaga gacagtttcc tcggcaccag ctcgcaggcc agcaatgatt ccggttccgg 5280
gtacaccgtg ggcgttggtg atatcggacc actcggcgat tcggtgacac cggtactggt 5340
gcttgacagt gttgccaata tctgcgaact ttctgtcctc gaacaggaag aaaccgtgct 5400
taagagcaag ttccttgagg gggagcacag tgccggcgta ggtgaagtcg tcaatgatgt 5460
cgatatgggt tttgatcatg cacacataag gtccgacctt atcggcaagc tcaatgagct 5520
ccttggtggt ggtaacatcc agagaagcac acaggttggt tttcttggct gccacgagct 5580
tgagcactcg agcggcaaag gcggacttgt ggacgttagc tcgagcttcg taggagggca 5640
ttttggtggt gaagaggaga ctgaaataaa tttagtctgc agaactttt atcggaacct 5700 tatctggggc agtgaagtat atgttatggt aatagttacg agttagttga acttatagat 5760

-continued

```
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
tgttgtcggc caaccgcgcc gaaaacgcag ctgtcagacc cacagcctcc aacgaagaat   5940
gtatcgtcaa agtgatccaa gcacactcat agttggagtc gtactccaaa ggcggcaatg   6000
acgagtcaga cagatactcg tcgacgttta aacagtgtac gcagatctac tatagaggaa   6060
catttaaatt gccccggaga agacggccag gccgcctaga tgacaaattc aacaactcac   6120
agctgacttt ctgccattgc cactaggggg gggccttttt atatggccaa gccaagctct   6180
ccacgtcggt tgggctgcac ccaacaataa atgggtaggg ttgcaccaac aaagggatgg   6240
gatggggggt agaagatacg aggataacgg ggctcaatgg cacaaataag aacgaatact   6300
gccattaaga ctcgtgatcc agcgactgac accattgcat catctaaggg cctcaaaact   6360
acctcggaac tgctgcgctg atctggacac cacagaggtt ccgagcactt taggttgcac   6420
caaatgtccc accaggtgca ggcagaaaac gctggaacag cgtgtacagt ttgtcttagc   6480
aaaaagtgaa ggcgctgagg tcgagcaggg tggtgtgact tgttatagcc tttagagctg   6540
cgaaagcgcg tatggatttg gctcatcagg ccagattgag ggtctgtgga cacatgtcat   6600
gttagtgtac ttcaatcgcc ccctggatat agccccgaca ataggccgtg gcctcatttt   6660
tttgccttcc gcacatttcc attgctcgat acccacacct tgcttctcct gcacttgcca   6720
accttaatac tggtttacat tgaccaacat cttacaagcg gggggcttgt ctagggtata   6780
tataaacagt ggctctccca atcggttgcc agtctctttt ttcctttctt tccccacaga   6840
ttcgaaatct aaactacaca tcacagaatt ccgagccgtg agtatccacg acaagatcag   6900
tgtcgagacg acgcgttttg tgtaatgaca caatccgaaa gtcgctagca acacacactc   6960
tctacacaaa ctaacccagc tctggtacca gcggccatca caagtttgta caaaaaagct   7020
gaacgagaaa cgtaaaatga tataaatatc aatatattaa attagatttt gcataaaaaa   7080
cagactacat aatactgtaa aacacaacat atccagtcat attggcggcc gcattaggca   7140
ccccaggctt tacactttat gcttccggct cgtataatgt gtggattttg agttaggatc   7200
cgtcgagatt ttcaggagct aaggaagcta aaatggagaa aaaaatcact ggatatacca   7260
ccgttgatat atcccaatgg catcgtaaag aacattttga ggcatttcag tcagttgctc   7320
aatgtaccta taaccagacc gttcagctgg atattacggc ctttttaaag accgtaaaga   7380
aaaataagca caagttttat ccggccttta ttcacattct tgcccgcctg atgaatgctc   7440
atccggaatt ccgtatggca atgaaagacg gtgagctggt gatatgggat agtgttcacc   7500
cttgttacac cgttttccat gagcaaactg aaacgttttc atcgctctgg agtgaatacc   7560
acgacgattt ccggcagttt ctacacatat attcgcaaga tgtggcgtgt tacggtgaaa   7620
acctggccta tttccctaaa gggtttattg agaatatgtt tttcgtctca gccaatccct   7680
gggtgagttt caccagtttt gatttaaacg tggccaatat ggacaacttc ttcgcccccg   7740
ttttcaccat gggcaaatat tatacgcaag gcgacaaggt gctgatgccg ctggcgattc   7800
aggttcatca tgccgtttgt gatggcttcc atgtcggcag aatgcttaat gaattacaac   7860
agtactgcga tgagtggcag ggcggggcgt aaacgcgtgg atccggctta ctaaaagcca   7920
gataacagta tgcgtatttg cgcgctgatt tttgcggtat aagaatatat actgatatgt   7980
atacccgaag tatgtcaaaa agaggtatgc tatgaagcag cgtattacag tgacagttga   8040
cagcgacagc tatcagttgc tcaaggcata tatgatgtca atatctccgg tctggtaagc   8100
acaaccatgc agaatgaagc ccgtcgtctg cgtgccgaac gctggaaagc ggaaaatcag   8160
```

gaagggatgg ctgaggtcgc ccggtttatt gaaatgaacg gctcttttgc tgacgagaac 8220
aggggctggt gaaatgcagt ttaaggttta cacctataaa agagagagcc gttatcgtct 8280
gtttgtggat gtacagagtg atattattga cacgcccggg cgacggatgg tgatccccct 8340
ggccagtgca cgtctgctgt cagataaagt ctcccgtgaa ctttacccgg tggtgcatat 8400
cggggatgaa agctggcgca tgatgaccac cgatatggcc agtgtgccgg tctccgttat 8460
cggggaagaa gtggctgatc tcagccaccg cgaaaatgac atcaaaaacg ccattaacct 8520
gatgttctgg ggaatataaa tgtcaggctc ccttatacac agccagtctg caggtcgacc 8580
atagtgactg gatatgttgt gttttacagc attatgtagt ctgtttttta tgcaaaatct 8640
aatttaatat attgatattt atatcatttt acgtttctcg ttcagctttc ttgtacaaag 8700
tggtgat 8707

<210> SEQ ID NO 24
<211> LENGTH: 8827
<212> TYPE: DNA
<213> ORGANISM: Artificial Sequence
<220> FEATURE:
<223> OTHER INFORMATION: plasmid pY169

<400> SEQUENCE: 24
cttgtacaaa gtggtgatgg ccgcaagtgt ggatggggaa gtgagtgccc ggttctgtgt 60
gcacaattgg caatccaaga tggatggatt caacacaggg atatagcgag ctacgtggtg 120
gtgcgaggat atagcaacgg atatttatgt ttgacacttg agaatgtacg atacaagcac 180
tgtccaagta caatactaaa catactgtac atactcatac tcgtacccgg caacggtttc 240
acttgagtgc agtggctagt gctcttactc gtacagtgtg caatactgcg tatcatagtc 300
tttgatgtat atcgtattca ttcatgttag ttgcgtacga gccggaagca taaagtgtaa 360
agcctggggt gcctaatgag tgagctaact cacattaatt gcgttgcgct cactgcccgc 420
tttccagtcg ggaaacctgt cgtgccagct gcattaatga atcggccaac gcgcggggag 480
aggcggtttg cgtattgggc gctcttccgc ttcctcgctc actgactcgc tgcgctcggt 540
cgttcggctg cggcgagcgg tatcagctca ctcaaaggcg gtaatacggt tatccacaga 600
atcaggggat aacgcaggaa agaacatgtg agcaaaaggc cagcaaaagg ccaggaaccg 660
taaaaaggcc gcgttgctgg cgtttttcca taggctccgc ccccctgacg agcatcacaa 720
aaatcgacgc tcaagtcaga ggtggcgaaa cccgacagga ctataaagat accaggcgtt 780
tccccctgga agctccctcg tgcgctctcc tgttccgacc ctgccgctta ccggatacct 840
gtccgccttt ctcccttcgg gaagcgtggc gctttctcat agctcacgct gtaggtatct 900
cagttcggtg taggtcgttc gctccaagct gggctgtgtg cacgaacccc ccgttcagcc 960
cgaccgctgc gccttatccg gtaactatcg tcttgagtcc aacccggtaa gacacgactt 1020
atcgccactg gcagcagcca ctggtaacag gattagcaga gcgaggtatg taggcggtgc 1080
tacagagttc ttgaagtggt ggcctaacta cggctacact agaaggacag tatttggtat 1140
ctgcgctctg ctgaagccag ttaccttcgg aaaaagagtt ggtagctctt gatccggcaa 1200
acaaaccacc gctggtagcg gtggtttttt tgtttgcaag cagcagatta cgcgcagaaa 1260
aaaaggatct caagaagatc ctttgatctt ttctacgggg tctgacgctc agtggaacga 1320
aaactcacgt taagggattt tggtcatgag attatcaaaa aggatcttca cctagatcct 1380
tttaaattaa aaatgaagtt ttaaatcaat ctaaagtata tatgagtaaa cttggtctga 1440
cagttaccaa tgcttaatca gtgaggcacc tatctcagcg atctgtctat ttcgttcatc 1500
catagttgcc tgactccccg tcgtgtagat aactacgata cgggagggct taccatctgg 1560
ccccagtgct gcaatgatac cgcgagaccc acgctcaccg gctccagatt tatcagcaat 1620
aaaccagcca gccggaaggg ccgagcgcag aagtggtcct gcaactttat ccgcctccat 1680
ccagtctatt aattgttgcc gggaagctag agtaagtagt tcgccagtta atagtttgcg 1740
caacgttgtt gccattgcta caggcatcgt ggtgtcacgc tcgtcgtttg gtatggcttc 1800
attcagctcc ggttcccaac gatcaaggcg agttacatga tcccccatgt tgtgcaaaaa 1860
agcggttagc tccttcggtc ctccgatcgt tgtcagaagt aagttggccg cagtgttatc 1920
actcatggtt atggcagcac tgcataattc tcttactgtc atgccatccg taagatgctt 1980
ttctgtgact ggtgagtact caaccaagtc attctgagaa tagtgtatgc ggcgaccgag 2040
ttgctcttgc ccggcgtcaa tacgggataa taccgcgcca catagcagaa ctttaaaagt 2100
gctcatcatt ggaaaacgtt cttcggggcg aaaactctca aggatcttac cgctgttgag 2160
atccagttcg atgtaaccca ctcgtgcacc caactgatct tcagcatctt ttactttcac 2220
cagcgtttct gggtgagcaa aaacaggaag gcaaaatgcc gcaaaaaagg gaataagggc 2280
gacacggaaa tgttgaatac tcatactctt cctttttcaa tattattgaa gcatttatca 2340
gggttattgt ctcatgagcg gatacatatt tgaatgtatt tagaaaaata aacaaatagg 2400
ggttccgcgc acatttcccc gaaaagtgcc acctgacgcg ccctgtagcg gcgcattaag 2460
cgcggcgggt gtggtggtta cgcgcagcgt gaccgctaca cttgccagcg ccctagcgcc 2520
cgctcctttc gctttcttcc cttcctttct cgccacgttc gccggctttc cccgtcaagc 2580
tctaaatcgg gggctccctt tagggttccg atttagtgct ttacggcacc tcgaccccaa 2640
aaaacttgat tagggtgatg gttcacgtag tgggccatcg ccctgataga cggtttttcg 2700
ccctttgacg ttggagtcca cgttctttaa tagtggactc ttgttccaaa ctggaacaac 2760
actcaaccct atctcggtct attcttttga tttataaggg attttgccga tttcggccta 2820
ttggttaaaa aatgagctga tttaacaaaa atttaacgcg aattttaaca aaatattaac 2880
gcttacaatt tccattcgcc attcaggctg cgcaactgtt gggaagggcg atcggtgcgg 2940
gcctcttcgc tattacgcca gctggcgaaa gggggatgtg ctgcaaggcg attaagttgg 3000
gtaacgccag ggttttccca gtcacgacgt tgtaaaacga cggccagtga attgtaatac 3060
gactcactat agggcgaatt gggtaccggg ccccccctcg aggtcgatgg tgtcgataag 3120
cttgatatcg aattcatgtc acacaaaccg atcttcgcct caaggaaacc taattctaca 3180
tccgagagac tgccgagatc cagtctacac tgattaattt tcgggccaat aatttaaaaa 3240
aatcgtgtta tataatatta tatgtattat atatatacat catgatgata ctgacagtca 3300
tgtcccattg ctaaatagac agactccatc tgccgcctcc aactgatgtt ctcaatattt 3360
aaggggtcat ctcgcattgt ttaataataa acagactcca tctaccgcct ccaaatgatg 3420
ttctcaaaat atattgtatg aacttatttt tattacttag tattattaga caacttactt 3480
gctttatgaa aaacacttcc tatttaggaa acaatttata atggcagttc gttcatttaa 3540
caatttatgt agaataaatg ttataaatgc gtatgggaaa tcttaaatat ggatagcata 3600
aatgatatct gcattgccta attcgaaatc aacagcaacg aaaaaaatcc cttgtacaac 3660
ataaatagtc atcgagaaat atcaactatc aaagaacagc tattcacacg ttactattga 3720
gattattatt ggacgagaat cacacactca actgtctttc tctcttctag aaatacaggt 3780
acaagtatgt actattctca ttgttcatac ttctagtcat ttcatcccac atattccttg 3840
gatttctctc caatgaatga cattctatct tgcaaattca acaattataa taagatatac 3900

```
caaagtagcg gtatagtggc aatcaaaaag cttctctggt gtgcttctcg tatttatttt   3960
tattctaatg atccattaaa ggtatatatt tatttcttgt tatataatcc ttttgtttat   4020
tacatgggct ggatacataa aggtattttg atttaatttt ttgcttaaat tcaatccccc   4080
ctcgttcagt gtcaactgta atggtaggaa attaccatac ttttgaagaa gcaaaaaaaa   4140
tgaaagaaaa aaaaaatcgt atttccaggt tagacgttcc gcagaatcta gaatgcggta   4200
tgcggtacat tgttcttcga acgtaaaagt tgcgctccct gagatattgt acatttttgc   4260
ttttacaagt acaagtacat cgtacaacta tgtactactg ttgatgcatc cacaacagtt   4320
tgttttgttt tttttgttt tttttttttc taatgattca ttaccgctat gtatacctac   4380
ttgtacttgt agtaagccgg gttattggcg ttcaattaat catagactta tgaatctgca   4440
cggtgtgcgc tgcgagttac ttttagctta tgcatgctac ttgggtgtaa tattgggatc   4500
tgttcggaaa tcaacggatg ctcaatcgat ttcgacagta attaattaag tcatacacaa   4560
gtcagctttc ttcgagcctc atataagtat aagtagttca acgtattagc actgtaccca   4620
gcatctccgt atcgagaaac acaacaacat gccccattgg acagatcatg cggatacaca   4680
ggttgtgcag tatcatacat actcgatcag acaggtcgtc tgaccatcat acaagctgaa   4740
caagcgctcc atacttgcac gctctctata tacacagtta aattacatat ccatagtcta   4800
acctctaaca gttaatcttc tggtaagcct cccagccagc cttctggtat cgcttggcct   4860
cctcaatagg atctcggttc tggccgtaca gacctcggcc gacaattatg atatccgttc   4920
cggtagacat gacatcctca acagttcggt actgctgtcc gagagcgtct cccttgtcgt   4980
caagacccac cccgggggtc agaataagcc agtcctcaga gtcgccctta ggtcggttct   5040
gggcaatgaa gccaaccaca aactcggggt cggatcgggc aagctcaatg gtctgcttgg   5100
agtactcgcc agtggccaga gagcccttgc aagacagctc ggccagcatg agcagacctc   5160
tggccagctt ctcgttggga gaggggacta ggaactcctt gtactgggag ttctcgtagt   5220
cagagacgtc ctccttcttc tgttcagaga cagtttcctc ggcaccagct cgcaggccag   5280
caatgattcc ggttccgggt acaccgtggg cgttggtgat atcggaccac tcggcgattc   5340
ggtgacaccg gtactggtgc ttgacagtgt tgccaatatc tgcgaacttt ctgtcctcga   5400
acaggaagaa accgtgctta agagcaagtt ccttgagggg gagcacagtg ccggcgtagg   5460
tgaagtcgtc aatgatgtcg atatgggttt tgatcatgca cacataaggt ccgaccttat   5520
cggcaagctc aatgagctcc ttggtggtgg taacatccag agaagcacac aggttggttt   5580
tcttggctgc cacgagcttg agcactcgag cggcaaaggc ggacttgtgg acgttagctc   5640
gagcttcgta ggagggcatt ttggtggtga agaggagact gaaataaatt tagtctgcag   5700
aactttttat cggaacctta tctggggcag tgaagtatat gttatggtaa tagttacgag   5760
ttagttgaac ttatagatag actggactat acggctatcg gtccaaatta gaaagaacgt   5820
caatggctct ctgggcgtcg cctttgccga caaaaatgtg atcatgatga aagccagcaa   5880
tgacgttgca gctgatattg ttgtcggcca accgcgccga aaacgcagct gtcagaccca   5940
cagcctccaa cgaagaatgt atcgtcaaag tgatccaagc acactcatag ttggagtcgt   6000
actccaaagg cggcaatgac gagtcagaca gatactcgtc gacgtttaaa cagtgtacgc   6060
agatctacta tagaggaaca tttaaattgc cccggagaag acggccaggc cgcctagatg   6120
acaaattcaa caactcacag ctgactttct gccattgcca ctaggggggg gcctttttat   6180
atggccaagc caagctctcc acgtcggttg ggctgcaccc aacaataaat gggtagggtt   6240
gcaccaacaa agggatggga tgggggtag aagatacgag gataacgggg ctcaatggca   6300
```

-continued

```
caaataagaa cgaatactgc cattaagact cgtgatccag cgactgacac cattgcatca   6360
tctaagggcc tcaaaactac ctcggaactg ctgcgctgat ctggacacca cagaggttcc   6420
gagcacttta ggttgcacca aatgtcccac caggtgcagg cagaaaacgc tggaacagcg   6480
tgtacagttt gtcttagcaa aaagtgaagg cgctgaggtc gagcagggtg gtgtgacttg   6540
ttatagcctt tagagctgcg aaagcgcgta tggatttggc tcatcaggcc agattgaggg   6600
tctgtggaca catgtcatgt tagtgtactt caatcgcccc ctggatatag ccccgacaat   6660
aggccgtggc ctcatttttt tgccttccgc acatttccat tgctcgatac ccacaccttg   6720
cttctcctgc acttgccaac cttaatactg gtttacattg accaacatct tacaagcggg   6780
gggcttgtct agggtatata taaacagtgg ctctcccaat cggttgccag tctctttttt   6840
cctttctttc cccacagatt cgaaatctaa actacacatc acagaattcc gagccgtgag   6900
tatccacgac aagatcagtg tcgagacgac gcgttttgtg taatgacaca atccgaaagt   6960
cgctagcaac acacactctc tacacaaact aacccagctc tggtaccagc ggccatcaca   7020
agtttgtaca aaaaagttgg atttttttc gggatggcca ccatctcttt gactactgag    7080
caacttttag aacacccaga actggttgca attgatgggg tgttgtacga tctcttcgga   7140
ctggcgaaag tgcatccagg tggcaacctc attgaagccg ccggtgcctc cgacggaacc   7200
gccctgttct actccatgca ccctggagtg aagccagaga attcgaagct gctgcagcaa   7260
tttgcccgag gcaaacacga acgaagctcg aaggacccag tgtacacctt tgacagtccc   7320
ttcgcccagg atgtcaagca gagcgttcgg gaggtcatga aggggcgcaa ctggtacgcc   7380
acgcccggct tttggctgcg gaccgcgctg atcatcgcgt gcactgccat aggcgaatgg   7440
tattggatca ctaccggggc agtgatgtgg ggcatcttca ccgggtactt ccacagccag   7500
attgggttgg cgattcaaca cgatgcctct cacggagcca tcagcaaaaa gccctgggtg   7560
aacgcctttt tcgcctacgg catcgacgcc attggatcct cccgctggat ctggctgcag   7620
tcccacatta tgcgccacca cacctacacc aaccagcatg gcctggacct ggacgctgcc   7680
tcggcggagc cgttcatttt gttccactcc tacccggcaa caaatgcgtc acgaaagtgg   7740
taccatcggt tccaggcgtg gtacatgtac atcgttttgg ggatgtatgg tgtgtcgatg   7800
gtgtacaatc cgatgtactt gttcacgatg cagcacaacg acacaatccc agaggccacc   7860
tctcttagac caggcagctt tttcaaccgg cagcgcgcct tcgccgtttc cctccgccta   7920
ctgttcatct tccgcaacgc cttcctcccc tggtacatcg cgggcgcctc tccgctgctc   7980
accatcctgc tggtgccaac ggtcacaggc atcttcttga catttgtttt tgtgctgtcc   8040
cataactttg aaggcgctga gcggaccccc gaaaagaact gcaaggccaa aagggccaag   8100
gaggggaagg aggtccgcga tgtagaggag gaccgggtgg actggtaccg ggcgcaggcc   8160
gagaccgcgg cgacctacgg gggcagcgtc gggatgatgc tgaccggcgg tttgaacctg   8220
cagatcgagc accacttgtt cccccgcatg tcctcttggc actacccctt catccaagat   8280
acggtgcggg aatgttgcaa gcgccatggc gtgcgctaca catactaccc gaccatcctg   8340
gagaatataa tgtccacgct ccgctacatg cagaaggtgg gcgtggccca cacaattcag   8400
gatgcccagg aattctgagt gagttcgatc cgcatcgacg tctaccattt ttgatgctgt   8460
ctattcctgt tttcagtcac ctccagcatt ctcatggctg gtgaccactg cccctctaac   8520
ccattgtgac acaccgccaa agactttgcc tctttttttt ccctttcttt tgtcctcggg   8580
gtgctttggc cggtgtttac tcgccttgca gtccccgcaa acgaccgacg tttaagctcc   8640
gttgttgact gggccgctcg taaacccatc tgcaggttga ggctcccatg gagaattgtg   8700
```

```
atggctgatt aggaggtggc ggggcataca tgcctcgaca ctcaaagccg ggcggcttct   8760

ggattcgaaa acgcaaatgg gcgctttgga aaaaaaaaaa aaaaaaaaaa aaaaaaaacc   8820

caacttt                                                              8827


<210> SEQ ID NO 25
<211> LENGTH: 1362
<212> TYPE: DNA
<213> ORGANISM: Artificial Sequence
<220> FEATURE:
<223> OTHER INFORMATION: codon-optimized Euglena anabaena delta-5
      desaturase
<220> FEATURE:
<221> NAME/KEY: CDS
<222> LOCATION: (1)..(1362)
<223> OTHER INFORMATION: synthetic delta-5 desaturase (codon-optimized)
      for Yarrowia lipolytica

<400> SEQUENCE: 25

atg gcc acc atc tcc ctg act acc gag cag ctc ctg gaa cac ccc gag       48
Met Ala Thr Ile Ser Leu Thr Thr Glu Gln Leu Leu Glu His Pro Glu
1               5                   10                  15

ctc gtt gcc atc gac gga gtc ctg tac gat ctc ttc ggt ctg gcc aag       96
Leu Val Ala Ile Asp Gly Val Leu Tyr Asp Leu Phe Gly Leu Ala Lys
            20                  25                  30

gtg cat cca gga ggc aac ctc atc gaa gct gcc ggt gca tcc gac gga      144
Val His Pro Gly Gly Asn Leu Ile Glu Ala Ala Gly Ala Ser Asp Gly
        35                  40                  45

acc gct ctg ttc tac tcc atg cat cct gga gtc aag cca gag aac tcg      192
Thr Ala Leu Phe Tyr Ser Met His Pro Gly Val Lys Pro Glu Asn Ser
    50                  55                  60

aag ctt ctg cag caa ttt gcc cga ggc aag cac gaa cga agc tcc aag      240
Lys Leu Leu Gln Gln Phe Ala Arg Gly Lys His Glu Arg Ser Ser Lys
65                  70                  75                  80

gat ccc gtg tac acc ttc gac tct ccc ttt gct cag gac gtc aag cag      288
Asp Pro Val Tyr Thr Phe Asp Ser Pro Phe Ala Gln Asp Val Lys Gln
                85                  90                  95

tcc gtt cga gag gtc atg aag ggt cga aac tgg tac gcc act cct ggc      336
Ser Val Arg Glu Val Met Lys Gly Arg Asn Trp Tyr Ala Thr Pro Gly
            100                 105                 110

ttc tgg ctg aga acc gca ctc atc atc gct tgt act gcc att ggc gag      384
Phe Trp Leu Arg Thr Ala Leu Ile Ile Ala Cys Thr Ala Ile Gly Glu
        115                 120                 125

tgg tac tgg atc aca acc gga gca gtg atg tgg ggt atc ttt act gga      432
Trp Tyr Trp Ile Thr Thr Gly Ala Val Met Trp Gly Ile Phe Thr Gly
    130                 135                 140

tac ttc cac tcg cag att ggc ttg gcc att caa cac gat gct tct cac      480
Tyr Phe His Ser Gln Ile Gly Leu Ala Ile Gln His Asp Ala Ser His
145                 150                 155                 160

gga gcc atc agc aaa aag ccc tgg gtc aac gcc ttt ttc gct tat ggc      528
Gly Ala Ile Ser Lys Lys Pro Trp Val Asn Ala Phe Phe Ala Tyr Gly
                165                 170                 175

atc gac gcc att ggt tcc tct cgt tgg atc tgg ctg cag tcc cac att      576
Ile Asp Ala Ile Gly Ser Ser Arg Trp Ile Trp Leu Gln Ser His Ile
            180                 185                 190

atg cga cat cac act tac acc aac cag cat ggc ctc gac ctg gat gct      624
Met Arg His His Thr Tyr Thr Asn Gln His Gly Leu Asp Leu Asp Ala
        195                 200                 205

gcc tcg gca gag ccg ttc atc ttg ttc cac tcc tat cct gct acc aac      672
Ala Ser Ala Glu Pro Phe Ile Leu Phe His Ser Tyr Pro Ala Thr Asn
    210                 215                 220

gcc tct cga aag tgg tac cac cga ttt cag gcg tgg tac atg tac atc      720
```

```
Ala Ser Arg Lys Trp Tyr His Arg Phe Gln Ala Trp Tyr Met Tyr Ile
225                 230                 235                 240

gtt ctg gga atg tat ggt gtc tcg atg gtg tac aat ccc atg tac ctc      768
Val Leu Gly Met Tyr Gly Val Ser Met Val Tyr Asn Pro Met Tyr Leu
                245                 250                 255

ttc aca atg cag cac aac gac acc att ccc gag gcc act tct ctc aga      816
Phe Thr Met Gln His Asn Asp Thr Ile Pro Glu Ala Thr Ser Leu Arg
            260                 265                 270

cca ggc agc ttt ttc aat cgg cag cga gct ttc gcc gtt tcc ctt cga      864
Pro Gly Ser Phe Phe Asn Arg Gln Arg Ala Phe Ala Val Ser Leu Arg
        275                 280                 285

ctg ctc ttc atc ttc cga aac gcc ttt ctt ccc tgg tac att gct ggt      912
Leu Leu Phe Ile Phe Arg Asn Ala Phe Leu Pro Trp Tyr Ile Ala Gly
    290                 295                 300

gcc tct cct ctg ctc acc att ctt ctg gtg ccc acg gtc aca ggc atc      960
Ala Ser Pro Leu Leu Thr Ile Leu Leu Val Pro Thr Val Thr Gly Ile
305                 310                 315                 320

ttc ctc acc ttt gtg ttc gtt ctg tcc cat aac ttc gag gga gcc gaa     1008
Phe Leu Thr Phe Val Phe Val Leu Ser His Asn Phe Glu Gly Ala Glu
                325                 330                 335

cgg acc cca gag aag aac tgc aag gcc aaa cga gct aag gaa ggc aag     1056
Arg Thr Pro Glu Lys Asn Cys Lys Ala Lys Arg Ala Lys Glu Gly Lys
            340                 345                 350

gag gtc aga gac gtg gaa gag gat cga gtc gac tgg tac cga gca cag     1104
Glu Val Arg Asp Val Glu Glu Asp Arg Val Asp Trp Tyr Arg Ala Gln
        355                 360                 365

gcc gag act gct gcc acc tac ggt ggc agc gtg gga atg atg ctt aca     1152
Ala Glu Thr Ala Ala Thr Tyr Gly Gly Ser Val Gly Met Met Leu Thr
    370                 375                 380

ggc ggt ctc aac ctg cag atc gag cat cac ttg ttt ccc cga atg tcc     1200
Gly Gly Leu Asn Leu Gln Ile Glu His His Leu Phe Pro Arg Met Ser
385                 390                 395                 400

tct tgg cac tat ccc ttc att caa gac acc gtt cgg gag tgt tgc aag     1248
Ser Trp His Tyr Pro Phe Ile Gln Asp Thr Val Arg Glu Cys Cys Lys
                405                 410                 415

cga cat ggc gtc cgt tac aca tac tat cct acc att ctc gag aac atc     1296
Arg His Gly Val Arg Tyr Thr Tyr Tyr Pro Thr Ile Leu Glu Asn Ile
            420                 425                 430

atg tcc act ctt cga tac atg cag aag gtg ggt gtt gct cac acc att     1344
Met Ser Thr Leu Arg Tyr Met Gln Lys Val Gly Val Ala His Thr Ile
        435                 440                 445

cag gat gcc cag gag ttc                                             1362
Gln Asp Ala Gln Glu Phe
    450


<210> SEQ ID NO 26
<211> LENGTH: 454
<212> TYPE: PRT
<213> ORGANISM: Artificial Sequence
<220> FEATURE:
<223> OTHER INFORMATION: Synthetic Construct

<400> SEQUENCE: 26

Met Ala Thr Ile Ser Leu Thr Thr Glu Gln Leu Leu Glu His Pro Glu
1               5                   10                  15

Leu Val Ala Ile Asp Gly Val Leu Tyr Asp Leu Phe Gly Leu Ala Lys
            20                  25                  30

Val His Pro Gly Gly Asn Leu Ile Glu Ala Ala Gly Ala Ser Asp Gly
        35                  40                  45

Thr Ala Leu Phe Tyr Ser Met His Pro Gly Val Lys Pro Glu Asn Ser
    50                  55                  60
```

```
Lys Leu Leu Gln Gln Phe Ala Arg Gly Lys His Glu Arg Ser Ser Lys
65                  70                  75                  80

Asp Pro Val Tyr Thr Phe Asp Ser Pro Phe Ala Gln Asp Val Lys Gln
                85                  90                  95

Ser Val Arg Glu Val Met Lys Gly Arg Asn Trp Tyr Ala Thr Pro Gly
            100                 105                 110

Phe Trp Leu Arg Thr Ala Leu Ile Ile Ala Cys Thr Ala Ile Gly Glu
        115                 120                 125

Trp Tyr Trp Ile Thr Thr Gly Ala Val Met Trp Gly Ile Phe Thr Gly
    130                 135                 140

Tyr Phe His Ser Gln Ile Gly Leu Ala Ile Gln His Asp Ala Ser His
145                 150                 155                 160

Gly Ala Ile Ser Lys Lys Pro Trp Val Asn Ala Phe Phe Ala Tyr Gly
                165                 170                 175

Ile Asp Ala Ile Gly Ser Ser Arg Trp Ile Trp Leu Gln Ser His Ile
            180                 185                 190

Met Arg His His Thr Tyr Thr Asn Gln His Gly Leu Asp Leu Asp Ala
        195                 200                 205

Ala Ser Ala Glu Pro Phe Ile Leu Phe His Ser Tyr Pro Ala Thr Asn
    210                 215                 220

Ala Ser Arg Lys Trp Tyr His Arg Phe Gln Ala Trp Tyr Met Tyr Ile
225                 230                 235                 240

Val Leu Gly Met Tyr Gly Val Ser Met Val Tyr Asn Pro Met Tyr Leu
                245                 250                 255

Phe Thr Met Gln His Asn Asp Thr Ile Pro Glu Ala Thr Ser Leu Arg
            260                 265                 270

Pro Gly Ser Phe Phe Asn Arg Gln Arg Ala Phe Ala Val Ser Leu Arg
        275                 280                 285

Leu Leu Phe Ile Phe Arg Asn Ala Phe Leu Pro Trp Tyr Ile Ala Gly
    290                 295                 300

Ala Ser Pro Leu Leu Thr Ile Leu Leu Val Pro Thr Val Thr Gly Ile
305                 310                 315                 320

Phe Leu Thr Phe Val Phe Val Leu Ser His Asn Phe Glu Gly Ala Glu
                325                 330                 335

Arg Thr Pro Glu Lys Asn Cys Lys Ala Lys Arg Ala Lys Glu Gly Lys
            340                 345                 350

Glu Val Arg Asp Val Glu Glu Asp Arg Val Asp Trp Tyr Arg Ala Gln
        355                 360                 365

Ala Glu Thr Ala Ala Thr Tyr Gly Gly Ser Val Gly Met Met Leu Thr
    370                 375                 380

Gly Gly Leu Asn Leu Gln Ile Glu His His Leu Phe Pro Arg Met Ser
385                 390                 395                 400

Ser Trp His Tyr Pro Phe Ile Gln Asp Thr Val Arg Glu Cys Cys Lys
                405                 410                 415

Arg His Gly Val Arg Tyr Thr Tyr Tyr Pro Thr Ile Leu Glu Asn Ile
            420                 425                 430

Met Ser Thr Leu Arg Tyr Met Gln Lys Val Gly Val Ala His Thr Ile
        435                 440                 445

Gln Asp Ala Gln Glu Phe
    450
```

<210> SEQ ID NO 27
<211> LENGTH: 3983
<212> TYPE: DNA

<213> ORGANISM: Artificial Sequence
<220> FEATURE:
<223> OTHER INFORMATION: plasmid pEaD5S

<400> SEQUENCE: 27
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acctcgcgaa 420
tgcatctaga tccatggtca agcgacccgc tctgcctctc accgtggacg gtgtcaccta 480
cgacgtttct gcctggctca accaccatcc cggaggtgcc gacattatcg agaactaccg 540
aggtcgggat gctaccgacg tcttcatggt tatgcactcc gagaacgccg tgtccaaact 600
cagacgaatg cccatcatgg aaccttcctc tcccctgact ccaacacctc ccaagccaaa 660
ctccgacgaa cctcaggagg atttccgaaa gctgcgagac gagctcattg ctgcaggcat 720
gttcgatgcc tctcccatgt ggtacgctta caagaccctg tcgactctcg gactgggtgt 780
ccttgccgtg ctgttgatga cccagtggca ctggtacctg gttggtgcta tcgtcctcgg 840
cattcacttt caacagatgg gatggctctc gcacgacatt tgccatcacc agctgttcaa 900
ggaccgatcc atcaacaatg ccattggcct gctcttcgga aacgtgcttc agggcttttc 960
tgtcacttgg tggaaggacc gacacaacgc tcatcactcc gccaccaacg tgcagggtca 1020
cgatcccgac atcgacaacc tgcctctcct ggcgtggtcc aaggaggacg tcgagcgagc 1080
tggcccgttt tctcgacgga tgatcaagta ccaacagtat tacttctttt tcatctgtgc 1140
ccttctgcga ttcatctggt gctttcagtc cattcatact gccacgggtc tcaaggatcg 1200
aagcaatcag tactatcgaa gacagtacga gaaggagtcc gtcggtctgg cactccactg 1260
gggtctcaag gccttgttct actatttcta catgccctcg tttctcaccg gactcatggt 1320
gttctttgtc tccgagctgc ttggtggctt cggaattgcc atcgttgtct tcatgaacca 1380
ctaccctctg gagaagattc aggactccgt gtgggatggt catggcttct gtgctggaca 1440
gattcacgag accatgaacg ttcagcgagg cctcgtcaca gactggtttt tcggtggcct 1500
caactaccag atcgaacatc acctgtggcc tactcttccc agacacaacc tcaccgctgc 1560
ctccatcaaa gtggagcagc tgtgcaagaa gcacaacctg ccctaccgat ctcctcccat 1620
gctcgaaggt gtcggcattc ttatctccta cctgggcacc ttcgctcgaa tggttgccaa 1680
ggcagacaag gcctaagcgg ccgcatcgga tcccgggccc gtcgactgca gaggcctgca 1740
tgcaagcttg gcgtaatcat ggtcatagct gtttcctgtg tgaaattgtt atccgctcac 1800
aattccacac aacatacgag ccggaagcat aaagtgtaaa gcctggggtg cctaatgagt 1860
gagctaactc acattaattg cgttgcgctc actgcccgct ttccagtcgg gaaacctgtc 1920
gtgccagctg cattaatgaa tcggccaacg cgcggggaga ggcggtttgc gtattgggcg 1980
ctcttccgct tcctcgctca ctgactcgct gcgctcggtc gttcggctgc ggcgagcggt 2040
atcagctcac tcaaaggcgg taatacggtt atccacagaa tcaggggata acgcaggaaa 2100
gaacatgtga gcaaaaggcc agcaaaaggc caggaaccgt aaaaaggccg cgttgctggc 2160
gtttttccat aggctccgcc cccctgacga gcatcacaaa aatcgacgct caagtcagag 2220

-continued gtggcgaaac ccgacaggac tataaagata ccaggcgttt ccccctggaa gctccctcgt 2280
gcgctctcct gttccgaccc tgccgcttac cggatacctg tccgcctttc tcccttcggg 2340
aagcgtggcg ctttctcata gctcacgctg taggtatctc agttcggtgt aggtcgttcg 2400
ctccaagctg ggctgtgtgc acgaaccccc cgttcagccc gaccgctgcg ccttatccgg 2460
taactatcgt cttgagtcca acccggtaag acacgactta tcgccactgg cagcagccac 2520
tggtaacagg attagcagag cgaggtatgt aggcggtgct acagagttct tgaagtggtg 2580
gcctaactac ggctacacta gaagaacagt atttggtatc tgcgctctgc tgaagccagt 2640
taccttcgga aaaagagttg gtagctcttg atccggcaaa caaaccaccg ctggtagcgg 2700
tggttttttt gtttgcaagc agcagattac gcgcagaaaa aaaggatctc aagaagatcc 2760
tttgatcttt tctacggggt ctgacgctca gtggaacgaa aactcacgtt aagggatttt 2820
ggtcatgaga ttatcaaaaa ggatcttcac ctagatcctt ttaaattaaa aatgaagttt 2880
taaatcaatc taaagtatat atgagtaaac ttggtctgac agttaccaat gcttaatcag 2940
tgaggcacct atctcagcga tctgtctatt tcgttcatcc atagttgcct gactccccgt 3000
cgtgtagata actacgatac gggagggctt accatctggc cccagtgctg caatgatacc 3060
gcgagaccca cgctcaccgg ctccagattt atcagcaata aaccagccag ccggaagggc 3120
cgagcgcaga agtggtcctg caactttatc cgcctccatc cagtctatta attgttgccg 3180
ggaagctaga gtaagtagtt cgccagttaa tagtttgcgc aacgttgttg ccattgctac 3240
aggcatcgtg gtgtcacgct cgtcgtttgg tatggcttca ttcagctccg gttcccaacg 3300
atcaaggcga gttacatgat cccccatgtt gtgcaaaaaa gcggttagct ccttcggtcc 3360
tccgatcgtt gtcagaagta agttggccgc agtgttatca ctcatggtta tggcagcact 3420
gcataattct cttactgtca tgccatccgt aagatgcttt tctgtgactg gtgagtactc 3480
aaccaagtca ttctgagaat agtgtatgcg gcgaccgagt tgctcttgcc cggcgtcaat 3540
acgggataat accgcgccac atagcagaac tttaaaagtg ctcatcattg gaaaacgttc 3600
ttcggggcga aaactctcaa ggatcttacc gctgttgaga tccagttcga tgtaacccac 3660
tcgtgcaccc aactgatctt cagcatcttt tactttcacc agcgtttctg ggtgagcaaa 3720
aacaggaagg caaaatgccg caaaaaaggg aataagggcg acacggaaat gttgaatact 3780
catactcttc ctttttcaat attattgaag catttatcag ggttattgtc tcatgagcgg 3840
atacatattt gaatgtattt agaaaaataa acaaataggg gttccgcgca catttccccg 3900
aaaagtgcca cctgacgtct aagaaaccat tattatcatg acattaacct ataaaaatag 3960
gcgtatcacg aggccctttc gtc 3983

<210> SEQ ID NO 28
<211> LENGTH: 14688
<212> TYPE: DNA
<213> ORGANISM: Artificial Sequence
<220> FEATURE:
<223> OTHER INFORMATION: Plasmid pZKLeuN-29E3

<400> SEQUENCE: 28
cgattgttgt ctactaacta tcgtacgata acttcgtata gcatacatta tacgaagtta 60
tcgcgtcgac gagtatctgt ctgactcgtc attgccgcct ttggagtacg actccaacta 120
tgagtgtgct tggatcactt tgacgataca ttcttcgttg gaggctgtgg gtctgacagc 180
tgcgttttcg gcgcggttgg ccgacaacaa tatcagctgc aacgtcattg ctggctttca 240
tcatgatcac atttttgtcg gcaaaggcga cgcccagaga gccattgacg ttctttctaa 300

-continued

```
tttggaccga tagccgtata gtccagtcta tctataagtt caactaactc gtaactatta    360
ccataacata tacttcactg ccccagataa ggttccgata aaaagttctg cagactaaat    420
ttatttcagt ctcctcttca ccaccaaaat gccctcctac gaagctcgag ctaacgtcca    480
caagtccgcc tttgccgctc gagtgctcaa gctcgtggca gccaagaaaa ccaacctgtg    540
tgcttctctg gatgttacca ccaccaagga gctcattgag cttgccgata aggtcggacc    600
ttatgtgtgc atgatcaaaa cccatatcga catcattgac gacttcacct acgccggcac    660
tgtgctcccc ctcaaggaac ttgctcttaa gcacggtttc ttcctgttcg aggacagaaa    720
gttcgcagat attggcaaca ctgtcaagca ccagtaccgg tgtcaccgaa tcgccgagtg    780
gtccgatatc accaacgccc acggtgtacc cggaaccgga atcattgctg gcctgcgagc    840
tggtgccgag gaaactgtct ctgaacagaa gaaggaggac gtctctgact acgagaactc    900
ccagtacaag gagttcctag tcccctctcc caacgagaag ctggccagag gtctgctcat    960
gctggccgag ctgtcttgca agggctctct ggccactggc gagtactcca agcagaccat   1020
tgagcttgcc cgatccgacc ccgagtttgt ggttggcttc attgcccaga accgacctaa   1080
gggcgactct gaggactggc ttattctgac ccccggggtg ggtcttgacg acaagggaga   1140
cgctctcgga cagcagtacc gaactgttga ggatgtcatg tctaccggaa cggatatcat   1200
aattgtcggc cgaggtctgt acggccagaa ccgagatcct attgaggagg ccaagcgata   1260
ccagaaggct ggctgggagg cttaccagaa gattaactgt tagaggttag actatggata   1320
tgtaatttaa ctgtgtatat agagagcgtg caagtatgga gcgcttgttc agcttgtatg   1380
atggtcagac gacctgtctg atcgagtatg tatgatactg cacaacctgt gtatccgcat   1440
gatctgtcca atggggcatg ttgttgtgtt tctcgatacg gagatgctgg gtacagtgct   1500
aatacgttga actacttata cttatatgag gctcgaagaa agctgacttg tgtatgactt   1560
attctcaact acatccccag tcacaatacc accactgcac taccactaca ccaaaaccat   1620
gatcaaacca cccatggact tcctggaggc agaagaactt gttatggaaa agctcaagag   1680
agagatcata acttcgtata gcatacatta tacgaagtta tcctgcaggt aaaggaattc   1740
tggagtttct gagagaaaaa ggcaagatac gtatgtaaca aagcgacgca tggtacaata   1800
ataccggagg catgtatcat agagagttag tggttcgatg atggcactgg tgcctggtat   1860
gactttatac ggctgactac atatttgtcc tcagacatac aattacagtc aagcacttac   1920
ccttggacat ctgtaggtac cccccggcca agacgatctc agcgtgtcgt atgtcggatt   1980
ggcgtagctc cctcgctcgt caattggctc ccatctactt tcttctgctt ggctacaccc   2040
agcatgtctg ctatggctcg ttttcgtgcc ttatctatcc tcccagtatt accaactcta   2100
aatgacatga tgtgattggg tctacacttt catatcagag ataaggagta gcacagttgc   2160
ataaaaagcc caactctaat cagcttcttc ctttcttgta attagtacaa aggtgattag   2220
cgaaatctgg aagcttagtt ggccctaaaa aatcaaaaa aagcaaaaaa cgaaaaacga   2280
aaaaccacag ttttgagaac agggaggtaa cgaaggatcg tatatatata tatatatata   2340
tatacccacg gatcccgaga ccggcctttg attcttccct acaaccaacc attctcacca   2400
ccctaattca caaccatgga gtctggaccc atgcctgctg gcattccctt ccctgagtac   2460
tatgacttct ttatggactg gaagactccc ctggccatcg ctgccaccta cactgctgcc   2520
gtcggtctct tcaaccccaa ggttggcaag gtctcccgag tggttgccaa gtcggctaac   2580
gcaaagcctg ccgagcgaac ccagtccgga gctgccatga ctgccttcgt ctttgtgcac   2640
aacctcattc tgtgtgtcta ctctggcatc accttctact acatgtttcc tgctatggtc   2700
```

-continued

```
aagaacttcc gaacccacac actgcacgaa gcctactgcg acacggatca gtccctctgg   2760
aacaacgcac ttggctactg ggttacctc ttctacctgt ccaagttcta cgaggtcatt   2820
gacaccatca tcatcatcct gaagggacga cggtcctcgc tgcttcagac ctaccaccat   2880
gctggagcca tgattaccat gtggtctggc atcaactacc aagccactcc catttggatc   2940
tttgtggtct tcaactcctt cattcacacc atcatgtact gttactatgc cttcacctct   3000
atcggattcc atcctcctgg caaaaagtac ctgacttcga tgcagattac tcagtttctg   3060
gtcggtatca ccattgccgt gtcctacctc ttcgttcctg gctgcatccg aacacccggt   3120
gctcagatgg ctgtctggat caacgtcggc tacctgtttc ccttgaccta tctgttcgtg   3180
gactttgcca agcgaaccta ctccaagcga tctgccattg ccgctcagaa aaaggctcag   3240
taagcggccg cattgatgat tggaaacaca cacatgggtt atatctaggt gagagttagt   3300
tggacagtta tatattaaat cagctatgcc aacggtaact tcattcatgt caacgaggaa   3360
ccagtgactg caagtaatat agaatttgac caccttgcca ttctcttgca ctcctttact   3420
atatctcatt tatttcttat atacaaatca cttcttcttc ccagcatcga gctcggaaac   3480
ctcatgagca ataacatcgt ggatctcgtc aatagagggc tttttggact ccttgctgtt   3540
ggccaccttg tccttgctgt ctggctcatt ctgtttcaac gccttttaat taacggagta   3600
ggtctcggtg tcggaagcga cgccagatcc gtcatcctcc tttcgctctc caaagtagat   3660
acctccgacg agctctcgga caatgatgaa gtcggtgccc tcaacgtttc ggatggggga   3720
gagatcggcg agcttgggcg acagcagctg gcagggtcgc aggttggcgt acaggttcag   3780
gtcctttcgc agcttgagga gaccctgctc gggtcgcacg tcggttcgtc cgtcgggagt   3840
ggtccatacg gtgttggcag cgcctccgac agcaccgagc ataatagagt cagcctttcg   3900
gcagatgtcg agagtagcgt cggtgatggg ctcgccctcc ttctcaatgg cagctcctcc   3960
aatgagtcgg tcctcaaaca caaactcggt gccggaggcc tcagcaacag acttgagcac   4020
cttgacggcc tcggcaatca cctcggggcc acagaagtcg ccgccgagaa gaacaatctt   4080
cttggagtca gtcttggtct tcttagtttc gggttccatt gtggatgtgt gtggttgtat   4140
gtgtgatgtg gtgtgtggag tgaaaatctg tggctggcaa acgctcttgt atatatacgc   4200
acttttgccc gtgctatgtg gaagactaaa cctccgaaga ttgtgactca ggtagtgcgg   4260
tatcggctag ggacccaaac cttgtcgatg ccgatagcat gcgacgtcgg gcccaattcg   4320
ccctatagtg agtcgtatta caattcactg gccgtcgttt tacaacgtcg tgactgggaa   4380
aaccctggcg ttacccaact taatcgcctt gcagcacatc ccccttttcgc cagctggcgt   4440
aatagcgaag aggcccgcac cgatcgccct tcccaacagt tgcgcagcct gaatggcgaa   4500
tggacgcgcc ctgtagcggc gcattaagcg cggcgggtgt ggtggttacg cgcagcgtga   4560
ccgctacact tgccagcgcc ctagcgcccg ctcctttcgc tttcttccct tcctttctcg   4620
ccacgttcgc cggctttccc cgtcaagctc taaatcgggg gctcccttta gggttccgat   4680
ttagtgcttt acggcacctc gaccccaaaa aacttgatta gggtgatggt tcacgtagtg   4740
ggccatcgcc ctgatagacg gtttttcgcc ctttgacgtt ggagtccacg ttctttaata   4800
gtggactctt gttccaaact ggaacaacac tcaaccctat ctcggtctat tcttttgatt   4860
tataagggat tttgccgatt tcggcctatt ggttaaaaaa tgagctgatt taacaaaaat   4920
ttaacgcgaa ttttaacaaa atattaacgc ttacaatttc ctgatgcggt attttctcct   4980
tacgcatctg tgcggtattt cacaccgcat caggtggcac ttttcgggga aatgtgcgcg   5040
gaacccctat ttgtttattt ttctaaatac attcaaatat gtatccgctc atgagacaat   5100
```

-continued

```
aaccctgata aatgcttcaa taatattgaa aaaggaagag tatgagtatt caacatttcc   5160
gtgtcgccct tattcccttt tttgcggcat tttgccttcc tgtttttgct cacccagaaa   5220
cgctggtgaa agtaaaagat gctgaagatc agttgggtgc acgagtgggt tacatcgaac   5280
tggatctcaa cagcggtaag atccttgaga gttttcgccc cgaagaacgt tttccaatga   5340
tgagcacttt taaagttctg ctatgtggcg cggtattatc ccgtattgac gccgggcaag   5400
agcaactcgg tcgccgcata cactattctc agaatgactt ggttgagtac tcaccagtca   5460
cagaaaagca tcttacggat ggcatgacag taagagaatt atgcagtgct gccataacca   5520
tgagtgataa cactgcggcc aacttacttc tgacaacgat cggaggaccg aaggagctaa   5580
ccgctttttt gcacaacatg ggggatcatg taactcgcct tgatcgttgg gaaccggagc   5640
tgaatgaagc cataccaaac gacgagcgtg acaccacgat gcctgtagca atggcaacaa   5700
cgttgcgcaa actattaact ggcgaactac ttactctagc ttcccggcaa caattaatag   5760
actggatgga ggcggataaa gttgcaggac cacttctgcg ctcggccctt ccggctggct   5820
ggtttattgc tgataaatct ggagccggtg agcgtgggtc tcgcggtatc attgcagcac   5880
tggggccaga tggtaagccc tcccgtatcg tagttatcta cacgacgggg agtcaggcaa   5940
ctatggatga acgaaataga cagatcgctg agataggtgc ctcactgatt aagcattggt   6000
aactgtcaga ccaagtttac tcatatatac tttagattga tttaaaactt catttttaat   6060
ttaaaaggat ctaggtgaag atcctttttg ataatctcat gaccaaaatc ccttaacgtg   6120
agttttcgtt ccactgagcg tcagaccccg tagaaaagat caaaggatct tcttgagatc   6180
cttttttct gcgcgtaatc tgctgcttgc aaacaaaaaa accaccgcta ccagcggtgg   6240
tttgtttgcc ggatcaagag ctaccaactc tttttccgaa ggtaactggc ttcagcagag   6300
cgcagatacc aaatactgtt cttctagtgt agccgtagtt aggccaccac ttcaagaact   6360
ctgtagcacc gcctacatac ctcgctctgc taatcctgtt accagtggct gctgccagtg   6420
gcgataagtc gtgtcttacc gggttggact caagacgata gttaccggat aaggcgcagc   6480
ggtcgggctg aacggggggt tcgtgcacac agcccagctt ggagcgaacg acctacaccg   6540
aactgagata cctacagcgt gagctatgag aaagcgccac gcttcccgaa gggagaaagg   6600
cggacaggta tccggtaagc ggcagggtcg gaacaggaga gcgcacgagg gagcttccag   6660
ggggaaacgc ctggtatctt tatagtcctg tcgggtttcg ccacctctga cttgagcgtc   6720
gatttttgtg atgctcgtca ggggggcgga gcctatggaa aaacgccagc aacgcggcct   6780
ttttacggtt cctggccttt tgctggcctt ttgctcacat gttctttcct gcgttatccc   6840
ctgattctgt ggataaccgt attaccgcct ttgagtgagc tgataccgct cgccgcagcc   6900
gaacgaccga gcgcagcgag tcagtgagcg aggaagcgga agagcgccca atacgcaaac   6960
cgcctctccc cgcgcgttgg ccgattcatt aatgcagctg gcgcgcccac tgagctcgtc   7020
taacggactt gatatacaac caattaaaac aaatgaaaag aaatacagtt ctttgtatca   7080
tttgtaacaa ttaccctgta caaactaagg tattgaaatc ccacaatatt cccaaagtcc   7140
acccctttcc aaattgtcat gcctacaact catataccaa gcactaacct accaaacacc   7200
actaaaaccc cacaaaatat atcttaccga atatacagta acaagctacc accacactcg   7260
ttgggtgcag tcgccagctt aaagatatct atccacatca gccacaactc ccttccttta   7320
ataaaccgac tacacccttg gctattgagg ttatgagtga atatactgta gacaagacac   7380
tttcaagaag actgtttcca aaacgtacca ctgtcctcca ctacaaacac acccaatctg   7440
cttcttctag tcaaggttgc tacaccggta aattataaat catcatttca ttagcagggc   7500
```

-continued

```
agggcccttt ttatagagtc ttatacacta gcggaccctg ccggtagacc aacccgcagg   7560
cgcgtcagtt tgctccttcc atcaatgcgt cgtagaaacg acttactcct tcttgagcag   7620
ctccttgacc ttgttggcaa caagtctccg acctcggagg tggaggaaga gcctccgata   7680
tcggcggtag tgataccagc ctcgacggac tccttgacgg cagcctcaac agcgtcaccg   7740
gcgggcttca tgttaagaga gaacttgagc atcatggcgg cagacagaat ggtggcgtac   7800
gcaactaaca tgaatgaata cgatatacat caaagactat gatacgcagt attgcacact   7860
gtacgagtaa gagcactagc cactgcactc aagtgaaacc gttgcccggg tacgagtatg   7920
agtatgtaca gtatgtttag tattgtactt ggacagtgct tgtatcgtac attctcaagt   7980
gtcaaacata aatatccgtt gctatatcct cgcaccacca cgtagctcgc tatatccctg   8040
tgttgaatcc atccatcttg gattgccaat tgtgcacaca gaaccgggca ctcacttccc   8100
catccacact tgcggccgct taagcaacgg gcttgataac agcggggggg gtgcccacgt   8160
tgttgcggtt gcggaagaac agaacaccct taccagcacc ctcggcacca gcgctgggct   8220
caacccactg gcacatacgc gcactgcggt acatggcgcg gatgaagcca cgaggaccat   8280
cctggacatc agcccggtag tgcttgccca tgatgggctt aatggcctcg gtggcctcgt   8340
ccgcgttgta gaaggggatg ctgctgacgt agtggtggag gacatgagtc tcgatgatgc   8400
cgtggagaag gtggcggccg atgaagccca tctcacggtc aatggtagca gcggcaccac   8460
ggacgaagtt ccactcgtcg ttggtgtagt ggggaagggt agggtcggtg tgctggagga   8520
aggtgatggc aacgagccag tggttaaccc agaggtaggg aacaaagtac cagatggcca   8580
tgttgtagaa accgaacttc tgaacgagga agtacagagc agtggccatc agaccgatac   8640
caatatcgct gaggacgatg agcttagcgt cactgttctc gtacagaggg ctgcggggat   8700
cgaagtggtt aacaccaccg ccgaggccgt tatgcttgcc cttgccgcga ccctcacgct   8760
ggcgctcgtg gtagttgtgg ccggtaacat tggtgatgag gtagttgggc cagccaacga   8820
gctgctgaag gacgagcatg agaagagtga aagcgggggt ctcctcagta agatgagcga   8880
gctcgtgggt catctttccg agacgagtag cctgctgctc gcgggttcgg ggaacgaaga   8940
ccatgtcacg ctccatgttg ccagtggcct tgtggtgctt tcggtgggag atttgccagc   9000
tgaagtaggg gacaaggagg gaagagtgaa gaacccagcc agtaatgtcg ttgatgatgc   9060
gagaatcgga gaaagcaccg tgaccgcact catgggcaat aacccagaga ccagtaccga   9120
aaagaccctg aagaacggtg tacacggccc acagaccagc gcgggcgggg gtggagggga   9180
tatattcggg ggtcacaaag ttgtaccaga tgctgaaagt ggtagtcagg aggacaatgt   9240
cgcggaggat ataaccgtat cccttgagag cggagcgctt gaagcagtgc ttagggatgg   9300
cattgtagat gtccttgatg gtaaagtcgg gaacctcgaa ctggttgccg taggtgtcga   9360
gcatgacacc atactcggac ttgggcttgg cgatatcaac ctcggacatg gacgagagcg   9420
atgtggaaga ggccgagtgg cggggagagt ctgaaggaga gacggcggca gactcagaat   9480
ccgtcacagt agttgaggtg acggtgcgtc taagcgcagg gttctgcttg ggcagagccg   9540
aagtggacgc catggttgat gtgtgtttaa ttcaagaatg aatatagaga agagaagaag   9600
aaaaaagatt caattgagcc ggcgatgcag acccttatat aaatgttgcc ttggacagac   9660
ggagcaagcc cgcccaaacc tacgttcggt ataatatgtt aagcttttta acacaaaggt   9720
ttggcttggg gtaacctgat gtggtgcaaa agaccgggcg ttggcgagcc attgcgcggg   9780
cgaatggggc cgtgactcgt ctcaaattcg agggcgtgcc tcaattcgtg cccccgtggc   9840
tttttcccgc cgtttccgcc ccgtttgcac cactgcagcc gcttctttgg ttcggacacc   9900
```

-continued

```
ttgctgcgag ctaggtgcct tgtgctactt aaaaagtggc ctcccaacac caacatgaca   9960
tgagtgcgtg ggccaagaca cgttggcggg gtcgcagtcg gctcaatggc ccggaaaaaa  10020
cgctgctgga gctggttcgg acgcagtccg ccgcggcgta tggatatccg caaggttcca  10080
tagcgccatt gccctccgtc ggcgtctatc ccgcaacctc taaatagagc gggaatataa  10140
cccaagcttc tttttttcc tttaacacgc acaccccaa ctatcatgtt gctgctgctg  10200
tttgactcta ctctgtggag gggtgctccc acccaaccca acctacaggt ggatccggcg  10260
ctgtgattgg ctgataagtc tcctatccgg actaattctg accaatggga catgcgcgca  10320
ggacccaaat gccgcaatta cgtaacccca acgaaatgcc taccccctctt tggagcccag  10380
cggccccaaa tccccccaag cagcccggtt ctaccggctt ccatctccaa gcacaagcag  10440
cccggttcta ccggcttcca tctccaagca cccctttctc cacaccccac aaaaagaccc  10500
gtgcaggaca tcctactgcg tcgacatcat ttaaattcct tcacttcaag ttcattcttc  10560
atctgcttct gttttacttt gacaggcaaa tgaagacatg gtacgacttg atggaggcca  10620
agaacgccat ttcaccccga gacaccgaag tgcctgaaat cctggctgcc cccattgata  10680
acatcggaaa ctacggtatt ccggaaagtg tatatagaac ctttccccag cttgtgtctg  10740
tggatatgga tggtgtaatc ccctttgagt actcgtcttg gcttctctcc gagcagtatg  10800
aggctctcta atctagcgca tttaatatct caatgtattt atatatttat cttctcatgc  10860
ggccgctcac tgaatctttt tggctccctt gtgcttcctg acgatatacg tttgcacata  10920
gaaattcaag aacaaacaca agactgtgcc aacataaaag taattgaaga accagccaaa  10980
catcctcatc ccatcttggc gataacaggg aatgttcctg tacttccaga caatgtagaa  11040
accaacattg aattgaatga tctgcattga tgtaatcagg gattttggca tggggaactt  11100
cagcttgatc aatctggtcc aataataacc gtacatgatc cagtggatga aaccattcaa  11160
cagcacaaaa atccaaacag cttcatttcg gtaattatag aacagccaca tatccatcgg  11220
tgcccccaaa tgatggaaga attgcaacca ggtcagaggc ttgcccatca gtggcaaata  11280
gaaggagtca atatactcca ggaacttgct caaatagaac aactgcgtgg tgatcctgaa  11340
gacgttgttg tcaaaagcct tctcgcagtt gtcagacata acaccgatgg tgtacatggc  11400
atatgccatt gagaggaatg atcccaacga ataaatggac atgagaaggt tgtaattggt  11460
gaaaacaaac ttcatacgag actgaccttt tggaccaagg gggccaagag tgaacttcaa  11520
gatgacaaat gcgatggaca agtaaagcac ctcacagtga ctggcatcac tccagagttg  11580
ggcataatca actggttggg taaaacttcc tgcccaattg agactatttc attcaccacc  11640
tccatggcca ttgctgtaga tatgtcttgt gtgtaagggg gttggggtgg ttgtttgtgt  11700
tcttgacttt tgtgttagca agggaagacg ggcaaaaaag tgagtgtggt tgggagggag  11760
agacgagcct tatatataat gcttgtttgt gtttgtgcaa gtggacgccg aaacgggcag  11820
gagccaaact aaacaaggca gacaatgcga gcttaattgg attgcctgat gggcaggggt  11880
tagggctcga tcaatggggg tgcgaagtga caaaattggg aattaggttc gcaagcaagg  11940
ctgacaagac tttggcccaa acatttgtac gcggtggaca acaggagcca cccatcgtct  12000
gtcacgggct agccggtcgt gcgtcctgtc aggctccacc taggctccat gccactccat  12060
acaatcccac tagtgtaccg ctaggccgct tttagctccc atctaagacc cccccaaaac  12120
ctccactgta cagtgcactg tactgtgtgg cgatcaaggg caagggaaaa aaggcgcaaa  12180
catgcacgca tggaatgacg taggtaaggc gttactagac tgaaaagtgg cacatttcgg  12240
cgtgccaaag ggtcctaggt gcgtttcgcg agctgggcgc caggccaagc cgctccaaaa  12300
```

-continued

```
cgcctctccg actccctcca gcggcctcca tatccccatc cctctccaca gcaatgttgt  12360
taagccttgc aaacgaaaaa atagaaaggc taataagctt ccaatattgt ggtgtacgct  12420
gcataacgca acaatgagcg ccaaacaaca cacacacaca gcacacagca gcattaacca  12480
cgatgaacag catgacatta caggtgggtg tgtaatcagg gccctgattg ctggtggtgg  12540
gagcccccat catgggcaga tctgcgtaca ctgtttaaac agtgtacgca gatctactat  12600
agaggaacat ttaaattgcc ccggagaaga cggccaggcc gcctagatga caaattcaac  12660
aactcacagc tgactttctg ccattgccac tagggggggg ccttttata tggccaagcc  12720
aagctctcca cgtcggttgg gctgcaccca acaataaatg ggtagggttg caccaacaaa  12780
gggatgggat ggggggtaga agatacgagg ataacggggc tcaatggcac aaataagaac  12840
gaatactgcc attaagactc gtgatccagc gactgacacc attgcatcat ctaagggcct  12900
caaaactacc tcggaactgc tgcgctgatc tggacaccac agaggttccg agcactttag  12960
gttgcaccaa atgtcccacc aggtgcaggc agaaaacgct ggaacagcgt gtacagtttg  13020
tcttaacaaa aagtgagggc gctgaggtcg agcagggtgg tgtgacttgt tatagccttt  13080
agagctgcga aagcgcgtat ggatttggct catcaggcca gattgagggt ctgtggacac  13140
atgtcatgtt agtgtacttc aatcgccccc tggatatagc cccgacaata ggccgtggcc  13200
tcattttttt gccttccgca catttccatt gctcgatacc cacaccttgc ttctcctgca  13260
cttgccaacc ttaatactgg tttacattga ccaacatctt acaagcgggg ggcttgtcta  13320
gggtatatat aaacagtggc tctcccaatc ggttgccagt ctcttttttc ctttctttcc  13380
ccacagattc gaaatctaaa ctacacatca cagaattccg agccgtgagt atccacgaca  13440
agatcagtgt cgagacgacg cgttttgtgt aatgacacaa tccgaaagtc gctagcaaca  13500
cacactctct acacaaacta acccagctct ggtaccatgg aggtcgtgaa cgaaatcgtc  13560
tccattggcc aggaggttct tcccaaggtc gactatgctc agctctggtc tgatgcctcg  13620
cactgcgagg tgctgtacct ctccatcgcc ttcgtcatcc tgaagttcac ccttggtcct  13680
ctcggaccca agggtcagtc tcgaatgaag tttgtgttca ccaactacaa cctgctcatg  13740
tccatctact cgctgggctc cttcctctct atggcctacg ccatgtacac cattggtgtc  13800
atgtccgaca actgcgagaa ggctttcgac aacaatgtct tccgaatcac cactcagctg  13860
ttctacctca gcaagttcct cgagtacatt gactccttct atctgcccct catgggcaag  13920
cctctgacct ggttgcagtt ctttcaccat ctcggagctc ctatggacat gtggctgttc  13980
tacaactacc gaaacgaagc cgtttggatc tttgtgctgc tcaacggctt cattcactgg  14040
atcatgtacg gctactattg gacccgactg atcaagctca agttccctat gcccaagtcc  14100
ctgattactt ctatgcagat cattcagttc aacgttggct tctacatcgt ctggaagtac  14160
cggaacattc cctgctaccg acaagatgga atgagaatgt ttggctggtt tttcaactac  14220
ttctacgttg gtactgtcct gtgtctgttc ctcaacttct acgtgcagac ctacatcgtc  14280
cgaaagcaca agggagccaa aaagattcag tgagcggccg catgtacata caagattatt  14340
tatagaaatg aatcgcgatc gaacaaagag tacgagtgta cgagtagggg atgatgataa  14400
aagtggaaga agttccgcat ctttggattt atcaacgtgt aggacgatac ttcctgtaaa  14460
aatgcaatgt ctttaccata ggttctgctg tagatgttat taactaccat taacatgtct  14520
acttgtacag ttgcagacca gttggagtat agaatggtac acttaccaaa aagtgttgat  14580
ggttgtaact acgatatata aaactgttga cgggatcccc gctgatatgc ctaaggaaca  14640
atcaaagagg aagatattaa ttcagaatgc tagtatacag ttagggat               14688
```

```
<210> SEQ ID NO 29
<211> LENGTH: 1434
<212> TYPE: DNA
<213> ORGANISM: Fusarium monoliforme
<220> FEATURE:
<221> NAME/KEY: CDS
<222> LOCATION: (1)..(1434)
<223> OTHER INFORMATION: delta-12 desaturase
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: WO 2005/047485
<311> PATENT FILING DATE: 2004-11-12
<312> PUBLICATION DATE: 2005-05-26
<313> RELEVANT RESIDUES IN SEQ ID NO: (1)..(1434)
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: US 2005-0216975-A1
<311> PATENT FILING DATE: 2004-11-10
<312> PUBLICATION DATE: 2005-09-29
<313> RELEVANT RESIDUES IN SEQ ID NO: (1)..(1434)

<400> SEQUENCE: 29

atg gcg tcc act tcg gct ctg ccc aag cag aac cct gcg ctt aga cgc       48
Met Ala Ser Thr Ser Ala Leu Pro Lys Gln Asn Pro Ala Leu Arg Arg
1               5                   10                  15

acc gtc acc tca act act gtg acg gat tct gag tct gcc gcc gtc tct       96
Thr Val Thr Ser Thr Thr Val Thr Asp Ser Glu Ser Ala Ala Val Ser
            20                  25                  30

cct tca gac tct ccc cgc cac tcg gcc tct tcc aca tcg ctc tcg tcc      144
Pro Ser Asp Ser Pro Arg His Ser Ala Ser Ser Thr Ser Leu Ser Ser
        35                  40                  45

atg tcc gag gtt gat atc gcc aag ccc aag tcc gag tat ggt gtc atg      192
Met Ser Glu Val Asp Ile Ala Lys Pro Lys Ser Glu Tyr Gly Val Met
    50                  55                  60

ctc gac acc tac ggc aac cag ttc gag gtt ccc gac ttt acc atc aag      240
Leu Asp Thr Tyr Gly Asn Gln Phe Glu Val Pro Asp Phe Thr Ile Lys
65                  70                  75                  80

gac atc tac aat gcc atc cct aag cac tgc ttc aag cgc tcc gct ctc      288
Asp Ile Tyr Asn Ala Ile Pro Lys His Cys Phe Lys Arg Ser Ala Leu
                85                  90                  95

aag gga tac ggt tat atc ctc cgc gac att gtc ctc ctg act acc act      336
Lys Gly Tyr Gly Tyr Ile Leu Arg Asp Ile Val Leu Leu Thr Thr Thr
            100                 105                 110

ttc agc atc tgg tac aac ttt gtg acc ccc gaa tat atc ccc tcc acc      384
Phe Ser Ile Trp Tyr Asn Phe Val Thr Pro Glu Tyr Ile Pro Ser Thr
        115                 120                 125

ccc gcc cgc gct ggt ctg tgg gcc gtg tac acc gtt ctt cag ggt ctt      432
Pro Ala Arg Ala Gly Leu Trp Ala Val Tyr Thr Val Leu Gln Gly Leu
    130                 135                 140

ttc ggt act ggt ctc tgg gtt att gcc cat gag tgc ggt cac ggt gct      480
Phe Gly Thr Gly Leu Trp Val Ile Ala His Glu Cys Gly His Gly Ala
145                 150                 155                 160

ttc tcc gat tct cgc atc atc aac gac att act ggc tgg gtt ctt cac      528
Phe Ser Asp Ser Arg Ile Ile Asn Asp Ile Thr Gly Trp Val Leu His
                165                 170                 175

tct tcc ctc ctt gtc ccc tac ttc agc tgg caa atc tcc cac cga aag      576
Ser Ser Leu Leu Val Pro Tyr Phe Ser Trp Gln Ile Ser His Arg Lys
            180                 185                 190

cac cac aag gcc act ggc aac atg gag cgt gac atg gtc ttc gtt ccc      624
His His Lys Ala Thr Gly Asn Met Glu Arg Asp Met Val Phe Val Pro
        195                 200                 205

cga acc cgc gag cag cag gct act cgt ctc gga aag atg acc cac gag      672
Arg Thr Arg Glu Gln Gln Ala Thr Arg Leu Gly Lys Met Thr His Glu
```

-continued

```
    210                 215                 220

ctc gct cat ctt act gag gag acc ccc gct ttc act ctt ctc atg ctc      720
Leu Ala His Leu Thr Glu Glu Thr Pro Ala Phe Thr Leu Leu Met Leu
225                 230                 235                 240

gtc ctt cag cag ctc gtt ggc tgg ccc aac tac ctc atc acc aat gtt      768
Val Leu Gln Gln Leu Val Gly Trp Pro Asn Tyr Leu Ile Thr Asn Val
                245                 250                 255

acc ggc cac aac tac cac gag cgc cag cgt gag ggt cgc ggc aag ggc      816
Thr Gly His Asn Tyr His Glu Arg Gln Arg Glu Gly Arg Gly Lys Gly
            260                 265                 270

aag cat aac ggc ctc ggc ggt ggt gtt aac cac ttc gat ccc cgc agc      864
Lys His Asn Gly Leu Gly Gly Gly Val Asn His Phe Asp Pro Arg Ser
        275                 280                 285

cct ctg tac gag aac agt gac gct aag ctc atc gtc ctc agc gat att      912
Pro Leu Tyr Glu Asn Ser Asp Ala Lys Leu Ile Val Leu Ser Asp Ile
    290                 295                 300

ggt atc ggt ctg atg gcc act gct ctg tac ttc ctc gtt cag aag ttc      960
Gly Ile Gly Leu Met Ala Thr Ala Leu Tyr Phe Leu Val Gln Lys Phe
305                 310                 315                 320

ggt ttc tac aac atg gcc atc tgg tac ttt gtt ccc tac ctc tgg gtt     1008
Gly Phe Tyr Asn Met Ala Ile Trp Tyr Phe Val Pro Tyr Leu Trp Val
                325                 330                 335

aac cac tgg ctc gtt gcc atc acc ttc ctc cag cac acc gac cct acc     1056
Asn His Trp Leu Val Ala Ile Thr Phe Leu Gln His Thr Asp Pro Thr
            340                 345                 350

ctt ccc cac tac acc aac gac gag tgg aac ttc gtc cgt ggt gcc gct     1104
Leu Pro His Tyr Thr Asn Asp Glu Trp Asn Phe Val Arg Gly Ala Ala
        355                 360                 365

gct acc att gac cgt gag atg ggc ttc atc ggc cgc cac ctt ctc cac     1152
Ala Thr Ile Asp Arg Glu Met Gly Phe Ile Gly Arg His Leu Leu His
    370                 375                 380

ggc atc atc gag act cat gtc ctc cac cac tac gtc agc agc atc ccc     1200
Gly Ile Ile Glu Thr His Val Leu His His Tyr Val Ser Ser Ile Pro
385                 390                 395                 400

ttc tac aac gcg gac gag gcc acc gag gcc att aag ccc atc atg ggc     1248
Phe Tyr Asn Ala Asp Glu Ala Thr Glu Ala Ile Lys Pro Ile Met Gly
                405                 410                 415

aag cac tac cgg gct gat gtc cag gat ggt cct cgt ggc ttc atc cgc     1296
Lys His Tyr Arg Ala Asp Val Gln Asp Gly Pro Arg Gly Phe Ile Arg
            420                 425                 430

gcc atg tac cgc agt gcg cgt atg tgc cag tgg gtt gag ccc agc gct     1344
Ala Met Tyr Arg Ser Ala Arg Met Cys Gln Trp Val Glu Pro Ser Ala
        435                 440                 445

ggt gcc gag ggt gct ggt aag ggt gtt ctg ttc ttc cgc aac cgc aac     1392
Gly Ala Glu Gly Ala Gly Lys Gly Val Leu Phe Phe Arg Asn Arg Asn
    450                 455                 460

aac gtg ggc acc ccc ccc gct gtt atc aag ccc gtt gct taa             1434
Asn Val Gly Thr Pro Pro Ala Val Ile Lys Pro Val Ala
465                 470                 475


<210> SEQ ID NO 30
<211> LENGTH: 477
<212> TYPE: PRT
<213> ORGANISM: Fusarium monoliforme

<400> SEQUENCE: 30

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30
```

-continued

```
Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460
```

```
Asn Val Gly Thr Pro Pro Ala Val Ile Lys Pro Val Ala
465                 470                 475


<210> SEQ ID NO 31
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: synthetic delta-9 elongase (codon-optimized
      for Yarrowia lipolytica)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(777)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US-2007-0117190-A1
<311> PATENT FILING DATE: 2006-11-16
<312> PUBLICATION DATE: 2007-05-24
<313> RELEVANT RESIDUES IN SEQ ID NO: (1)..(777)

<400> SEQUENCE: 31

atg gag gtc gtg aac gaa atc gtc tcc att ggc cag gag gtt ctt ccc       48
Met Glu Val Val Asn Glu Ile Val Ser Ile Gly Gln Glu Val Leu Pro
1               5                   10                  15

aag gtc gac tat gct cag ctc tgg tct gat gcc tcg cac tgc gag gtg       96
Lys Val Asp Tyr Ala Gln Leu Trp Ser Asp Ala Ser His Cys Glu Val
            20                  25                  30

ctg tac ctc tcc atc gcc ttc gtc atc ctg aag ttc acc ctt ggt cct      144
Leu Tyr Leu Ser Ile Ala Phe Val Ile Leu Lys Phe Thr Leu Gly Pro
        35                  40                  45

ctc gga ccc aag ggt cag tct cga atg aag ttt gtg ttc acc aac tac      192
Leu Gly Pro Lys Gly Gln Ser Arg Met Lys Phe Val Phe Thr Asn Tyr
    50                  55                  60

aac ctg ctc atg tcc atc tac tcg ctg ggc tcc ttc ctc tct atg gcc      240
Asn Leu Leu Met Ser Ile Tyr Ser Leu Gly Ser Phe Leu Ser Met Ala
65                  70                  75                  80

tac gcc atg tac acc att ggt gtc atg tcc gac aac tgc gag aag gct      288
Tyr Ala Met Tyr Thr Ile Gly Val Met Ser Asp Asn Cys Glu Lys Ala
                85                  90                  95

ttc gac aac aat gtc ttc cga atc acc act cag ctg ttc tac ctc agc      336
Phe Asp Asn Asn Val Phe Arg Ile Thr Thr Gln Leu Phe Tyr Leu Ser
            100                 105                 110

aag ttc ctc gag tac att gac tcc ttc tat ctg ccc ctc atg ggc aag      384
Lys Phe Leu Glu Tyr Ile Asp Ser Phe Tyr Leu Pro Leu Met Gly Lys
        115                 120                 125

cct ctg acc tgg ttg cag ttc ttt cac cat ctc gga gct cct atg gac      432
Pro Leu Thr Trp Leu Gln Phe Phe His His Leu Gly Ala Pro Met Asp
    130                 135                 140

atg tgg ctg ttc tac aac tac cga aac gaa gcc gtt tgg atc ttt gtg      480
Met Trp Leu Phe Tyr Asn Tyr Arg Asn Glu Ala Val Trp Ile Phe Val
145                 150                 155                 160

ctg ctc aac ggc ttc att cac tgg atc atg tac ggc tac tat tgg acc      528
Leu Leu Asn Gly Phe Ile His Trp Ile Met Tyr Gly Tyr Tyr Trp Thr
                165                 170                 175

cga ctg atc aag ctc aag ttc cct atg ccc aag tcc ctg att act tct      576
Arg Leu Ile Lys Leu Lys Phe Pro Met Pro Lys Ser Leu Ile Thr Ser
            180                 185                 190

atg cag atc att cag ttc aac gtt ggc ttc tac atc gtc tgg aag tac      624
```

-continued

```
Met Gln Ile Ile Gln Phe Asn Val Gly Phe Tyr Ile Val Trp Lys Tyr
        195                 200                 205

cgg aac att ccc tgc tac cga caa gat gga atg aga atg ttt ggc tgg      672
Arg Asn Ile Pro Cys Tyr Arg Gln Asp Gly Met Arg Met Phe Gly Trp
    210                 215                 220

ttt ttc aac tac ttc tac gtt ggt act gtc ctg tgt ctg ttc ctc aac      720
Phe Phe Asn Tyr Phe Tyr Val Gly Thr Val Leu Cys Leu Phe Leu Asn
225                 230                 235                 240

ttc tac gtg cag acc tac atc gtc cga aag cac aag gga gcc aaa aag      768
Phe Tyr Val Gln Thr Tyr Ile Val Arg Lys His Lys Gly Ala Lys Lys
                245                 250                 255

att cag tga                                                          777
Ile Gln


<210> SEQ ID NO 32
<211> LENGTH: 258
<212> TYPE: PRT
<213> ORGANISM: Euglena gracilis

<400> SEQUENCE: 32

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln


<210> SEQ ID NO 33
<211> LENGTH: 34
<212> TYPE: DNA
```

<213> ORGANISM: Escherichia coli

<400> SEQUENCE: 33
ataacttcgt ataatgtatg ctatacgaag ttat 34

<210> SEQ ID NO 34
<211> LENGTH: 828
<212> TYPE: DNA
<213> ORGANISM: Mortierella alpina
<220> FEATURE:
<221> NAME/KEY: CDS
<222> LOCATION: (1)..(828)
<223> OTHER INFORMATION: synthetic C16/18 elongase (codon-optimized for Yarrowia lipolytica)
<300> PUBLICATION INFORMATION:
<302> TITLE: A MORTIERELLA ALPINA C16/18 FATTY ACID ELONGASE
<310> PATENT DOCUMENT NUMBER: US 2007-0087420-A1
<311> PATENT FILING DATE: 2005-10-19
<312> PUBLICATION DATE: 2007-04-19
<313> RELEVANT RESIDUES IN SEQ ID NO: (1)..(828)
<300> PUBLICATION INFORMATION:
<302> TITLE: A MORTIERELLA ALPINA C16/18 FATTY ACID ELONGASE
<310> PATENT DOCUMENT NUMBER: WO 2007/046817
<311> PATENT FILING DATE: 2005-11-04
<312> PUBLICATION DATE: 2007-04-26
<313> RELEVANT RESIDUES IN SEQ ID NO: (1)..(828)

<400> SEQUENCE: 34

```
atg gag tct gga ccc atg cct gct ggc att ccc ttc cct gag tac tat       48
Met Glu Ser Gly Pro Met Pro Ala Gly Ile Pro Phe Pro Glu Tyr Tyr
1               5                   10                  15

gac ttc ttt atg gac tgg aag act ccc ctg gcc atc gct gcc acc tac       96
Asp Phe Phe Met Asp Trp Lys Thr Pro Leu Ala Ile Ala Ala Thr Tyr
            20                  25                  30

act gct gcc gtc ggt ctc ttc aac ccc aag gtt ggc aag gtc tcc cga      144
Thr Ala Ala Val Gly Leu Phe Asn Pro Lys Val Gly Lys Val Ser Arg
        35                  40                  45

gtg gtt gcc aag tcg gct aac gca aag cct gcc gag cga acc cag tcc      192
Val Val Ala Lys Ser Ala Asn Ala Lys Pro Ala Glu Arg Thr Gln Ser
    50                  55                  60

gga gct gcc atg act gcc ttc gtc ttt gtg cac aac ctc att ctg tgt      240
Gly Ala Ala Met Thr Ala Phe Val Phe Val His Asn Leu Ile Leu Cys
65                  70                  75                  80

gtc tac tct ggc atc acc ttc tac tac atg ttt cct gct atg gtc aag      288
Val Tyr Ser Gly Ile Thr Phe Tyr Tyr Met Phe Pro Ala Met Val Lys
                85                  90                  95

aac ttc cga acc cac aca ctg cac gaa gcc tac tgc gac acg gat cag      336
Asn Phe Arg Thr His Thr Leu His Glu Ala Tyr Cys Asp Thr Asp Gln
            100                 105                 110

tcc ctc tgg aac aac gca ctt ggc tac tgg ggt tac ctc ttc tac ctg      384
Ser Leu Trp Asn Asn Ala Leu Gly Tyr Trp Gly Tyr Leu Phe Tyr Leu
        115                 120                 125

tcc aag ttc tac gag gtc att gac acc atc atc atc atc ctg aag gga      432
Ser Lys Phe Tyr Glu Val Ile Asp Thr Ile Ile Ile Ile Leu Lys Gly
    130                 135                 140

cga cgg tcc tcg ctg ctt cag acc tac cac cat gct gga gcc atg att      480
Arg Arg Ser Ser Leu Leu Gln Thr Tyr His His Ala Gly Ala Met Ile
145                 150                 155                 160

acc atg tgg tct ggc atc aac tac caa gcc act ccc att tgg atc ttt      528
Thr Met Trp Ser Gly Ile Asn Tyr Gln Ala Thr Pro Ile Trp Ile Phe
                165                 170                 175

gtg gtc ttc aac tcc ttc att cac acc atc atg tac tgt tac tat gcc      576
Val Val Phe Asn Ser Phe Ile His Thr Ile Met Tyr Cys Tyr Tyr Ala
            180                 185                 190

ttc acc tct atc gga ttc cat cct cct ggc aaa aag tac ctg act tcg      624
```

-continued

```
Phe Thr Ser Ile Gly Phe His Pro Pro Gly Lys Lys Tyr Leu Thr Ser
        195                 200                 205

atg cag att act cag ttt ctg gtc ggt atc acc att gcc gtg tcc tac      672
Met Gln Ile Thr Gln Phe Leu Val Gly Ile Thr Ile Ala Val Ser Tyr
    210                 215                 220

ctc ttc gtt cct ggc tgc atc cga aca ccc ggt gct cag atg gct gtc      720
Leu Phe Val Pro Gly Cys Ile Arg Thr Pro Gly Ala Gln Met Ala Val
225                 230                 235                 240

tgg atc aac gtc ggc tac ctg ttt ccc ttg acc tat ctg ttc gtg gac      768
Trp Ile Asn Val Gly Tyr Leu Phe Pro Leu Thr Tyr Leu Phe Val Asp
                245                 250                 255

ttt gcc aag cga acc tac tcc aag cga tct gcc att gcc gct cag aaa      816
Phe Ala Lys Arg Thr Tyr Ser Lys Arg Ser Ala Ile Ala Ala Gln Lys
            260                 265                 270

aag gct cag taa                                                      828
Lys Ala Gln
        275


<210> SEQ ID NO 35
<211> LENGTH: 275
<212> TYPE: PRT
<213> ORGANISM: Mortierella alpina

<400> SEQUENCE: 35

Met Glu Ser Gly Pro Met Pro Ala Gly Ile Pro Phe Pro Glu Tyr Tyr
1               5                   10                  15

Asp Phe Phe Met Asp Trp Lys Thr Pro Leu Ala Ile Ala Ala Thr Tyr
            20                  25                  30

Thr Ala Ala Val Gly Leu Phe Asn Pro Lys Val Gly Lys Val Ser Arg
        35                  40                  45

Val Val Ala Lys Ser Ala Asn Ala Lys Pro Ala Glu Arg Thr Gln Ser
    50                  55                  60

Gly Ala Ala Met Thr Ala Phe Val Phe Val His Asn Leu Ile Leu Cys
65                  70                  75                  80

Val Tyr Ser Gly Ile Thr Phe Tyr Tyr Met Phe Pro Ala Met Val Lys
                85                  90                  95

Asn Phe Arg Thr His Thr Leu His Glu Ala Tyr Cys Asp Thr Asp Gln
            100                 105                 110

Ser Leu Trp Asn Asn Ala Leu Gly Tyr Trp Gly Tyr Leu Phe Tyr Leu
        115                 120                 125

Ser Lys Phe Tyr Glu Val Ile Asp Thr Ile Ile Ile Ile Leu Lys Gly
    130                 135                 140

Arg Arg Ser Ser Leu Leu Gln Thr Tyr His His Ala Gly Ala Met Ile
145                 150                 155                 160

Thr Met Trp Ser Gly Ile Asn Tyr Gln Ala Thr Pro Ile Trp Ile Phe
                165                 170                 175

Val Val Phe Asn Ser Phe Ile His Thr Ile Met Tyr Cys Tyr Tyr Ala
            180                 185                 190

Phe Thr Ser Ile Gly Phe His Pro Pro Gly Lys Lys Tyr Leu Thr Ser
        195                 200                 205

Met Gln Ile Thr Gln Phe Leu Val Gly Ile Thr Ile Ala Val Ser Tyr
    210                 215                 220

Leu Phe Val Pro Gly Cys Ile Arg Thr Pro Gly Ala Gln Met Ala Val
225                 230                 235                 240

Trp Ile Asn Val Gly Tyr Leu Phe Pro Leu Thr Tyr Leu Phe Val Asp
                245                 250                 255

Phe Ala Lys Arg Thr Tyr Ser Lys Arg Ser Ala Ile Ala Ala Gln Lys
```

```
            260                 265                 270

Lys Ala Gln
        275


<210> SEQ ID NO 36
<211> LENGTH: 8739
<212> TYPE: DNA
<213> ORGANISM: Artificial Sequence
<220> FEATURE:
<223> OTHER INFORMATION: Plasmid pY116

<400> SEQUENCE: 36

ggccgccacc gcggcccgag attccggcct cttcggccgc caagcgaccc gggtggacgt     60

ctagaggtac ctagcaatta acagatagtt tgccggtgat aattctctta acctcccaca    120

ctcctttgac ataacgattt atgtaacgaa actgaaattt gaccagatat tgtgtccgcg    180

gtggagctcc agcttttgtt ccctttagtg agggtttaaa cgagcttggc gtaatcatgg    240

tcatagctgt ttcctgtgtg aaattgttat ccgctcacaa ttccacacaa cgtacgagcc    300

ggaagcataa agtgtaaagc ctggggtgcc taatgagtga gctaactcac attaattgcg    360

ttgcgctcac tgcccgcttt ccagtcggga aacctgtcgt gccagctgca ttaatgaatc    420

ggccaacgcg cggggagagg cggtttgcgt attgggcgct cttccgcttc ctcgctcact    480

gactcgctgc gctcggtcgt tcggctgcgg cgagcggtat cagctcactc aaaggcggta    540

atacggttat ccacagaatc aggggataac gcaggaaaga acatgtgagc aaaaggccag    600

caaaaggcca ggaaccgtaa aaaggccgcg ttgctggcgt ttttccatag gctccgcccc    660

cctgacgagc atcacaaaaa tcgacgctca agtcagaggt ggcgaaaccc gacaggacta    720

taaagatacc aggcgtttcc ccctggaagc tccctcgtgc gctctcctgt tccgaccctg    780

ccgcttaccg gatacctgtc cgcctttctc ccttcgggaa gcgtggcgct ttctcatagc    840

tcacgctgta ggtatctcag ttcggtgtag gtcgttcgct ccaagctggg ctgtgtgcac    900

gaaccccccg ttcagcccga ccgctgcgcc ttatccggta actatcgtct tgagtccaac    960

ccggtaagac acgacttatc gccactggca gcagccactg gtaacaggat tagcagagcg   1020

aggtatgtag gcggtgctac agagttcttg aagtggtggc ctaactacgg ctacactaga   1080

aggacagtat ttggtatctg cgctctgctg aagccagtta ccttcggaaa aagagttggt   1140

agctcttgat ccggcaaaca aaccaccgct ggtagcggtg gtttttttgt ttgcaagcag   1200

cagattacgc gcagaaaaaa aggatctcaa gaagatcctt tgatcttttc tacggggtct   1260

gacgctcagt ggaacgaaaa ctcacgttaa gggattttgg tcatgagatt atcaaaaagg   1320

atcttcacct agatcctttt aaattaaaaa tgaagtttta aatcaatcta aagtatatat   1380

gagtaaactt ggtctgacag ttaccaatgc ttaatcagtg aggcacctat ctcagcgatc   1440

tgtctatttc gttcatccat agttgcctga ctccccgtcg tgtagataac tacgatacgg   1500

gagggcttac catctggccc cagtgctgca atgataccgc gagacccacg ctcaccggct   1560

ccagatttat cagcaataaa ccagccagcc ggaagggccg agcgcagaag tggtcctgca   1620

actttatccg cctccatcca gtctattaat tgttgccggg aagctagagt aagtagttcg   1680

ccagttaata gtttgcgcaa cgttgttgcc attgctacag gcatcgtggt gtcacgctcg   1740

tcgtttggta tggcttcatt cagctccggt tcccaacgat caaggcgagt tacatgatcc   1800

cccatgttgt gcaaaaaagc ggttagctcc ttcggtcctc cgatcgttgt cagaagtaag   1860

ttggccgcag tgttatcact catggttatg gcagcactgc ataattctct tactgtcatg   1920

ccatccgtaa gatgcttttc tgtgactggt gagtactcaa ccaagtcatt ctgagaatag   1980
```

-continued

```
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg tttttcgccc tttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
tttaacaaaa tattaacgct tacaatttcc attcgccatt caggctgcgc aactgttggg   2880
aagggcgatc ggtgcgggcc tcttcgctat tacgccagct ggcgaaaggg ggatgtgctg   2940
caaggcgatt aagttgggta acgccagggt tttcccagtc acgacgttgt aaaacgacgg   3000
ccagtgaatt gtaatacgac tcactatagg gcgaattggg taccgggccc cccctcgagg   3060
tcgatggtgt cgataagctt gatatcgaat tcatgtcaca caaaccgatc ttcgcctcaa   3120
ggaaacctaa ttctacatcc gagagactgc cgagatccag tctacactga ttaattttcg   3180
ggccaataat ttaaaaaaat cgtgttatat aatattatat gtattatata tatacatcat   3240
gatgatactg acagtcatgt cccattgcta aatagacaga ctccatctgc cgcctccaac   3300
tgatgttctc aatatttaag ggtcatctc gcattgttta ataataaaca gactccatct   3360
accgcctcca aatgatgttc tcaaaatata ttgtatgaac ttatttttat tacttagtat   3420
tattagacaa cttacttgct ttatgaaaaa cacttcctat ttaggaaaca atttataatg   3480
gcagttcgtt catttaacaa tttatgtaga ataaatgtta taaatgcgta tgggaaatct   3540
taaatatgga tagcataaat gatatctgca ttgcctaatt cgaaatcaac agcaacgaaa   3600
aaaatccctt gtacaacata aatagtcatc gagaaatatc aactatcaaa gaacagctat   3660
tcacacgtta ctattgagat tattattgga cgagaatcac acactcaact gtctttctct   3720
cttctagaaa tacaggtaca agtatgtact attctcattg ttcatacttc tagtcatttc   3780
atcccacata ttccttggat ttctctccaa tgaatgacat tctatcttgc aaattcaaca   3840
attataataa gatataccaa agtagcggta tagtggcaat caaaaagctt ctctggtgtg   3900
cttctcgtat ttatttttat tctaatgatc cattaaaggt atatatttat ttcttgttat   3960
ataatccttt tgtttattac atgggctgga tacataaagg tattttgatt taattttttg   4020
cttaaattca atcccccctc gttcagtgtc aactgtaatg gtaggaaatt accatacttt   4080
tgaagaagca aaaaaaatga aagaaaaaaa aaatcgtatt tccaggttag acgttccgca   4140
gaatctagaa tgcggtatgc ggtacattgt tcttcgaacg taaaagttgc gctccctgag   4200
atattgtaca tttttgcttt tacaagtaca agtacatcgt acaactatgt actactgttg   4260
atgcatccac aacagtttgt tttgtttttt tttgtttttt ttttttctaa tgattcatta   4320
ccgctatgta tacctacttg tacttgtagt aagccgggtt attggcgttc aattaatcat   4380
```

-continued

```
agacttatga atctgcacgg tgtgcgctgc gagttacttt tagcttatgc atgctacttg   4440
ggtgtaatat tgggatctgt tcggaaatca acggatgctc aaccgatttc gacagtaatt   4500
aattaatttg aatcgaatcg gagcctaaaa tgaacccgag tatatctcat aaaattctcg   4560
gtgagaggtc tgtgactgtc agtacaaggt gccttcatta tgccctcaac cttaccatac   4620
ctcactgaat gtagtgtacc tctaaaaatg aaatacagtg ccaaaagcca aggcactgag   4680
ctcgtctaac ggacttgata tacaaccaat taaaacaaat gaaaagaaat acagttcttt   4740
gtatcatttg taacaattac cctgtacaaa ctaaggtatt gaaatcccac aatattccca   4800
aagtccaccc ctttccaaat tgtcatgcct acaactcata taccaagcac taacctacca   4860
aacaccacta aaaccccaca aaatatatct taccgaatat acagtaacaa gctaccacca   4920
cactcgttgg gtgcagtcgc cagcttaaag atatctatcc acatcagcca caactccctt   4980
cctttaataa accgactaca cccttggcta ttgaggttat gagtgaatat actgtagaca   5040
agacactttc aagaagactg tttccaaaac gtaccactgt cctccactac aaacacaccc   5100
aatctgcttc ttctagtcaa ggttgctaca ccggtaaatt ataaatcatc atttcattag   5160
cagggcaggg cccttttat agagtcttat acactagcgg accctgccgg tagaccaacc   5220
cgcaggcgcg tcagtttgct ccttccatca atgcgtcgta gaaacgactt actccttctt   5280
gagcagctcc ttgaccttgt tggcaacaag tctccgacct cggaggtgga ggaagagcct   5340
ccgatatcgg cggtagtgat accagcctcg acggactcct tgacggcagc ctcaacagcg   5400
tcaccggcgg gcttcatgtt aagagagaac ttgagcatca tggcggcaga cagaatggtg   5460
gcaatggggt tgaccttctg cttgccgaga tcgggggcag atccgtgaca gggctcgtac   5520
agaccgaacg cctcgttggt gtcgggcaga gaagccagag aggcggaggg cagcagaccc   5580
agagaaccgg ggatgacgga ggcctcgtcg gagatgatat cgccaaacat gttggtggtg   5640
atgatgatac cattcatctt ggagggctgc ttgatgagga tcatggcggc cgagtcgatc   5700
agctggtggt tgagctcgag ctgggggaat tcgtccttga ggactcgagt gacagtcttt   5760
cgccaaagtc gagaggaggc cagcacgttg gccttgtcaa gagaccacac gggaagaggg   5820
gggttgtgct gaagggccag gaaggcggcc attcgggcaa ttcgctcaac ctcaggaacg   5880
gagtaggtct cggtgtcgga agcgacgcca gatccgtcat cctcctttcg ctctccaaag   5940
tagatacctc cgacgagctc tcggacaatg atgaagtcgg tgccctcaac gtttcggatg   6000
ggggagagat cggcgagctt gggcgacagc agctggcagg gtcgcaggtt ggcgtacagg   6060
ttcaggtcct ttcgcagctt gaggagaccc tgctcgggtc gcacgtcggt tcgtccgtcg   6120
ggagtggtcc atacggtgtt ggcagcgcct ccgacagcac cgagcataat agagtcagcc   6180
tttcggcaga tgtcgagagt agcgtcggtg atgggctcgc cctccttctc aatggcagct   6240
cctccaatga gtcggtcctc aaacacaaac tcggtgccgg aggcctcagc aacagacttg   6300
agcaccttga cggcctcggc aatcacctcg gggccacaga agtcgccgcc gagaagaaca   6360
atcttcttgg agtcagtctt ggtcttctta gtttcgggtt ccattgtgga tgtgtgtggt   6420
tgtatgtgtg atgtggtgtg tggagtgaaa atctgtggct ggcaaacgct cttgtatata   6480
tacgcacttt tgcccgtgct atgtggaaga ctaaacctcc gaagattgtg actcaggtag   6540
tgcggtatcg gctagggacc caaaccttgt cgatgccgat agcgctatcg aacgtacccc   6600
agccggccgg gagtatgtcg gaggggacat acgagatcgt caagggtttg tggccaactg   6660
gtatttaaat gtagctaacg gtagcaggcg aactactggt acatacctcc cccggaatat   6720
gtacaggcat aatgcgtatc tgtgggacat gtggtcgttg cgccattatg taagcagcgt   6780
```

-continued gtactcctct gactgtccat atggtttgct ccatctcacc ctcatcgttt tcattgttca 6840
caggcggcca caaaaaaact gtcttctctc cttctctctt cgccttagtc tactcggacc 6900
agttttagtt tagcttggcg ccactggata aatgagacct caggccttgt gatgaggagg 6960
tcacttatga agcatgttag gaggtgcttg tatggataga gaagcaccca aaataataag 7020
aataataata aaacaggggg cgttgtcatt tcatatcgtg ttttcaccat caatacacct 7080
ccaaacaatg cccttcatgt ggccagcccc aatattgtcc tgtagttcaa ctctatgcag 7140
ctcgtatctt attgagcaag taaaactctg tcagccgata ttgcccgacc cgcgacaagg 7200
gtcaacaagg tggtgtaagg ccttcgcaga agtcaaaact gtgccaaaca aacatctaga 7260
gtctctttgg tgtttctcgc atatatttwa tcggctgtct tacgtatttg cgcctcggta 7320
ccggactaat ttcggatcat ccccaatacg ctttttcttc gcagctgtca acagtgtcca 7380
tgatctatcc acctaaatgg gtcatatgag gcgtataatt tcgtggtgct gataataatt 7440
cccatatatt tgacacaaaa cttccccccc tagacataca tctcacaatc tcacttcttg 7500
tgcttctgtc acacatctcc tccagctgac ttcaactcac acctctgccc cagttggtct 7560
acagcggtat aaggtttctc cgcatagagg tgcaccactc ctcccgatac ttgtttgtgt 7620
gacttgtggg tcacgacata tatatctaca cacattgcgc caccctttgg ttcttccagc 7680
acaacaaaaa cacgacacgc taaccatggc caatttactg accgtacacc aaaatttgcc 7740
tgcattaccg gtcgatgcaa cgagtgatga ggttcgcaag aacctgatgg acatgttcag 7800
ggatcgccag gcgttttctg agcatacctg gaaaatgctt ctgtccgttt gccggtcgtg 7860
ggcggcatgg tgcaagttga ataaccggaa atggtttccc gcagaacctg aagatgttcg 7920
cgattatctt ctatatcttc aggcgcgcgg tctggcagta aaaactatcc agcaacattt 7980
gggccagcta aacatgcttc atcgtcggtc cgggctgcca cgaccaagtg acagcaatgc 8040
tgtttcactg gttatgcggc ggatccgaaa agaaaacgtt gatgccggtg aacgtgcaaa 8100
acaggctcta gcgttcgaac gcactgattt cgaccaggtt cgttcactca tggaaaatag 8160
cgatcgctgc caggatatac gtaatctggc atttctgggg attgcttata acaccctgtt 8220
acgtatagcc gaaattgcca ggatcagggt taaagatatc tcacgtactg acggtgggag 8280
aatgttaatc catattggca gaacgaaaac gctggttagc accgcaggtg tagagaaggc 8340
acttagcctg ggggtaacta aactggtcga gcgatggatt tccgtctctg gtgtagctga 8400
tgatccgaat aactacctgt tttgccgggt cagaaaaaat ggtgttgccg cgccatctgc 8460
caccagccag ctatcaactc gcgccctgga agggattttt gaagcaactc atcgattgat 8520
ttacggcgct aaggatgact ctggtcagag atacctggcc tggtctggac acagtgcccg 8580
tgtcggagcc gcgcgagata tggcccgcgc tggagtttca ataccggaga tcatgcaagc 8640
tggtggctgg accaatgtaa atattgtcat gaactatatc cgtaacctgg atagtgaaac 8700
aggggcaatg gtgcgcctgc tggaagatgg cgattaagc 8739

<210> SEQ ID NO 37
<211> LENGTH: 15337
<212> TYPE: DNA
<213> ORGANISM: Artificial Sequence
<220> FEATURE:
<223> OTHER INFORMATION: Plasmid pKO2UF8289

<400> SEQUENCE: 37
cgatcgagga agaggacaag cggctgcttc ttaagtttgt gacatcagta tccaaggcac 60
cattgcaagg attcaaggct ttgaacccgt catttgccat tcgtaacgct ggtagacagg 120
ttgatcggtt ccctacggcc tccacctgtg tcaatcttct caagctgcct gactatcagg 180
acattgatca acttcggaag aaacttttgt atgccattcg atcacatgct ggtttcgatt 240
tgtcttagag gaacgcatat acagtaatca tagagaataa acgatattca tttattaaag 300
tagatagttg aggtagaagt tgtaaagagt gataaatagc ggccgctcac tgaatctttt 360
tggctccctt gtgcttcctg acgatatacg tttgcacata gaaattcaag aacaaacaca 420
agactgtgcc aacataaaag taattgaaga accagccaaa catcctcatc ccatcttggc 480
gataacaggg aatgttcctg tacttccaga caatgtagaa accaacattg aattgaatga 540
tctgcattga tgtaatcagg gattttggca tggggaactt cagcttgatc aatctggtcc 600
aataataacc gtacatgatc cagtggatga aaccattcaa cagcacaaaa atccaaacag 660
cttcatttcg gtaattatag aacagccaca tatccatcgg tgcccccaaa tgatggaaga 720
attgcaacca ggtcagaggc ttgcccatca gtggcaaata gaaggagtca atatactcca 780
ggaacttgct caaatagaac aactgcgtgg tgatcctgaa gacgttgttg tcaaaagcct 840
tctcgcagtt gtcagacata acaccgatgg tgtacatggc atatgccatt gagaggaatg 900
atcccaacga ataaatggac atgagaaggt tgtaattggt gaaaacaaac ttcatacgag 960
actgaccttt tggaccaagg gggccaagag tgaacttcaa gatgacaaat gcgatggaca 1020
agtaaagcac ctcacagtga ctggcatcac tccagagttg ggcataatca actggttggg 1080
taaaacttcc tgcccaattg agactatttc attcaccacc tccatggtta gcgtgtcgtg 1140
tttttgttgt gctggaagaa ccaaagggtg gcgcaatgtg tgtagatata tatgtcgtga 1200
cccacaagtc acacaaacaa gtatcgggag gagtggtgca cctctatgcg gagaaacctt 1260
ataccgctgt agaccaactg gggcagaggt gtgagttgaa gtcagctgga ggagatgtgt 1320
gacagaagca caagaagtga gattgtgaga tgtatgtcta ggggggggaag ttttgtgtca 1380 aatatatggg aattattatc agcaccacga aattatacgc ctcatatgac ccatttaggt 1440
ggatagatca tggacactgt tgacagctgc gaagaaaaag cgtattgggg atgatccgaa 1500
attagtccgg taccgaggcg caaatacgta agacagccga twaaatatat gcgagaaaca 1560
ccaaagagac tctagatgtt tgtttggcac agttttgact tctgcgaagg ccttacacca 1620
ccttgttgac ccttgtcgcg ggtcgggcaa tatcggctga cagagtttta cttgctcaat 1680
aagatacgag ctgcatagag ttgaactaca ggacaatatt ggggctggcc acatgaaggg 1740
cattgtttgg aggtgtattg atggtgaaaa cacgatatga aatgacaacg ccccctgttt 1800
tattattatt cttattattt tgggtgcttc tctatccata caagcacctc ctaacatgct 1860
tcataagtga cctcctcatc acaaggcctg aggtctcatt tatccagtgg cgccaagcta 1920
aactaaaact ggtccgagta gactaaggcg aagagagaag gagagaagac agttttttttg 1980 tggccgcctg tgaacaatga aaacgatgag ggtgagatgg agcaaaccat atggtttaaa 2040
cagtcagagg agtacacgct gcttacataa tggcgcaacg accacatgtc ccacagatac 2100
gcatcgattc gattcaaatt aattaaaagg cgttgaaaca gaatgagcca gacagcaagg 2160
acaaggtggc caacagcaag gagtccaaaa agccctctat tgacgagatc cacgatgtta 2220
ttgctcatga ggtttccgag ctcgatgctg ggaagaagaa gtgatttgta tataagaaat 2280
aaatgagata tagtaaagga gtgcaagaga atggcaaggt ggtcaaattc tatattactt 2340
gcagtcactg gttcctcgtt gacatgaatg aagttaccgt tggcatagct gatttaatat 2400
ataactgtcc aactaactct cacctagata taacccatgt gtgtgtttcc aatcatcaat 2460
gcggccgctt actgagcctt ggcaccgggc tgcttctcgg ccattcgagc gaactgggac 2520

-continued

```
aggtatcgga gcaggatgac gagaccttca tggggcagag ggtttcggta ggggaggttg   2580
tgcttctggc acagctgttc cacctggtag gaaacggcag tgaggttgtg tcgaggcagg   2640
gtgggccaga gatggtgctc gatctggtag ttcaggcctc caaagaacca gtcagtaatg   2700
atgcctcgtc gaatgttcat ggtctcatgg atctgaccca cagagaagcc atgtccgtcc   2760
cagacggaat caccgatctt ctccagaggg tagtggttca tgaagaccac gatggcaatt   2820
ccgaagccac cgacgagctc ggaaacaaag aacaccagca tcgaggtcag gatggagggc   2880
ataaagaaga ggtggaacag ggtcttgaga gtccagtgca gagcgagtcc aatggcctct   2940
ttcttgtact gagatcggta gaactggttg tctcggtcct tgagggatcg aacggtcagc   3000
acagactgga aacaccagat gaatcgcagg agaatacaga tgaccaggaa atagtactgt   3060
tggaactgaa tgagctttcg ggagatggga gaagctcgag tgacatcgtc ctcggaccag   3120
gcgagcagag gcaggttatc aatgtcggga tcgtgaccct gaacgttggt agcagaatga   3180
tgggcgttgt gtctgtcctt ccaccaggtc acggagaagc cctggagtcc gttgccaaag   3240
accagaccca ggacgttatt ccagtttcgg ttcttgaagg tctggtggtg gcagatgtca   3300
tgagacagcc atcccatttg ctggtagtgc ataccgagca cgagagcacc aatgaagtac   3360
aggtggtact ggaccagcat gaagaaggca agcacgccaa gacccagggt ggtcaagatc   3420
ttgtacgagt accagagggg agaggcgtca aacatgccag tggcgatcag ctcttctcgg   3480
agctttcgga aatcctcctg agcttcgttg acggcagcct ggggaggcag ctcggaagcc   3540
tggttgatct tgggcattcg cttgagcttg tcgaaggctt cctgagagtg cataaccatg   3600
aaggcgtcag tagcatctcg tccctggtag ttctcaatga tttcagctcc accagggtgg   3660
aagttcaccc aagcggagac gtcgtacacc tttccgtcga tgacgagggg cagagcctgt   3720
cgagaagcct tcaccatggc cattgctgta gatatgtctt gtgtgtaagg gggttggggt   3780
ggttgtttgt gttcttgact tttgtgttag caagggaaga cgggcaaaaa agtgagtgtg   3840
gttgggaggg agagacgagc cttatatata atgcttgttt gtgtttgtgc aagtggacgc   3900
cgaaacgggc aggagccaaa ctaaacaagg cagacaatgc gagcttaatt ggattgcctg   3960
atgggcaggg gttagggctc gatcaatggg ggtgcgaagt gacaaaattg ggaattaggt   4020
tcgcaagcaa ggctgacaag actttggccc aaacatttgt acgcggtgga caacaggagc   4080
cacccatcgt ctgtcacggg ctagccggtc gtgcgtcctg tcaggctcca cctaggctcc   4140
atgccactcc atacaatccc actagtgtac cgctaggccg cttttagctc ccatctaaga   4200
cccccccaaa acctccactg tacagtgcac tgtactgtgt ggcgatcaag ggcaagggaa   4260
aaaaggcgca aacatgcacg catggaatga cgtaggtaag gcgttactag actgaaaagt   4320
ggcacatttc ggcgtgccaa agggtcctag gtgcgtttcg cgagctgggc gccaggccaa   4380
gccgctccaa aacgcctctc cgactccctc cagcggcctc catatcccca tccctctcca   4440
cagcaatgtt gttaagcctt gcaaacgaaa aaatagaaag gctaataagc ttccaatatt   4500
gtggtgtacg ctgcataacg caacaatgag cgccaaacaa cacacacaca cagcacacag   4560
cagcattaac cacgatgttt aaacagtgta cgcagatccc gtcaacagtt ttatatatcg   4620
tagttacaac catcaacact ttttggtaag tgtaccattc tatactccaa ctggtctgca   4680
actgtacaag tagacatgtt aatggtagtt aataacatct acagcagaac ctatggtaaa   4740
gacattgcat ttttacagga agtatcgtcc tacacgttga taaatccaaa gatgcggaac   4800
ttcttccact tttatcatca tcccctactc gtacactcgt actctttgtt cgatcgcgat   4860
tcatttctat aaataatctt gtatgtacat gcggccgctt aagcaacggg cttgataaca   4920
```

-continued

```
gcgggggggg tgcccacgtt gttgcggttg cggaagaaca gaacaccctt accagcaccc   4980
tcggcaccag cgctgggctc aacccactgg cacatacgcg cactgcggta catggcgcgg   5040
atgaagccac gaggaccatc ctggacatca gcccggtagt gcttgcccat gatgggctta   5100
atggcctcgg tggcctcgtc cgcgttgtag aaggggatgc tgctgacgta gtggtggagg   5160
acatgagtct cgatgatgcc gtggagaagg tggcggccga tgaagcccat ctcacggtca   5220
atggtagcag cggcaccacg gacgaagttc cactcgtcgt tggtgtagtg gggaagggta   5280
gggtcggtgt gctggaggaa ggtgatggca acgagccagt ggttaaccca gaggtaggga   5340
acaaagtacc agatggccat gttgtagaaa ccgaacttct gaacgaggaa gtacagagca   5400
gtggccatca gaccgatacc aatatcgctg aggacgatga gcttagcgtc actgttctcg   5460
tacagagggc tgcggggatc gaagtggtta acaccaccgc cgaggccgtt atgcttgccc   5520
ttgccgcgac cctcacgctg gcgctcgtgg tagttgtggc cggtaacatt ggtgatgagg   5580
tagttgggcc agccaacgag ctgctgaagg acgagcatga gaagagtgaa agcgggggtc   5640
tcctcagtaa gatgagcgag ctcgtgggtc atctttccga gacgagtagc ctgctgctcg   5700
cgggttcggg gaacgaagac catgtcacgc tccatgttgc cagtggcctt gtggtgcttt   5760
cggtgggaga tttgccagct gaagtagggg acaaggaggg aagagtgaag aacccagcca   5820
gtaatgtcgt tgatgatgcg agaatcggag aaagcaccgt gaccgcactc atgggcaata   5880
acccagagac cagtaccgaa aagaccctga agaacggtgt acacggccca cagaccagcg   5940
cgggcggggg tggaggggat atattcgggg gtcacaaagt tgtaccagat gctgaaagtg   6000
gtagtcagga ggacaatgtc gcggaggata taaccgtatc ccttgagagc ggagcgcttg   6060
aagcagtgct tagggatggc attgtagatg tccttgatgg taaagtcggg aacctcgaac   6120
tggttgccgt aggtgtcgag catgacacca tactcggact tgggcttggc gatatcaacc   6180
tcggacatgg acgagagcga tgtggaagag gccgagtggc ggggagagtc tgaaggagag   6240
acggcggcag actcagaatc cgtcacagta gttgaggtga cggtgcgtct aagcgcaggg   6300
ttctgcttgg gcagagccga agtggacgcc atggttgtga attagggtgg tgagaatggt   6360
tggttgtagg gaagaatcaa aggccggtct cgggatccgt gggtatatat atatatatat   6420
atatatacga tccttcgtta cctccctgtt ctcaaaactg tggtttttcg tttttcgttt   6480
tttgcttttt ttgatttttt tagggccaac taagcttcca gatttcgcta atcacctttg   6540
tactaattac aagaaaggaa gaagctgatt agagttgggc tttttatgca actgtgctac   6600
tccttatctc tgatatgaaa gtgtagaccc aatcacatca tgtcatttag agttggtaat   6660
actgggagga tagataaggc acgaaaacga gccatagcag acatgctggg tgtagccaag   6720
cagaagaaag tagatgggag ccaattgacg agcgagggag ctacgccaat ccgacatacg   6780
acacgctgag atcgtcttgg ccgggggggta cctacagatg tccaagggta agtgcttgac   6840
tgtaattgta tgtctgagga caaatatgta gtcagccgta taaagtcata ccaggcacca   6900
gtgccatcat cgaaccacta actctctatg atacatgcct ccggtattat tgtaccatgc   6960
gtcgctttgt tacatacgta tcttgccttt ttctctcaga aactccagac tttggctatt   7020
ggtcgagata agcccggacc atagtgagtc tttcacactc tacatttctc ccttgctcca   7080
actatttaaa ttgccccgga gaagacggcc aggccgccta gatgacaaat tcaacaactc   7140
acagctgact ttctgccatt gccactaggg gggggccttt ttatatggcc aagccaagct   7200
ctccacgtcg gttgggctgc acccaacaat aaatgggtag ggttgcacca acaaagggat   7260
gggatggggg gtagaagata cgaggataac ggggctcaat ggcacaaata agaacgaata   7320
```

-continued

```
ctgccattaa gactcgtgat ccagcgactg acaccattgc atcatctaag ggcctcaaaa   7380
ctacctcgga actgctgcgc tgatctggac accacagagg ttccgagcac tttaggttgc   7440
accaaatgtc ccaccaggtg caggcagaaa acgctggaac agcgtgtaca gtttgtctta   7500
acaaaaagtg agggcgctga ggtcgagcag ggtggtgtga cttgttatag cctttagagc   7560
tgcgaaagcg cgtatggatt tggctcatca ggccagattg agggtctgtg gacacatgtc   7620
atgttagtgt acttcaatcg ccccctggat atagccccga caataggccg tggcctcatt   7680
tttttgcctt ccgcacattt ccattgctcg gtacccacac cttgcttctc ctgcacttgc   7740
caaccttaat actggtttac attgaccaac atcttacaag cgggggggctt gtctagggta   7800
tatataaaca gtggctctcc caatcggttg ccagtctctt ttttcctttc tttccccaca   7860
gattcgaaat ctaaactaca catcacagaa ttccgagccg tgagtatcca cgacaagatc   7920
agtgtcgaga cgacgcgttt tgtgtaatga cacaatccga aagtcgctag caacacacac   7980
tctctacaca aactaaccca gctctggtac catggtgaag gcttctcgac aggctctgcc   8040
cctcgtcatc gacggaaagg tgtacgacgt ctccgcttgg gtgaacttcc accctggtgg   8100
agctgaaatc attgagaact accagggacg agatgctact gacgccttca tggttatgca   8160
ctctcaggaa gccttcgaca agctcaagcg aatgcccaag atcaaccagg cttccgagct   8220
gcctccccag gctgccgtca acgaagctca ggaggatttc cgaaagctcc gagaagagct   8280
gatcgccact ggcatgtttg acgcctctcc cctctggtac tcgtacaaga tcttgaccac   8340
cctgggtctt ggcgtgcttg ccttcttcat gctggtccag taccacctgt acttcattgg   8400
tgctctcgtg ctcggtatgc actaccagca aatgggatgg ctgtctcatg acatctgcca   8460
ccaccagacc ttcaagaacc gaaactggaa taacgtcctg ggtctggtct ttggcaacgg   8520
actccagggc ttctccgtga cctggtggaa ggacagacac aacgcccatc attctgctac   8580
caacgttcag ggtcacgatc ccgacattga taacctgcct ctgctcgcct ggtccgagga   8640
cgatgtcact cgagcttctc ccatctcccg aaagctcatt cagttccaac agtactattt   8700
cctggtcatc tgtattctcc tgcgattcat ctggtgtttc cagtctgtgc tgaccgttcg   8760
atccctcaag gaccgagaca accagttcta ccgatctcag tacaagaaag aggccattgg   8820
actcgctctg cactggactc tcaagaccct gttccacctc ttctttatgc cctccatcct   8880
gacctcgatg ctggtgttct ttgtttccga gctcgtcggt ggcttcggaa ttgccatcgt   8940
ggtcttcatg aaccactacc ctctggagaa gatcggtgat tccgtctggg acggacatgg   9000
cttctctgtg ggtcagatcc atgagaccat gaacattcga cgaggcatca ttactgactg   9060
gttctttgga ggcctgaact accagatcga gcaccatctc tggcccaccc tgcctcgaca   9120
caacctcact gccgtttcct accaggtgga acagctgtgc cagaagcaca acctccccta   9180
ccgaaaccct ctgccccatg aaggtctcgt catcctgctc cgatacctgt cccagttcgc   9240
tcgaatggcc gagaagcagc ccggtgccaa ggctcagtaa gcggccgcaa gtgtggatgg   9300
ggaagtgagt gcccggttct gtgtgcacaa ttggcaatcc aagatggatg gattcaacac   9360
agggatatag cgagctacgt ggtggtgcga ggatatagca acggatattt atgtttgaca   9420
cttgagaatg tacgatacaa gcactgtcca agtacaatac taaacatact gtacatactc   9480
atactcgtac ccgggcaacg gtttcacttg agtgcagtgg ctagtgctct tactcgtaca   9540
gtgtgcaata ctgcgtatca tagtctttga tgtatatcgt attcattcat gttagttgcg   9600
tacgggtgaa gcttccactg gtcggcgtgg tagtggggca gagtggggtc ggtgtgctgc   9660
aggtaggtga tggccacgag ccagtggttg acccacaggt aggggatcag gtagtagagg   9720
```

-continued

```
gtgacggaag ccaggcccca tcggttgatg gagtatgcga tgacggacat ggtgatacca   9780
ataccgacgt tagagatcca gatgttgaac cagtccttct tctcaaacag cggggcgttg   9840
gggttgaagt ggttgacagc ccatttgttg agcttggggt acttctgtcc ggtaacgtaa   9900
gacagcagat acagaggcca tccaaacacc tgctgggtga tgaggccgta gagggtcatg   9960
aggggagcgt cctcagcaag ctcagaccag tcatgggcgc ctcggttctc cataaactcc  10020
tttcggtcct tgggcacaaa caccatatca cgggtgaggt gaccagtgga cttgtggtgc  10080
atggagtggg tcagcttcca ggcgtagtaa gggaccagca tggaggagtg cagaacccat  10140
ccggtgacgt tgttgacggt gttagagtcg gagaaagcag agtggccaca ctcgtgggca  10200
agaacccaca gaccggtgcc aaacagaccc tggacaatgg agtacatggc ccaggccaca  10260
gctcggccgg aagccgaggg aataagaggc aggtacgcgt aggccatgta ggcaaaaacg  10320
gcgataaaga agcaggcgcg ccagctgcat taatgaatcg gccaacgcgc ggggagaggc  10380
ggtttgcgta ttgggcgctc ttccgcttcc tcgctcactg actcgctgcg ctcggtcgtt  10440
cggctgcggc gagcggtatc agctcactca aaggcggtaa tacggttatc cacagaatca  10500
ggggataacg caggaaagaa catgtgagca aaaggccagc aaaaggccag gaaccgtaaa  10560
aaggccgcgt tgctggcgtt tttccatagg ctccgccccc ctgacgagca tcacaaaaat  10620
cgacgctcaa gtcagaggtg gcgaaacccg acaggactat aaagatacca ggcgtttccc  10680
cctggaagct ccctcgtgcg ctctcctgtt ccgaccctgc cgcttaccgg atacctgtcc  10740
gcctttctcc cttcgggaag cgtggcgctt tctcatagct cacgctgtag gtatctcagt  10800
tcggtgtagg tcgttcgctc caagctgggc tgtgtgcacg aaccccccgt tcagcccgac  10860
cgctgcgcct tatccggtaa ctatcgtctt gagtccaacc cggtaagaca cgacttatcg  10920
ccactggcag cagccactgg taacaggatt agcagagcga ggtatgtagg cggtgctaca  10980
gagttcttga agtggtggcc taactacggc tacactagaa gaacagtatt tggtatctgc  11040
gctctgctga agccagttac cttcggaaaa agagttggta gctcttgatc cggcaaacaa  11100
accaccgctg gtagcggtgg tttttttgtt tgcaagcagc agattacgcg cagaaaaaaa  11160
ggatctcaag aagatccttt gatcttttct acggggtctg acgctcagtg gaacgaaaac  11220
tcacgttaag ggattttggt catgagatta tcaaaaagga tcttcaccta gatcctttta  11280
aattaaaaat gaagttttaa atcaatctaa agtatatatg agtaaacttg gtctgacagt  11340
taccaatgct taatcagtga ggcacctatc tcagcgatct gtctatttcg ttcatccata  11400
gttgcctgac tccccgtcgt gtagataact acgatacggg agggcttacc atctggcccc  11460
agtgctgcaa tgataccgcg agacccacgc tcaccggctc cagatttatc agcaataaac  11520
cagccagccg gaagggccga gcgcagaagt ggtcctgcaa ctttatccgc ctccatccag  11580
tctattaatt gttgccggga agctagagta agtagttcgc cagttaatag tttgcgcaac  11640
gttgttgcca ttgctacagg catcgtggtg tcacgctcgt cgtttggtat ggcttcattc  11700
agctccggtt cccaacgatc aaggcgagtt acatgatccc ccatgttgtg caaaaaagcg  11760
gttagctcct tcggtcctcc gatcgttgtc agaagtaagt tggccgcagt gttatcactc  11820
atggttatgg cagcactgca taattctctt actgtcatgc catccgtaag atgcttttct  11880
gtgactggtg agtactcaac caagtcattc tgagaatagt gtatgcggcg accgagttgc  11940
tcttgcccgg cgtcaatacg ggataatacc gcgccacata gcagaacttt aaaagtgctc  12000
atcattggaa aacgttcttc ggggcgaaaa ctctcaagga tcttaccgct gttgagatcc  12060
agttcgatgt aacccactcg tgcacccaac tgatcttcag catcttttac tttcaccagc  12120
```

```
gtttctgggt gagcaaaaac aggaaggcaa aatgccgcaa aaaagggaat aagggcgaca  12180
cggaaatgtt gaatactcat actcttcctt tttcaatatt attgaagcat ttatcagggt  12240
tattgtctca tgagcggata catatttgaa tgtatttaga aaaataaaca aataggggtt  12300
ccgcgcacat ttccccgaaa agtgccacct gatgcggtgt gaaataccgc acagatgcgt  12360
aaggagaaaa taccgcatca ggaaattgta agcgttaata ttttgttaaa attcgcgtta  12420
aatttttgtt aaatcagctc attttttaac caataggccg aaatcggcaa aatcccttat  12480
aaatcaaaag aatagaccga gatagggttg agtgttgttc cagtttggaa caagagtcca  12540
ctattaaaga acgtggactc caacgtcaaa gggcgaaaaa ccgtctatca gggcgatggc  12600
ccactacgtg aaccatcacc ctaatcaagt tttttggggt cgaggtgccg taaagcacta  12660
aatcggaacc ctaaagggag cccccgattt agagcttgac ggggaaagcc ggcgaacgtg  12720
gcgagaaagg aagggaagaa agcgaaagga gcgggcgcta gggcgctggc aagtgtagcg  12780
gtcacgctgc gcgtaaccac cacacccgcc gcgcttaatg cgccgctaca gggcgcgtcc  12840
attcgccatt caggctgcgc aactgttggg aagggcgatc ggtgcgggcc tcttcgctat  12900
tacgccagct ggcgaaaggg ggatgtgctg caaggcgatt aagttgggta acgccagggt  12960
tttcccagtc acgacgttgt aaaacgacgg ccagtgaatt gtaatacgac tcactatagg  13020
gcgaattggg cccgacgtcg catgcttgaa tctacaagta ggagggttgg agtgattaag  13080
tgaaacttct ttaacggctc tatgccagtt ctattgatat ccgaaacatc agtatgaagg  13140
tctgataagg gtgacttctt cccacagatt cgtatcagta cgagtacgag accggtactt  13200
gtaacagtat tgatactaaa gggaaactac aacggttgtc agcgtaatgt gacttcgccc  13260
atgaacgcag acacgcagtg ccgagtgcgg tgatatcgcc tactcgttac gtccatggac  13320
tacacaaccc ctcggcttcg cttggcttag cctcgggctc ggtgctgttc agttaaaaca  13380
caatcaaata acatttctac tttttagaag gcaggccgtc aggagcaact ccgactccat  13440
tgacgtttct aaacatctga atgccttcct taccttcaac aaactggcag gttcgggcga  13500
cagtgtaaag agacttgatg aagttggtgt cgtcgtgtcg gtagtgcttg cccatgacct  13560
tcttgatctt ctcagtggcg attcgggcgt tgtagaaggg aattccttta cctgcaggat  13620
aacttcgtat aatgtatgct atacgaagtt atgatctctc tcttgagctt ttccataaca  13680
agttcttctg cctccaggaa gtccatgggt ggtttgatca tggttttggt gtagtggtag  13740
tgcagtggtg gtattgtgac tggggatgta gttgagaata agtcatacac aagtcagctt  13800
tcttcgagcc tcatataagt ataagtagtt caacgtatta gcactgtacc cagcatctcc  13860
gtatcgagaa acacaacaac atgccccatt ggacagatca tgcggataca caggttgtgc  13920
agtatcatac atactcgatc agacaggtcg tctgaccatc atacaagctg aacaagcgct  13980
ccatacttgc acgctctcta tatacacagt taaattacat atccatagtc taacctctaa  14040
cagttaatct tctggtaagc ctcccagcca gccttctggt atcgcttggc ctcctcaata  14100
ggatctcggt tctggccgta cagacctcgg ccgacaatta tgatatccgt tccggtagac  14160
atgacatcct caacagttcg gtactgctgt ccgagagcgt ctcccttgtc gtcaagaccc  14220
accccggggg tcagaataag ccagtcctca gagtcgccct taggtcggtt ctgggcaatg  14280
aagccaacca caaactcggg gtcggatcgg gcaagctcaa tggtctgctt ggagtactcg  14340
ccagtggcca gagagccctt gcaagacagc tcggccagca tgagcagacc tctggccagc  14400
ttctcgttgg gagaggggac taggaactcc ttgtactggg agttctcgta gtcagagacg  14460
tcctccttct tctgttcaga gacagtttcc tcggcaccag ctcgcaggcc agcaatgatt  14520
```

```
ccggttccgg gtacaccgtg ggcgttggtg atatcggacc actcggcgat tcggtgacac  14580

cggtactggt gcttgacagt gttgccaata tctgcgaact ttctgtcctc gaacaggaag  14640

aaaccgtgct taagagcaag ttccttgagg gggagcacag tgccggcgta ggtgaagtcg  14700

tcaatgatgt cgatatgggt tttgatcatg cacacataag gtccgacctt atcggcaagc  14760

tcaatgagct ccttggtggt ggtaacatcc agagaagcac acaggttggt tttcttggct  14820

gccacgagct tgagcactcg agcggcaaag gcggacttgt ggacgttagc tcgagcttcg  14880

taggagggca ttttggtggt gaagaggaga ctgaaataaa tttagtctgc agaacttttt  14940

atcggaacct tatctggggc agtgaagtat atgttatggt aatagttacg agttagttga  15000

acttatagat agactggact atacggctat cggtccaaat tagaaagaac gtcaatggct  15060

ctctgggcgt cgcctttgcc gacaaaaatg tgatcatgat gaaagccagc aatgacgttg  15120

cagctgatat tgttgtcggc caaccgcgcc gaaaacgcag ctgtcagacc cacagcctcc  15180

aacgaagaat gtatcgtcaa agtgatccaa gcacactcat agttggagtc gtactccaaa  15240

ggcggcaatg acgagtcaga cagatactcg tcgacgcgat aacttcgtat aatgtatgct  15300

atacgaagtt atcgtacgat agttagtaga caacaat                          15337


<210> SEQ ID NO 38
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<300> PUBLICATION INFORMATION:
<302> TITLE: A  DELTA-12 DESATURASE GENE SUITABLE FOR ALTERING LEVELS
      OF POLYUNSATURATED FATTY ACIDS IN OLEAGINOUS YEASTS
<310> PATENT DOCUMENT NUMBER: U.S. 7,214,491
<311> PATENT FILING DATE: 2004-05-06
<312> PUBLICATION DATE: 2007-05-08
<313> RELEVANT RESIDUES IN SEQ ID NO: (1)..(1936)
<300> PUBLICATION INFORMATION:
<302> TITLE: A  DELTA-12 DESATURASE GENE SUITABLE FOR ALTERING LEVELS
      OF POLYUNSATURATED FATTY ACIDS IN OLEAGINOUS YEASTS
<310> PATENT DOCUMENT NUMBER: WO 2004/104167
<311> PATENT FILING DATE: 2004-05-07
<312> PUBLICATION DATE: 2004-12-02
<313> RELEVANT RESIDUES IN SEQ ID NO: (1)..(1936)

<400> SEQUENCE: 38

cgtagttata tacaagaggt agatgcgtgc tggtgttaga ggggctctca ggattaggag     60

gaaaatttga cattggccct caacatataa cctcgggtgt gcctctgttt accctcagct    120

tttgcttgtc cccaagtcag tcacgccagg ccaaaaaggt tggtggattg acagggagaa    180

aaaaaaaagc ctagtgggtt taaactcgag gtaagacatt gaaatatata ccggtcggca    240

tcctgagtcc ctttctcgta ttccaacaga ccgaccatag aa atg gat tcg acc       294
                                                Met Asp Ser Thr
                                                1

acg cag acc aac acc ggc acc ggc aag gtg gcc gtg cag ccc ccc acg      342
Thr Gln Thr Asn Thr Gly Thr Gly Lys Val Ala Val Gln Pro Pro Thr
5                   10                  15                  20

gcc ttc att aag ccc att gag aag gtg tcc gag ccc gtc tac gac acc      390
Ala Phe Ile Lys Pro Ile Glu Lys Val Ser Glu Pro Val Tyr Asp Thr
                25                  30                  35

ttt ggc aac gag ttc act cct cca gac tac tct atc aag gat att ctg      438
Phe Gly Asn Glu Phe Thr Pro Pro Asp Tyr Ser Ile Lys Asp Ile Leu
            40                  45                  50

gat gcc att ccc cag gag tgc tac aag cgg tcc tac gtt aag tcc tac      486
Asp Ala Ile Pro Gln Glu Cys Tyr Lys Arg Ser Tyr Val Lys Ser Tyr
```

-continued

```
        55                  60                  65

tcg tac gtg gcc cga gac tgc ttc ttt atc gcc gtt ttt gcc tac atg      534
Ser Tyr Val Ala Arg Asp Cys Phe Phe Ile Ala Val Phe Ala Tyr Met
    70                  75                  80

gcc tac gcg tac ctg cct ctt att ccc tcg gct tcc ggc cga gct gtg      582
Ala Tyr Ala Tyr Leu Pro Leu Ile Pro Ser Ala Ser Gly Arg Ala Val
85                  90                  95                  100

gcc tgg gcc atg tac tcc att gtc cag ggt ctg ttt ggc acc ggt ctg      630
Ala Trp Ala Met Tyr Ser Ile Val Gln Gly Leu Phe Gly Thr Gly Leu
                105                 110                 115

tgg gtt ctt gcc cac gag tgt ggc cac tct gct ttc tcc gac tct aac      678
Trp Val Leu Ala His Glu Cys Gly His Ser Ala Phe Ser Asp Ser Asn
            120                 125                 130

acc gtc aac aac gtc acc gga tgg gtt ctg cac tcc tcc atg ctg gtc      726
Thr Val Asn Asn Val Thr Gly Trp Val Leu His Ser Ser Met Leu Val
        135                 140                 145

cct tac tac gcc tgg aag ctg acc cac tcc atg cac cac aag tcc act      774
Pro Tyr Tyr Ala Trp Lys Leu Thr His Ser Met His His Lys Ser Thr
    150                 155                 160

ggt cac ctc acc cgt gat atg gtg ttt gtg ccc aag gac cga aag gag      822
Gly His Leu Thr Arg Asp Met Val Phe Val Pro Lys Asp Arg Lys Glu
165                 170                 175                 180

ttt atg gag aac cga ggc gcc cat gac tgg tct gag ctt gct gag gac      870
Phe Met Glu Asn Arg Gly Ala His Asp Trp Ser Glu Leu Ala Glu Asp
                185                 190                 195

gct ccc ctc atg acc ctc tac ggc ctc atc acc cag cag gtg ttt gga      918
Ala Pro Leu Met Thr Leu Tyr Gly Leu Ile Thr Gln Gln Val Phe Gly
            200                 205                 210

tgg cct ctg tat ctg ctg tct tac gtt acc gga cag aag tac ccc aag      966
Trp Pro Leu Tyr Leu Leu Ser Tyr Val Thr Gly Gln Lys Tyr Pro Lys
        215                 220                 225

ctc aac aaa tgg gct gtc aac cac ttc aac ccc aac gcc ccg ctg ttt     1014
Leu Asn Lys Trp Ala Val Asn His Phe Asn Pro Asn Ala Pro Leu Phe
    230                 235                 240

gag aag aag gac tgg ttc aac atc tgg atc tct aac gtc ggt att ggt     1062
Glu Lys Lys Asp Trp Phe Asn Ile Trp Ile Ser Asn Val Gly Ile Gly
245                 250                 255                 260

atc acc atg tcc gtc atc gca tac tcc atc aac cga tgg ggc ctg gct     1110
Ile Thr Met Ser Val Ile Ala Tyr Ser Ile Asn Arg Trp Gly Leu Ala
                265                 270                 275

tcc gtc acc ctc tac tac ctg atc ccc tac ctg tgg gtc aac cac tgg     1158
Ser Val Thr Leu Tyr Tyr Leu Ile Pro Tyr Leu Trp Val Asn His Trp
            280                 285                 290

ctc gtg gcc atc acc tac ctg cag cac acc gac ccc act ctg ccc cac     1206
Leu Val Ala Ile Thr Tyr Leu Gln His Thr Asp Pro Thr Leu Pro His
        295                 300                 305

tac cac gcc gac cag tgg aac ttc acc cga gga gcc gcc gcc acc atc     1254
Tyr His Ala Asp Gln Trp Asn Phe Thr Arg Gly Ala Ala Ala Thr Ile
    310                 315                 320

gac cga gag ttt ggc ttc atc ggc tcc ttc tgc ttc cat gac atc atc     1302
Asp Arg Glu Phe Gly Phe Ile Gly Ser Phe Cys Phe His Asp Ile Ile
325                 330                 335                 340

gag acc cac gtt ctg cac cac tac gtg tct cga att ccc ttc tac aac     1350
Glu Thr His Val Leu His His Tyr Val Ser Arg Ile Pro Phe Tyr Asn
                345                 350                 355

gcc cga atc gcc act gag aag atc aag aag gtc atg ggc aag cac tac     1398
Ala Arg Ile Ala Thr Glu Lys Ile Lys Lys Val Met Gly Lys His Tyr
            360                 365                 370

cga cac gac gac acc aac ttc atc aag tct ctt tac act gtc gcc cga     1446
Arg His Asp Asp Thr Asn Phe Ile Lys Ser Leu Tyr Thr Val Ala Arg
```

-continued

```
        375                 380                 385

acc tgc cag ttt gtt gaa ggt aag gaa ggc att cag atg ttt aga aac     1494
Thr Cys Gln Phe Val Glu Gly Lys Glu Gly Ile Gln Met Phe Arg Asn
    390                 395                 400

gtc aat gga gtc gga gtt gct cct gac ggc ctg cct tct aaa aag         1539
Val Asn Gly Val Gly Val Ala Pro Asp Gly Leu Pro Ser Lys Lys
405                 410                 415

tagagctaga aatgttattt gattgtgttt taactgaaca gcaccgagcc cgaggctaag   1599

ccaagcgaag ccgaggggtt gtgtagtcca tggacgtaac gagtaggcga tatcaccgca   1659

ctcggcactg cgtgtctgcg ttcatgggcg aagtcacatt acgctgacaa ccgttgtagt   1719

ttccctttag tatcaatact gttacaagta ccggtctcgt actcgtactg atacgaatct   1779

gtgggaagaa gtcaccctta tcagaccttc atactgatgt ttcggatatc aatagaactg   1839

gcatagagcc gttaaagaag tttcacttaa tcactccaac cctcctactt gtagattcaa   1899

gcagatcgat aagatggatt tgatggtcag tgctagc                            1936


<210> SEQ ID NO 39
<211> LENGTH: 419
<212> TYPE: PRT
<213> ORGANISM: Yarrowia lipolytica

<400> SEQUENCE: 39

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255
```

```
Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys


<210> SEQ ID NO 40
<211> LENGTH: 1272
<212> TYPE: DNA
<213> ORGANISM: Artificial Sequence
<220> FEATURE:
<223> OTHER INFORMATION: mutant EgD8S-23 delta-8 desaturase
<220> FEATURE:
<221> NAME/KEY: CDS
<222> LOCATION: (2)..(1270)

<400> SEQUENCE: 40

c atg gtg aag gct tct cga cag gct ctg ccc ctc gtc atc gac gga aag      49
Met Val Lys Ala Ser Arg Gln Ala Leu Pro Leu Val Ile Asp Gly Lys
1               5                   10                  15

gtg tac gac gtc tcc gct tgg gtg aac ttc cac cct ggt gga gct gaa       97
Val Tyr Asp Val Ser Ala Trp Val Asn Phe His Pro Gly Gly Ala Glu
            20                  25                  30

atc att gag aac tac cag gga cga gat gct act gac gcc ttc atg gtt      145
Ile Ile Glu Asn Tyr Gln Gly Arg Asp Ala Thr Asp Ala Phe Met Val
        35                  40                  45

atg cac tct cag gaa gcc ttc gac aag ctc aag cga atg ccc aag atc      193
Met His Ser Gln Glu Ala Phe Asp Lys Leu Lys Arg Met Pro Lys Ile
    50                  55                  60

aac cag gct tcc gag ctg cct ccc cag gct gcc gtc aac gaa gct cag      241
Asn Gln Ala Ser Glu Leu Pro Pro Gln Ala Ala Val Asn Glu Ala Gln
65                  70                  75                  80

gag gat ttc cga aag ctc cga gaa gag ctg atc gcc act ggc atg ttt      289
Glu Asp Phe Arg Lys Leu Arg Glu Glu Leu Ile Ala Thr Gly Met Phe
                85                  90                  95

gac gcc tct ccc ctc tgg tac tcg tac aag atc ttg acc acc ctg ggt      337
Asp Ala Ser Pro Leu Trp Tyr Ser Tyr Lys Ile Leu Thr Thr Leu Gly
            100                 105                 110

ctt ggc gtg ctt gcc ttc ttc atg ctg gtc cag tac cac ctg tac ttc      385
Leu Gly Val Leu Ala Phe Phe Met Leu Val Gln Tyr His Leu Tyr Phe
        115                 120                 125

att ggt gct ctc gtg ctc ggt atg cac tac cag caa atg gga tgg ctg      433
Ile Gly Ala Leu Val Leu Gly Met His Tyr Gln Gln Met Gly Trp Leu
    130                 135                 140
```

```
tct cat gac atc tgc cac cac cag acc ttc aag aac cga aac tgg aat      481
Ser His Asp Ile Cys His His Gln Thr Phe Lys Asn Arg Asn Trp Asn
145                 150                 155                 160

aac gtc ctg ggt ctg gtc ttt ggc aac gga ctc cag ggc ttc tcc gtg      529
Asn Val Leu Gly Leu Val Phe Gly Asn Gly Leu Gln Gly Phe Ser Val
                165                 170                 175

acc tgg tgg aag gac aga cac aac gcc cat cat tct gct acc aac gtt      577
Thr Trp Trp Lys Asp Arg His Asn Ala His His Ser Ala Thr Asn Val
            180                 185                 190

cag ggt cac gat ccc gac att gat aac ctg cct ctg ctc gcc tgg tcc      625
Gln Gly His Asp Pro Asp Ile Asp Asn Leu Pro Leu Leu Ala Trp Ser
        195                 200                 205

gag gac gat gtc act cga gct tct ccc atc tcc cga aag ctc att cag      673
Glu Asp Asp Val Thr Arg Ala Ser Pro Ile Ser Arg Lys Leu Ile Gln
    210                 215                 220

ttc caa cag tac tat ttc ctg gtc atc tgt att ctc ctg cga ttc atc      721
Phe Gln Gln Tyr Tyr Phe Leu Val Ile Cys Ile Leu Leu Arg Phe Ile
225                 230                 235                 240

tgg tgt ttc cag tct gtg ctg acc gtt cga tcc ctc aag gac cga gac      769
Trp Cys Phe Gln Ser Val Leu Thr Val Arg Ser Leu Lys Asp Arg Asp
                245                 250                 255

aac cag ttc tac cga tct cag tac aag aaa gag gcc att gga ctc gct      817
Asn Gln Phe Tyr Arg Ser Gln Tyr Lys Lys Glu Ala Ile Gly Leu Ala
            260                 265                 270

ctg cac tgg act ctc aag acc ctg ttc cac ctc ttc ttt atg ccc tcc      865
Leu His Trp Thr Leu Lys Thr Leu Phe His Leu Phe Phe Met Pro Ser
        275                 280                 285

atc ctg acc tcg atg ctg gtg ttc ttt gtt tcc gag ctc gtc ggt ggc      913
Ile Leu Thr Ser Met Leu Val Phe Phe Val Ser Glu Leu Val Gly Gly
    290                 295                 300

ttc gga att gcc atc gtg gtc ttc atg aac cac tac cct ctg gag aag      961
Phe Gly Ile Ala Ile Val Val Phe Met Asn His Tyr Pro Leu Glu Lys
305                 310                 315                 320

atc ggt gat tcc gtc tgg gac gga cat ggc ttc tct gtg ggt cag atc     1009
Ile Gly Asp Ser Val Trp Asp Gly His Gly Phe Ser Val Gly Gln Ile
                325                 330                 335

cat gag acc atg aac att cga cga ggc atc att act gac tgg ttc ttt     1057
His Glu Thr Met Asn Ile Arg Arg Gly Ile Ile Thr Asp Trp Phe Phe
            340                 345                 350

gga ggc ctg aac tac cag atc gag cac cat ctc tgg ccc acc ctg cct     1105
Gly Gly Leu Asn Tyr Gln Ile Glu His His Leu Trp Pro Thr Leu Pro
        355                 360                 365

cga cac aac ctc act gcc gtt tcc tac cag gtg gaa cag ctg tgc cag     1153
Arg His Asn Leu Thr Ala Val Ser Tyr Gln Val Glu Gln Leu Cys Gln
    370                 375                 380

aag cac aac ctc ccc tac cga aac cct ctg ccc cat gaa ggt ctc gtc     1201
Lys His Asn Leu Pro Tyr Arg Asn Pro Leu Pro His Glu Gly Leu Val
385                 390                 395                 400

atc ctg ctc cga tac ctg tcc cag ttc gct cga atg gcc gag aag cag     1249
Ile Leu Leu Arg Tyr Leu Ser Gln Phe Ala Arg Met Ala Glu Lys Gln
                405                 410                 415

ccc ggt gcc aag gct cag taa gc                                      1272
Pro Gly Ala Lys Ala Gln
            420
```

```
<210> SEQ ID NO 41
<211> LENGTH: 422
<212> TYPE: PRT
<213> ORGANISM: Artificial Sequence
<220> FEATURE:
<223> OTHER INFORMATION: Synthetic Construct
```

<400> SEQUENCE: 41

```
Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415
```

```
Pro Gly Ala Lys Ala Gln
            420


<210> SEQ ID NO 42
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: delta-9 elongase
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(777)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 2007-0117190-A1
<311> PATENT FILING DATE: 2006-11-16
<312> PUBLICATION DATE: 2007-05-24
<313> RELEVANT RESIDUES IN SEQ ID NO: (1)..(777)

<400> SEQUENCE: 42

atg gag gtg gtg aat gaa ata gtc tca att ggg cag gaa gtt tta ccc       48
Met Glu Val Val Asn Glu Ile Val Ser Ile Gly Gln Glu Val Leu Pro
1               5                   10                  15

aaa gtt gat tat gcc caa ctc tgg agt gat gcc agt cac tgt gag gtg       96
Lys Val Asp Tyr Ala Gln Leu Trp Ser Asp Ala Ser His Cys Glu Val
            20                  25                  30

ctt tac ttg tcc atc gca ttt gtc atc ttg aag ttc act ctt ggc ccc      144
Leu Tyr Leu Ser Ile Ala Phe Val Ile Leu Lys Phe Thr Leu Gly Pro
        35                  40                  45

ctt ggt cca aaa ggt cag tct cgt atg aag ttt gtt ttc acc aat tac      192
Leu Gly Pro Lys Gly Gln Ser Arg Met Lys Phe Val Phe Thr Asn Tyr
    50                  55                  60

aac ctt ctc atg tcc att tat tcg ttg gga tca ttc ctc tca atg gca      240
Asn Leu Leu Met Ser Ile Tyr Ser Leu Gly Ser Phe Leu Ser Met Ala
65                  70                  75                  80

tat gcc atg tac acc atc ggt gtt atg tct gac aac tgc gag aag gct      288
Tyr Ala Met Tyr Thr Ile Gly Val Met Ser Asp Asn Cys Glu Lys Ala
                85                  90                  95

ttt gac aac aac gtc ttc agg atc acc acg cag ttg ttc tat ttg agc      336
Phe Asp Asn Asn Val Phe Arg Ile Thr Thr Gln Leu Phe Tyr Leu Ser
            100                 105                 110

aag ttc ctg gag tat att gac tcc ttc tat ttg cca ctg atg ggc aag      384
Lys Phe Leu Glu Tyr Ile Asp Ser Phe Tyr Leu Pro Leu Met Gly Lys
        115                 120                 125

cct ctg acc tgg ttg caa ttc ttc cat cat ttg ggg gca ccg atg gat      432
Pro Leu Thr Trp Leu Gln Phe Phe His His Leu Gly Ala Pro Met Asp
    130                 135                 140

atg tgg ctg ttc tat aat tac cga aat gaa gct gtt tgg att ttt gtg      480
Met Trp Leu Phe Tyr Asn Tyr Arg Asn Glu Ala Val Trp Ile Phe Val
145                 150                 155                 160

ctg ttg aat ggt ttc atc cac tgg atc atg tac ggt tat tat tgg acc      528
Leu Leu Asn Gly Phe Ile His Trp Ile Met Tyr Gly Tyr Tyr Trp Thr
                165                 170                 175

aga ttg atc aag ctg aag ttc ccc atg cca aaa tcc ctg att aca tca      576
Arg Leu Ile Lys Leu Lys Phe Pro Met Pro Lys Ser Leu Ile Thr Ser
            180                 185                 190

atg cag atc att caa ttc aat gtt ggt ttc tac att gtc tgg aag tac      624
Met Gln Ile Ile Gln Phe Asn Val Gly Phe Tyr Ile Val Trp Lys Tyr
```

-continued

```
        195                 200                 205

agg aac att ccc tgt tat cgc caa gat ggg atg agg atg ttt ggc tgg      672
Arg Asn Ile Pro Cys Tyr Arg Gln Asp Gly Met Arg Met Phe Gly Trp
    210                 215                 220

ttc ttc aat tac ttt tat gtt ggc aca gtc ttg tgt ttg ttc ttg aat      720
Phe Phe Asn Tyr Phe Tyr Val Gly Thr Val Leu Cys Leu Phe Leu Asn
225                 230                 235                 240

ttc tat gtg caa acg tat atc gtc agg aag cac aag gga gcc aaa aag      768
Phe Tyr Val Gln Thr Tyr Ile Val Arg Lys His Lys Gly Ala Lys Lys
                245                 250                 255

att cag tga                                                          777
Ile Gln


<210> SEQ ID NO 43
<211> LENGTH: 258
<212> TYPE: PRT
<213> ORGANISM: Euglena gracilis

<400> SEQUENCE: 43

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln


<210> SEQ ID NO 44
<211> LENGTH: 8357
<212> TYPE: DNA
<213> ORGANISM: Artificial Sequence
```

-continued

<220> FEATURE:
<223> OTHER INFORMATION: Plasmid pZUFmEaD5S

<400> SEQUENCE: 44

```
catggccacc atctccctga ctaccgagca gctcctggaa caccccgagc tcgttgccat     60
cgacggagtc ctgtacgatc tcttcggtct ggccaaggtg catccaggag gcaacctcat    120
cgaagctgcc ggtgcatccg acggaaccgc tctgttctac tccatgcatc ctggagtcaa    180
gccagagaac tcgaagcttc tgcagcaatt tgcccgaggc aagcacgaac gaagctccaa    240
ggatcccgtg tacaccttcg actctccctt tgctcaggac gtcaagcagt ccgttcgaga    300
ggtcatgaag ggtcgaaact ggtacgccac tcctggcttc tggctgagaa ccgcactcat    360
catcgcttgt actgccattg gcgagtggta ctggatcaca accggagcag tgatgtgggg    420
tatctttact ggatacttcc actcgcagat tggcttggcc attcaacacg atgcttctca    480
cggagccatc agcaaaaagc cctgggtcaa cgcctttttc gcttatggca tcgacgccat    540
tggttcctct cgttggatct ggctgcagtc ccacattatg cgacatcaca cttacaccaa    600
ccagcatggc ctcgacctgg atgctgcctc ggcagagccg ttcatcttgt tccactccta    660
tcctgctacc aacgcctctc gaaagtggta ccaccgattt caggcgtggt acatgtacat    720
cgttctggga atgtatggtg tctcgatggt gtacaatccc atgtacctct tcacaatgca    780
gcacaacgac accattcccg aggccacttc tctcagacca ggcagctttt tcaatcggca    840
gcgagctttc gccgtttccc ttcgactgct cttcatcttc cgaaacgcct ttcttccctg    900
gtacattgct ggtgcctctc ctctgctcac cattcttctg gtgcccacgg tcacaggcat    960
cttcctcacc tttgtgttcg ttctgtccca taacttcgag ggagccgaac ggaccccaga   1020
gaagaactgc aaggccaaac gagctaagga aggcaaggag gtcagagacg tggaagagga   1080
tcgagtcgac tggtaccgag cacaggccga gactgctgcc acctacggtg gcagcgtggg   1140
aatgatgctt acaggcggtc tcaacctgca gatcgagcat cacttgtttc cccgaatgtc   1200
ctcttggcac tatcccttca ttcaagacac cgttcgggag tgttgcaagc gacatggcgt   1260
ccgttacaca tactatccta ccattctcga gaacatcatg tccactcttc gatacatgca   1320
gaaggtgggt gttgctcaca ccattcagga tgcccaggag ttctaagcgg ccgcaagtgt   1380
ggatggggaa gtgagtgccc ggttctgtgt gcacaattgg caatccaaga tggatggatt   1440
caacacaggg atatagcgag ctacgtggtg gtgcgaggat atagcaacgg atatttatgt   1500
ttgacacttg agaatgtacg atacaagcac tgtccaagta caatactaaa catactgtac   1560
atactcatac tcgtacccgg gcaacggttt cacttgagtg cagtggctag tgctcttact   1620
cgtacagtgt gcaatactgc gtatcatagt ctttgatgta tatcgtattc attcatgtta   1680
gttgcgtacg agccggaagc ataaagtgta aagcctgggg tgcctaatga gtgagctaac   1740
tcacattaat tgcgttgcgc tcactgcccg ctttccagtc gggaaacctg tcgtgccagc   1800
tgcattaatg aatcggccaa cgcgcgggga gaggcggttt gcgtattggg cgctcttccg   1860
cttcctcgct cactgactcg ctgcgctcgg tcgttcggct gcggcgagcg gtatcagctc   1920
actcaaaggc ggtaatacgg ttatccacag aatcagggga taacgcagga aagaacatgt   1980
gagcaaaagg ccagcaaaag gccaggaacc gtaaaaaggc cgcgttgctg gcgtttttcc   2040
ataggctccg cccccctgac gagcatcaca aaaatcgacg ctcaagtcag aggtggcgaa   2100
acccgacagg actataaaga taccaggcgt ttccccctgg aagctccctc gtgcgctctc   2160
ctgttccgac cctgccgctt accggatacc tgtccgcctt tctcccttcg ggaagcgtgg   2220
cgctttctca tagctcacgc tgtaggtatc tcagttcggt gtaggtcgtt cgctccaagc   2280
```

-continued

```
tgggctgtgt gcacgaaccc cccgttcagc ccgaccgctg cgccttatcc ggtaactatc   2340
gtcttgagtc caacccggta agacacgact tatcgccact ggcagcagcc actggtaaca   2400
ggattagcag agcgaggtat gtaggcggtg ctacagagtt cttgaagtgg tggcctaact   2460
acggctacac tagaaggaca gtatttggta tctgcgctct gctgaagcca gttaccttcg   2520
gaaaaagagt tggtagctct tgatccggca aacaaaccac cgctggtagc ggtggttttt   2580
ttgtttgcaa gcagcagatt acgcgcagaa aaaaaggatc tcaagaagat cctttgatct   2640
tttctacggg gtctgacgct cagtggaacg aaaactcacg ttaagggatt ttggtcatga   2700
gattatcaaa aaggatcttc acctagatcc ttttaaatta aaaatgaagt tttaaatcaa   2760
tctaaagtat atatgagtaa acttggtctg acagttacca atgcttaatc agtgaggcac   2820
ctatctcagc gatctgtcta tttcgttcat ccatagttgc ctgactcccc gtcgtgtaga   2880
taactacgat acgggagggc ttaccatctg gccccagtgc tgcaatgata ccgcgagacc   2940
cacgctcacc ggctccagat ttatcagcaa taaaccagcc agccggaagg gccgagcgca   3000
gaagtggtcc tgcaacttta tccgcctcca tccagtctat taattgttgc cgggaagcta   3060
gagtaagtag ttcgccagtt aatagtttgc gcaacgttgt tgccattgct acaggcatcg   3120
tggtgtcacg ctcgtcgttt ggtatggctt cattcagctc cggttcccaa cgatcaaggc   3180
gagttacatg atcccccatg ttgtgcaaaa aagcggttag ctccttcggt cctccgatcg   3240
ttgtcagaag taagttggcc gcagtgttat cactcatggt tatggcagca ctgcataatt   3300
ctcttactgt catgccatcc gtaagatgct tttctgtgac tggtgagtac tcaaccaagt   3360
cattctgaga atagtgtatg cggcgaccga gttgctcttg cccggcgtca atacgggata   3420
ataccgcgcc acatagcaga actttaaaag tgctcatcat tggaaaacgt tcttcggggc   3480
gaaaactctc aaggatctta ccgctgttga gatccagttc gatgtaaccc actcgtgcac   3540
ccaactgatc ttcagcatct tttactttca ccagcgtttc tgggtgagca aaaacaggaa   3600
ggcaaaatgc cgcaaaaaag ggaataaggg cgacacggaa atgttgaata ctcatactct   3660
tcctttttca atattattga agcatttatc agggttattg tctcatgagc ggatacatat   3720
ttgaatgtat ttagaaaaat aaacaaatag gggttccgcg cacatttccc cgaaaagtgc   3780
cacctgacgc gccctgtagc ggcgcattaa gcgcggcggg tgtggtggtt acgcgcagcg   3840
tgaccgctac acttgccagc gccctagcgc ccgctccttt cgctttcttc ccttcctttc   3900
tcgccacgtt cgccggcttt ccccgtcaag ctctaaatcg ggggctccct ttagggttcc   3960
gatttagtgc tttacggcac ctcgacccca aaaaacttga ttagggtgat ggttcacgta   4020
gtgggccatc gccctgatag acggtttttc gccctttgac gttggagtcc acgttcttta   4080
atagtggact cttgttccaa actggaacaa cactcaaccc tatctcggtc tattcttttg   4140
atttataagg gattttgccg atttcggcct attggttaaa aaatgagctg atttaacaaa   4200
aatttaacgc gaattttaac aaaatattaa cgcttacaat ttccattcgc cattcaggct   4260
gcgcaactgt tgggaagggc gatcggtgcg ggcctcttcg ctattacgcc agctggcgaa   4320
agggggatgt gctgcaaggc gattaagttg ggtaacgcca gggttttccc agtcacgacg   4380
ttgtaaaacg acggccagtg aattgtaata cgactcacta tagggcgaat tgggtaccgg   4440
gccccccctc gaggtcgatg gtgtcgataa gcttgatatc gaattcatgt cacacaaacc   4500
gatcttcgcc tcaaggaaac ctaattctac atccgagaga ctgccgagat ccagtctaca   4560
ctgattaatt ttcgggccaa taatttaaaa aaatcgtgtt atataatatt atatgtatta   4620
tatatataca tcatgatgat actgacagtc atgtcccatt gctaaataga cagactccat   4680
```

-continued

```
ctgccgcctc caactgatgt tctcaatatt taaggggtca tctcgcattg tttaataata   4740
aacagactcc atctaccgcc tccaaatgat gttctcaaaa tatattgtat gaacttattt   4800
ttattactta gtattattag acaacttact tgctttatga aaaacacttc ctatttagga   4860
aacaatttat aatggcagtt cgttcattta acaatttatg tagaataaat gttataaatg   4920
cgtatgggaa atcttaaata tggatagcat aaatgatatc tgcattgcct aattcgaaat   4980
caacagcaac gaaaaaaatc ccttgtacaa cataaatagt catcgagaaa tatcaactat   5040
caaagaacag ctattcacac gttactattg agattattat tggacgagaa tcacacactc   5100
aactgtcttt ctctcttcta gaaatacagg tacaagtatg tactattctc attgttcata   5160
cttctagtca tttcatccca catattcctt ggatttctct ccaatgaatg acattctatc   5220
ttgcaaattc aacaattata ataagatata ccaaagtagc ggtatagtgg caatcaaaaa   5280
gcttctctgg tgtgcttctc gtatttattt ttattctaat gatccattaa aggtatatat   5340
ttatttcttg ttatataatc cttttgttta ttacatgggc tggatacata aaggtatttt   5400
gatttaattt tttgcttaaa ttcaatcccc cctcgttcag tgtcaactgt aatggtagga   5460
aattaccata cttttgaaga agcaaaaaaa atgaaagaaa aaaaaaatcg tatttccagg   5520
ttagacgttc cgcagaatct agaatgcggt atgcggtaca ttgttcttcg aacgtaaaag   5580
ttgcgctccc tgagatattg tacatttttg cttttacaag tacaagtaca tcgtacaact   5640
atgtactact gttgatgcat ccacaacagt ttgttttgtt tttttttgtt tttttttttt   5700
ctaatgattc attaccgcta tgtataccta cttgtacttg tagtaagccg ggttattggc   5760
gttcaattaa tcatagactt atgaatctgc acggtgtgcg ctgcgagtta cttttagctt   5820
atgcatgcta cttgggtgta atattgggat ctgttcggaa atcaacggat gctcaatcga   5880
tttcgacagt aattaattaa gtcatacaca agtcagcttt cttcgagcct catataagta   5940
taagtagttc aacgtattag cactgtaccc agcatctccg tatcgagaaa cacaacaaca   6000
tgccccattg gacagatcat gcggatacac aggttgtgca gtatcataca tactcgatca   6060
gacaggtcgt ctgaccatca tacaagctga acaagcgctc catacttgca cgctctctat   6120
atacacagtt aaattacata tccatagtct aacctctaac agttaatctt ctggtaagcc   6180
tcccagccag ccttctggta tcgcttggcc tcctcaatag gatctcggtt ctggccgtac   6240
agacctcggc cgacaattat gatatccgtt ccggtagaca tgacatcctc aacagttcgg   6300
tactgctgtc cgagagcgtc tcccttgtcg tcaagaccca ccccgggggt cagaataagc   6360
cagtcctcag agtcgccctt aggtcggttc tgggcaatga agccaaccac aaactcgggg   6420
tcggatcggg caagctcaat ggtctgcttg gagtactcgc cagtggccag agagcccttg   6480
caagacagct cggccagcat gagcagacct ctggccagct tctcgttggg agaggggact   6540
aggaactcct tgtactggga gttctcgtag tcagagacgt cctccttctt ctgttcagag   6600
acagtttcct cggcaccagc tcgcaggcca gcaatgattc cggttccggg tacaccgtgg   6660
gcgttggtga tatcggacca ctcggcgatt cggtgacacc ggtactggtg cttgacagtg   6720
ttgccaatat ctgcgaactt tctgtcctcg aacaggaaga aaccgtgctt aagagcaagt   6780
tccttgaggg ggagcacagt gccggcgtag gtgaagtcgt caatgatgtc gatatgggtt   6840
ttgatcatgc acacataagg tccgacctta tcggcaagct caatgagctc cttggtggtg   6900
gtaacatcca gagaagcaca caggttggtt ttcttggctg ccacgagctt gagcactcga   6960
gcggcaaagg cggacttgtg gacgttagct cgagcttcgt aggagggcat tttggtggtg   7020
aagaggagac tgaaataaat ttagtctgca gaacttttta tcggaacctt atctggggca   7080
```

-continued

```
gtgaagtata tgttatggta atagttacga gttagttgaa cttatagata gactggacta   7140
tacggctatc ggtccaaatt agaaagaacg tcaatggctc tctgggcgtc gcctttgccg   7200
acaaaaatgt gatcatgatg aaagccagca atgacgttgc agctgatatt gttgtcggcc   7260
aaccgcgccg aaaacgcagc tgtcagaccc acagcctcca acgaagaatg tatcgtcaaa   7320
gtgatccaag cacactcata gttggagtcg tactccaaag gcggcaatga cgagtcagac   7380
agatactcgt cgacgtttaa acagtgtacg cagatctact atagaggaac atttaaattg   7440
ccccggagaa gacggccagg ccgcctagat gacaaattca acaactcaca gctgactttc   7500
tgccattgcc actagggggg ggccttttta tatggccaag ccaagctctc cacgtcggtt   7560
gggctgcacc caacaataaa tgggtagggt tgcaccaaca aagggatggg atgggggta    7620
gaagatacga ggataacggg gctcaatggc acaaataaga acgaatactg ccattaagac   7680
tcgtgatcca gcgactgaca ccattgcatc atctaagggc ctcaaaacta cctcggaact   7740
gctgcgctga tctggacacc acagaggttc cgagcacttt aggttgcacc aaatgtccca   7800
ccaggtgcag gcagaaaacg ctggaacagc gtgtacagtt tgtcttaaca aaaagtgagg   7860
gcgctgaggt cgagcagggt ggtgtgactt gttatagcct ttagagctgc gaaagcgcgt   7920
atggatttgg ctcatcaggc cagattgagg gtctgtggac acatgtcatg ttagtgtact   7980
tcaatcgccc cctggatata gccccgacaa taggccgtgg cctcattttt ttgccttccg   8040
cacatttcca ttgctcgata cccacacctt gcttctcctg cacttgccaa ccttaatact   8100
ggtttacatt gaccaacatc ttacaagcgg ggggcttgtc tagggtatat ataaacagtg   8160
gctctcccaa tcggttgcca gtctcttttt tcctttcttt ccccacagat tcgaaatcta   8220
aactacacat cacagaattc cgagccgtga gtatccacga caagatcagt gtcgagacga   8280
cgcgttttgt gtaatgacac aatccgaaag tcgctagcaa cacacactct ctacacaaac   8340
taacccagct ctggtac                                                  8357
```

Δ-5 DESATURASES AND THEIR USE IN MAKING POLYUNSATURATED FATTY ACIDS

This application claims the benefit of U.S. Provisional Patent Application No. 60/915,733, filed May 3, 2007 which is incorporated herein by reference in its entirety.

FIELD OF THE INVENTION

This invention is in the field of biotechnology. More specifically, this invention pertains to the identification of polynucleotide sequences encoding Δ5 fatty acid desaturases and the use of these desaturases in making long-chain polyunsaturated fatty acids (PUFAs).

BACKGROUND OF THE INVENTION

Today, a variety of different hosts including plants, algae, fungi, stramenopiles and yeast are being investigated as means for commercial PUFA production. Genetic engineering has demonstrated that the natural abilities of some hosts (even those natively limited to linoleic acid (LA; 18:2 ω-6) and α-linolenic acid (ALA; 18:3 ω-3) fatty acid production) can be substantially altered to result in high-level production of various long-chain ω-3/ω-6 PUFAs. Whether this is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) may all require expression of a Δ5 desaturase.

Most Δ5 desaturase enzymes identified thus far have the primary ability to convert dihomo-γ-linolenic acid (DGLA; 20:3 ω-6) to ARA, with secondary activity in converting eicosatetraenoic acid (ETA; 20:4 ω-3) to EPA (where DHA is subsequently synthesized from EPA following reaction with an additional $C_{20/22}$ elongase and a Δ4 desaturase). The Δ5 desaturase has a role in both the Δ6 desaturase/Δ6 elongase pathway (which is predominantly found in algae, mosses, fungi, nematodes and humans and which is characterized by the production of γ-linolenic acid (GLA; 18:3 ω-6) and/or stearidonic acid (STA; 18:4 ω-3)) and the Δ9 elongase/Δ8 desaturase pathway (which operates in some organisms, such as euglenoid species and which is characterized by the production of eicosadienoic acid (EDA; 20:2 ω-6) and/or eicosatrienoic acid (ETrA; 20:3 ω-3)) (FIG. 1).

Based on the role Δ5 desaturase enzymes play in the synthesis of e.g., ARA, EPA and DHA, there has been considerable effort to identify and characterize these enzymes from various sources. As such, numerous Δ5 desaturases have been disclosed in both the open literature (e.g., GenBank Accession Nos. AF199596, AF226273, AF320509, AB072976, AF489588, AJ510244, AF419297, AF078796, AF067654 and AB022097) and the patent literature (e.g., U.S. Pat. No. 5,972,664 and U.S. Pat. No. 6,075,183). Also, commonly owned, co-pending applications having application Ser. No. 11/748,629 and Ser. No. 11/749,889 (filed May 17, 2007) disclose amino acid and nucleic acid sequences for a Δ5 desaturase enzyme from *Euglena gracilis* (see also Patent Publication US-2007-0277266-Δ1), while commonly owned, co-pending applications having application Ser. No. 11/748,637 and Ser. No. 11/749,859 (filed May 17, 2007) disclose amino acid and nucleic acid sequences for a Δ5 desaturase enzyme from *Peridium* sp. CCMP626 (see also Patent Publication US-2007-0271632-A1).

Although genes encoding Δ5 desaturases are known there is a need for additional varieties of these enzymes with varying enzymatic properties that are suitable for heterologous expression in a variety of host organisms for use in the production of ω-3/ω-6 fatty acids. Applicants have addressed the stated need by isolating genes encoding Δ5 desaturases from *Euglena anabaena.*

SUMMARY OF THE INVENTION

The present invention relates to new genetic constructs encoding polypeptides having Δ5 desaturase activity, and their use in algae, bacteria, yeast, euglenoids, stramenopiles and fungi for the production of PUFAs. Accordingly the invention provides A microbial host cell comprising an isolated polynucleotide comprising:

(a) a nucleotide sequence encoding a polypeptide having Δ5 desaturase activity, wherein the polypeptide has at least 80% amino acid identity, based on the Clustal V method of alignment, when compared to an amino acid sequence as set forth in SEQ ID NO:13;

(b) a nucleotide sequence encoding a polypeptide having Δ5 desaturase activity, wherein the nucleotide sequence has at least 80% sequence identity, based on the BLASTN method of alignment, when compared to a nucleotide sequence as set forth in SEQ ID NO:12 or SEQ ID NO:25;

(c) a nucleotide sequence encoding a polypeptide having Δ5 desaturase activity, wherein the nucleotide sequence hybridizes under stringent conditions to a nucleotide sequence as set forth in SEQ ID NO:12 or SEQ ID NO:25; or, (d) a complement of the nucleotide sequence of (a), (b) or (c), wherein the complement and the nucleotide sequence consist of the same number of nucleotides and are 100% complementary.

In another embodiment the invention provides a method for the production of arachidonic acid comprising:

a) providing a microbial host cell comprising:
  (i) a recombinant nucleotide molecule encoding a Δ5 desaturase polypeptide having at least 80% amino acid identity when compared to a polypeptide having the amino acid sequence as set forth in SEQ ID NO:13, based on the Clustal V method of alignment; and,
  (ii) a source of dihomo-γ-linolenic acid;
b) growing the microbial host cell of step (a) under conditions wherein the nucleic acid fragment encoding the Δ5 desaturase polypeptide is expressed and the dihomo-γ-linolenic acid is converted to arachidonic acid; and,
c) optionally recovering the arachidonic acid of step (b).

In an alternate embodiment the invention provides a method for the production of eicosapentaenoic acid comprising:

a) providing a microbial host cell comprising:
  (i) a recombinant nucleotide molecule encoding a Δ5 desaturase polypeptide having at least 80% amino acid identity when compared to a polypeptide having the amino acid sequence as set forth in SEQ ID NO:13, based on the Clustal V method of alignment; and,
  (ii) a source of eicosatetraenoic acid;
b) growing the microbial host cell of step (a) under conditions wherein the nucleic acid fragment encoding the Δ5 desaturase polypeptide is expressed and the eicosatetraenoic acid is converted to eicosapentaenoic acid; and,
c) optionally recovering the eicosapentaenoic acid of step (b).

In an additional embodiment the invention provides An isolated nucleic acid molecule which encodes a Δ5 desaturase as set forth in SEQ ID NO:25 wherein at least 174 codons are codon-optimized for expression in *Yarrowia* sp.

BRIEF DESCRIPTION OF THE DRAWINGS AND SEQUENCE LISTINGS

FIG. 1 is a representative ω-3 and ω-6 fatty acid biosynthetic pathway providing for the conversion of myristic acid through various intermediates to DHA.

FIG. 2A diagrams the development of *Yarrowia lipolytica* strain Y4036U, producing about 18% DGLA in the total lipid fraction. FIG. 2B provides the plasmid map for pZKLeuN-29E3.

FIG. 3 provides plasmid maps for the following: (A) pY116; and, (B) pKO2UF8289.

FIG. 5B is a plasmid map of pZUF17, while

FIG. 6 provides plasmid maps for the following: (A) pY115 (SEQ ID NO:19); (B) pY159 (SEQ ID NO:23); and, (C) pY169 (SEQ ID NO:24).

FIG. 7 provides the fatty acid profiles for *Yarrowia lipolytica* expressing pY169 (SEQ ID NO:24; comprising EaD5Des1) and fed various substrates.

Figure 8A:
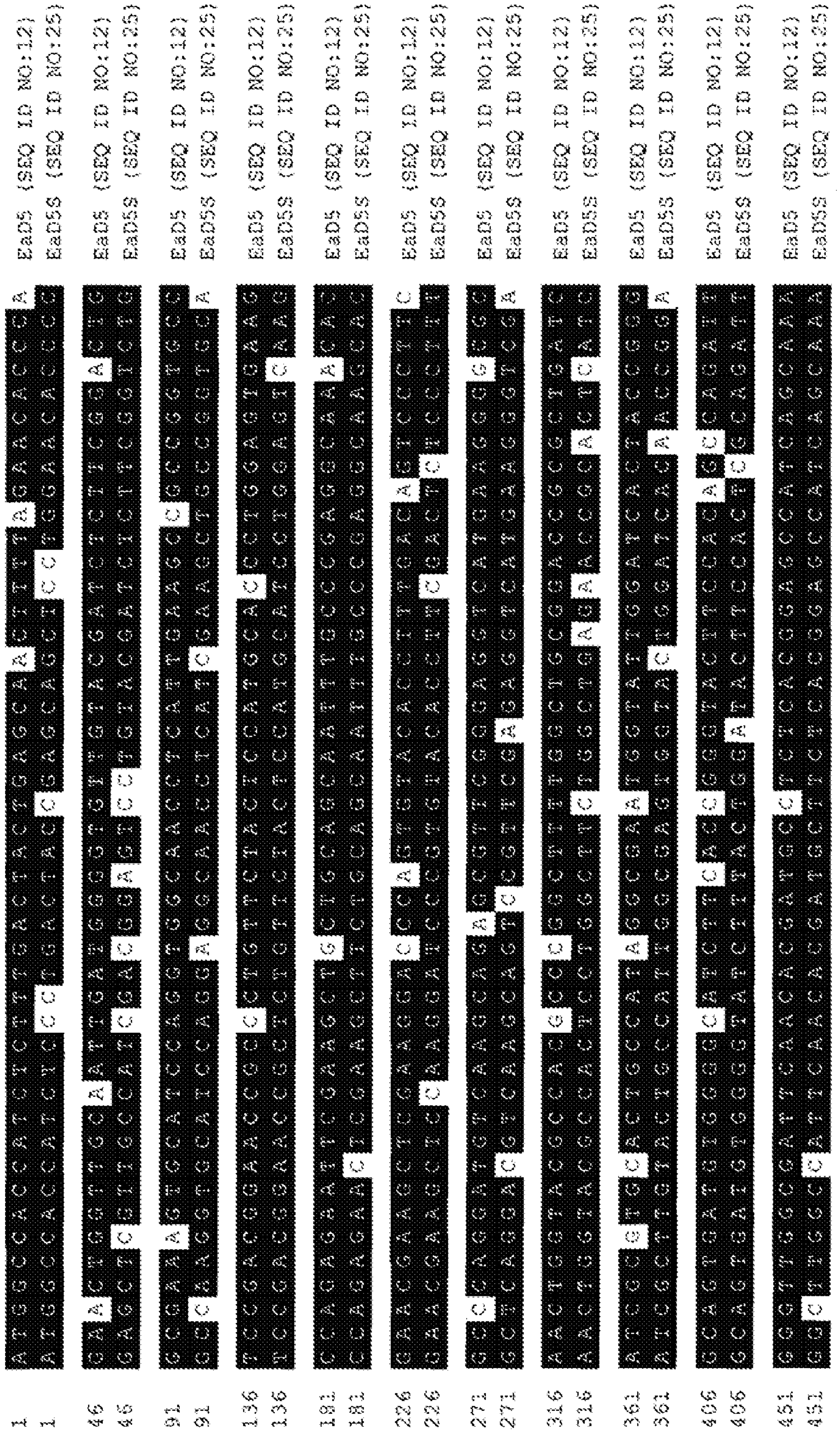
Figure 8B:
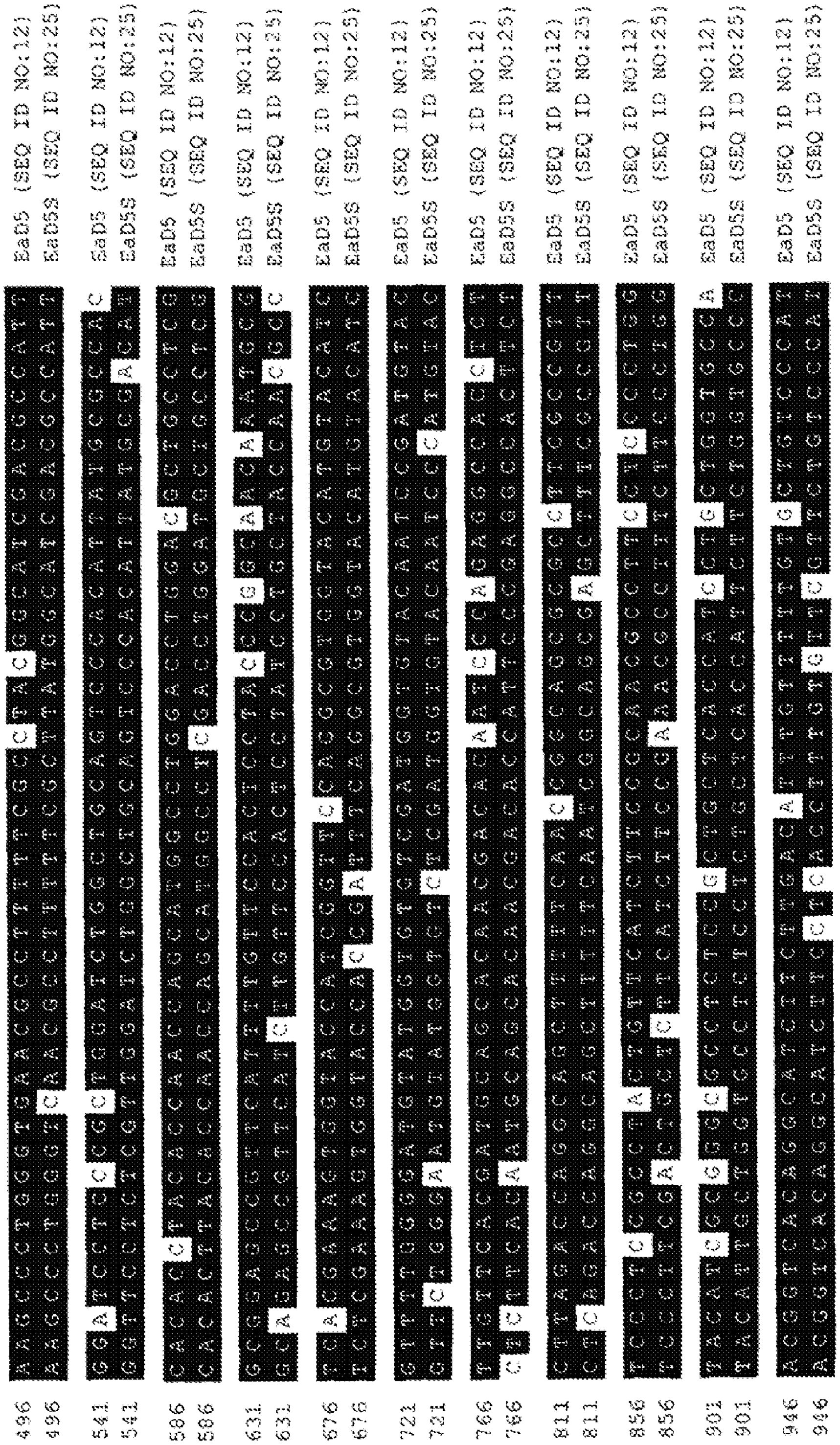
Figure 8C:
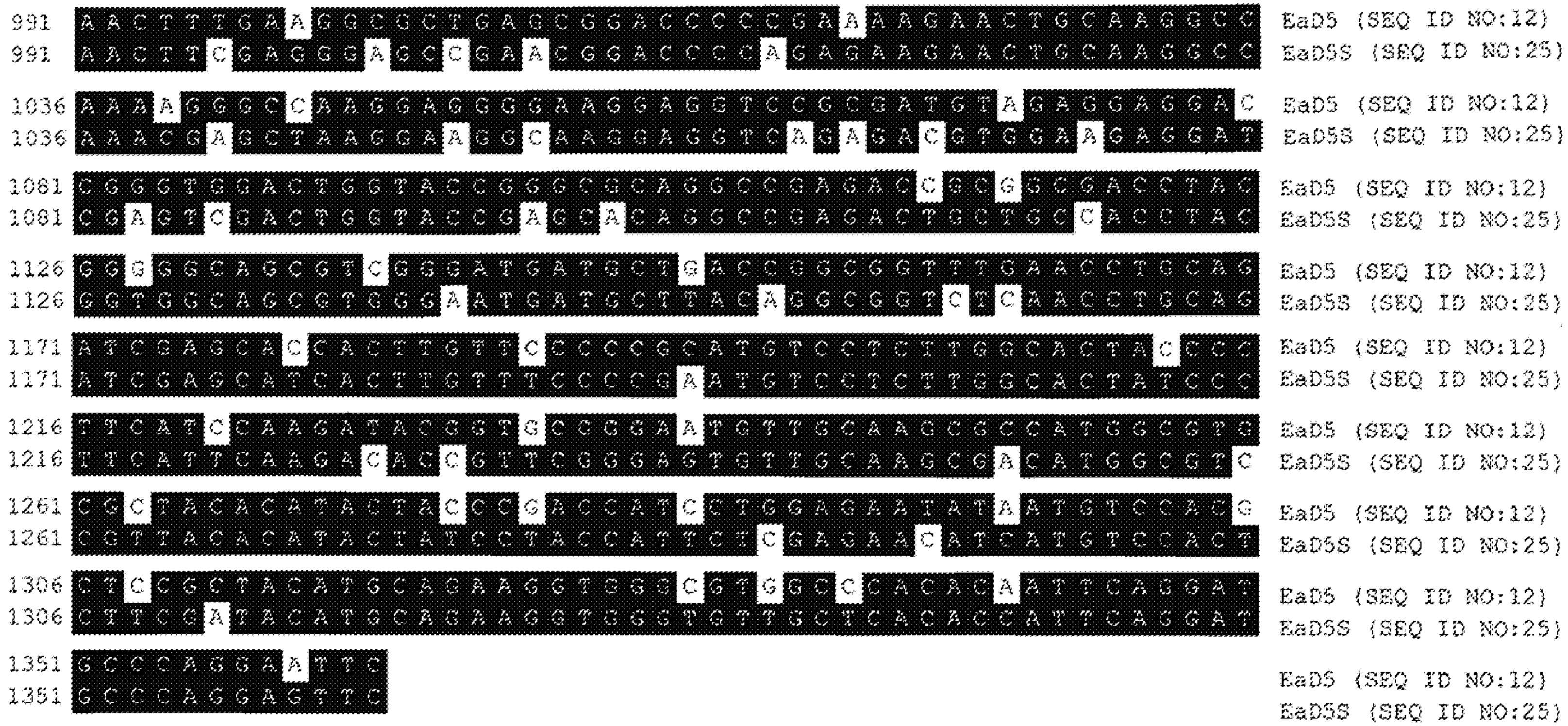

FIGS. 8A, 8B and 8C show a comparison of the nucleotide sequences of the *Euglena anabaena* Δ5 desaturase gene (designated as "EaD5" or "EaD5Des1"; SEQ ID NO:12) and the synthetic gene (designated as "EaD5S"; SEQ ID NO:25) codon-optimized for expression in *Yarrowia lipolytica.*

FIG. 9 provides plasmid maps for the following: (A) pEaD5S (SEQ ID NO:27); and, (B) pZUFmEaD5S (SEQ ID NO:44).

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-3, 8, 9, 12-19 and 22-44 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Euglena gracilis* Δ5 desaturase ("EgD5") | 1 (1350 bp) | 2 (449 AA) |
| *Euglena anabaena* Δ5 desaturase 1 cDNA sequence ("EaD5Des1" or "EaD5") | 3 (1524 bp) | — |
| Plasmid pZUF17 | 8 (8165 bp) | — |
| Plasmid pDMW367 | 9 (8438 bp) | — |
| *Euglena anabaena* Δ5 desaturase 1 coding sequence ("EaD5Des1" or "EaD5") | 12 (1362 bp) | 13 (454 AA) |
| Plasmid pLF119 | 14 (4276 bp) | — |
| *Thalassiosira pseudonana* Δ8 sphingolipid desaturase (GenBank Accession No. AAX14502) | — | 15 (476 AA) |
| *Phaeodactylum tricornutum* Δ5 desaturase (GenBank Accession No. AAL92562) | — | 16 (469 AA) |
| Plasmid pDMW263 | 17 (9472 bp) | — |
| Plasmid pDMW237 | 18 (7879 bp) | — |
| Plasmid pY115 | 19 (7783 bp) | — |
| Plasmid pY158 | 22 (6992 bp) | — |
| Plasmid pY159 | 23 (8707 bp) | — |
| Plasmid pY169 | 24 (8827 bp) | — |
| Synthetic Δ5 desaturase, derived from *Euglena anabaena*, codon-optimized for expression in *Yarrowia lipolytica* ("EaD5S") | 25 (1362 bp) | 26 (454 AA) |
| Plasmid pEaD5S | 27 (3983 bp) | — |
| Plasmid pZKLeuN-29E3 | 28 (14,688 bp) | — |
| *Fusarium moniliforme* Δ12 desaturase ("FmD12") | 29 (1434 bp) | 30 (477 AA) |
| Synthetic Δ9 elongase derived from *Euglena gracilis*, codon-optimized for expression in *Yarrowia lipolytica* ("EgD9eS") | 31 (777 bp) | 32 (258 AA) |
| *Escherichia coli* LoxP recombination site, recognized by a Cre recombinase enzyme | 33 (34 bp) | — |
| Synthetic $C_{16/18}$ elongase derived from *Mortierella alpina* ELO3, codon-optimized for expression in *Yarrowia lipolytica* ("ME3S") | 34 (828 bp) | 35 (275 AA) |
| Plasmid pY116 | 36 (8739 bp) | — |
| Plasmid pKO2UF8289 | 37 (15,337 bp) | — |
| *Yarrowia lipolytica* Δ12 desaturase ("YlD12") | 38 (1936 bp) | 39 (419 AA) |
| Synthetic mutant Δ8 desaturase ("EgD8M"; U.S. Patent Application No. 11/635,258), derived from *Euglena gracilis* ("EgD8S"; U.S. Pat. No. 7,256,033) | 40 (1272 bp) | 41 (422 AA) |
| *Euglena gracilis* Δ9 elongase ("EgD9e") | 42 (777 bp) | 43 (258 AA) |
| Plasmid pZUFmEaD5S | 44 (8357 bp) | — |

SEQ ID NOs:4-7 correspond to oligonucleotide primers YL794, YL797, YL796 and YL795, respectively, used to amplify the *Euglena gracilis* Δ5 desaturase.

SEQ ID NOs:10 and 11 correspond to the M13F universal primer and primer M13-28Rev, respectively, used for end-sequencing of *Euglena anabaena* DNA inserts.

SEQ ID NOs:20 and 21 correspond to primers oYFBA1 and oYFBA1-6, respectively, used to amplify the FBAINm promoter from plasmid pY115.

DETAILED DESCRIPTION OF THE INVENTION

New *Euglena anabaena* Δ5 desaturase enzymes and genes encoding the same that may be used for the manipulation of biochemical pathways for the production of healthful PUFAs are disclosed herein.

PUFAs, or derivatives thereof, are used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

DEFINITIONS

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in U.S. Pat. No. 7,238,482.

Fatty acids are described herein by a simple notation system of "X:Y", where X is the total number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic:acid (18:0), oleic acid (18:1, 9c), petroselinic acid (18:1, 6c), LA (18:2, 9c, 12c), GLA (18:3, 6c,9c, 12c) and ALA (18:3, 9c,12c,15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9, 12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the remainder of the specification, and each compounds' chemical name.

TABLE 2

Nomenclature Of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | PA or Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA or ERA | cis-11,14,17-eicosatrienoic | 20:3 ω-3 |
| Eicosatetraenoic | ETA | cis-8,11,14,17-eicosatetraenoic | 20:4 ω-3 |
| Juniperonic | JUP | cis-5,11,14,17-eicosatetraenoic | 20:4b ω-3 |
| Eicosapentaenoic | EPA | cis-5,8,11,14,17-eicosapentaenoic | 20:5 ω-3 |
| Docosatrienoic | DRA | cis-10,13,16-docosatrienoic | 22:3 ω-6 |
| Docosatetraenoic | DTA | cis-7,10,13,16-docosatetraenoic | 22:4 ω-6 |
| Docosapentaenoic | DPAn-6 | cis-4,7,10,13,16-docosapentaenoic | 22:5 ω-6 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature (e.g., see PCT Publication No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a Δ9 elongase, a $C_{14/16}$ elongase, a $C_{16/18}$ elongase, a $C_{18/20}$ elongase, a $C_{20/22}$ elongase, a Δ4 desaturase, a Δ5 desaturase, a Δ6 desaturase, a Δ12 desaturase, a Δ15 desaturase, a Δ17 desaturase, a Δ9 desaturase and/or a Δ8 desaturase.

Figure 1A:
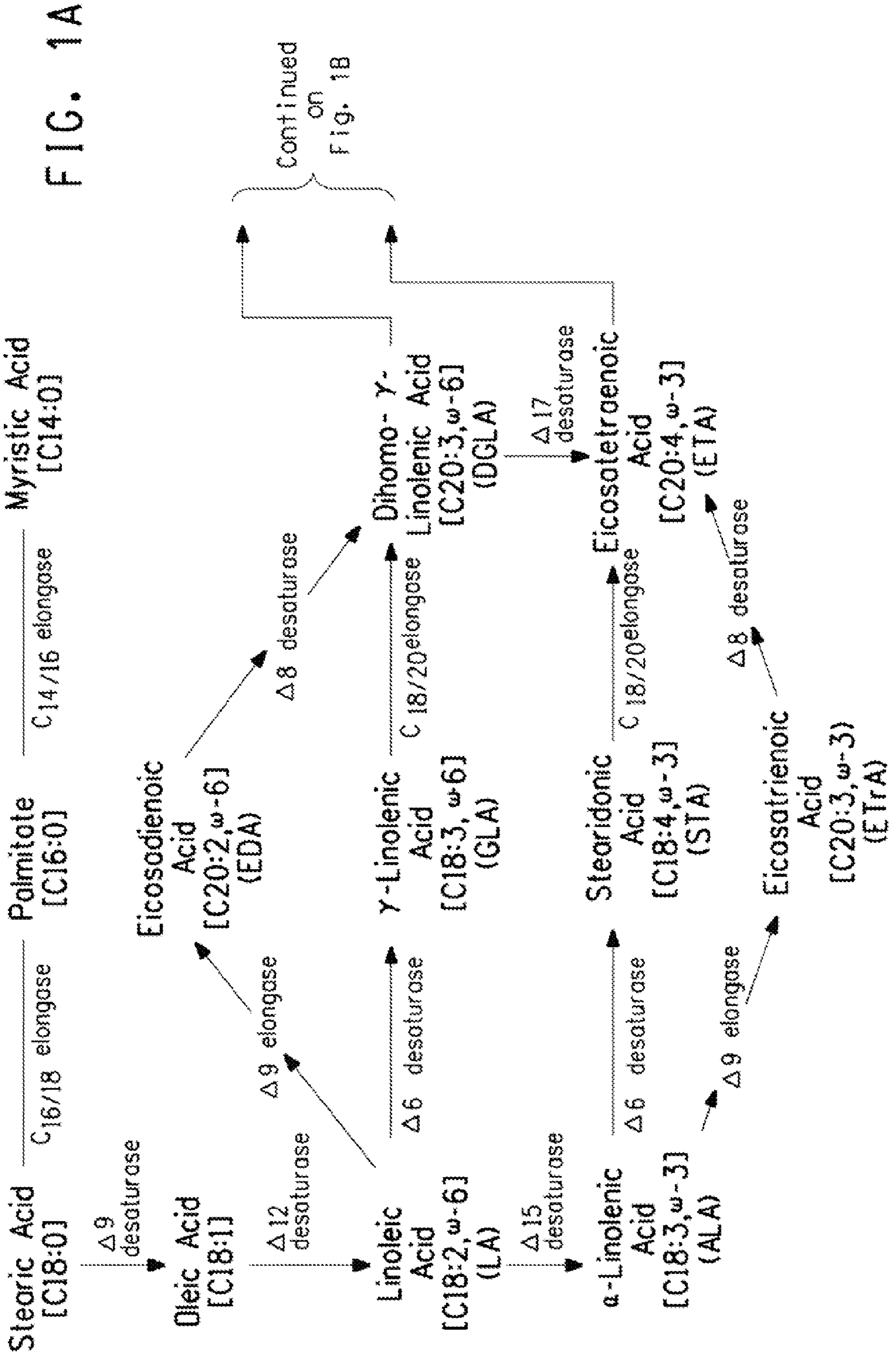
Figure 1B:
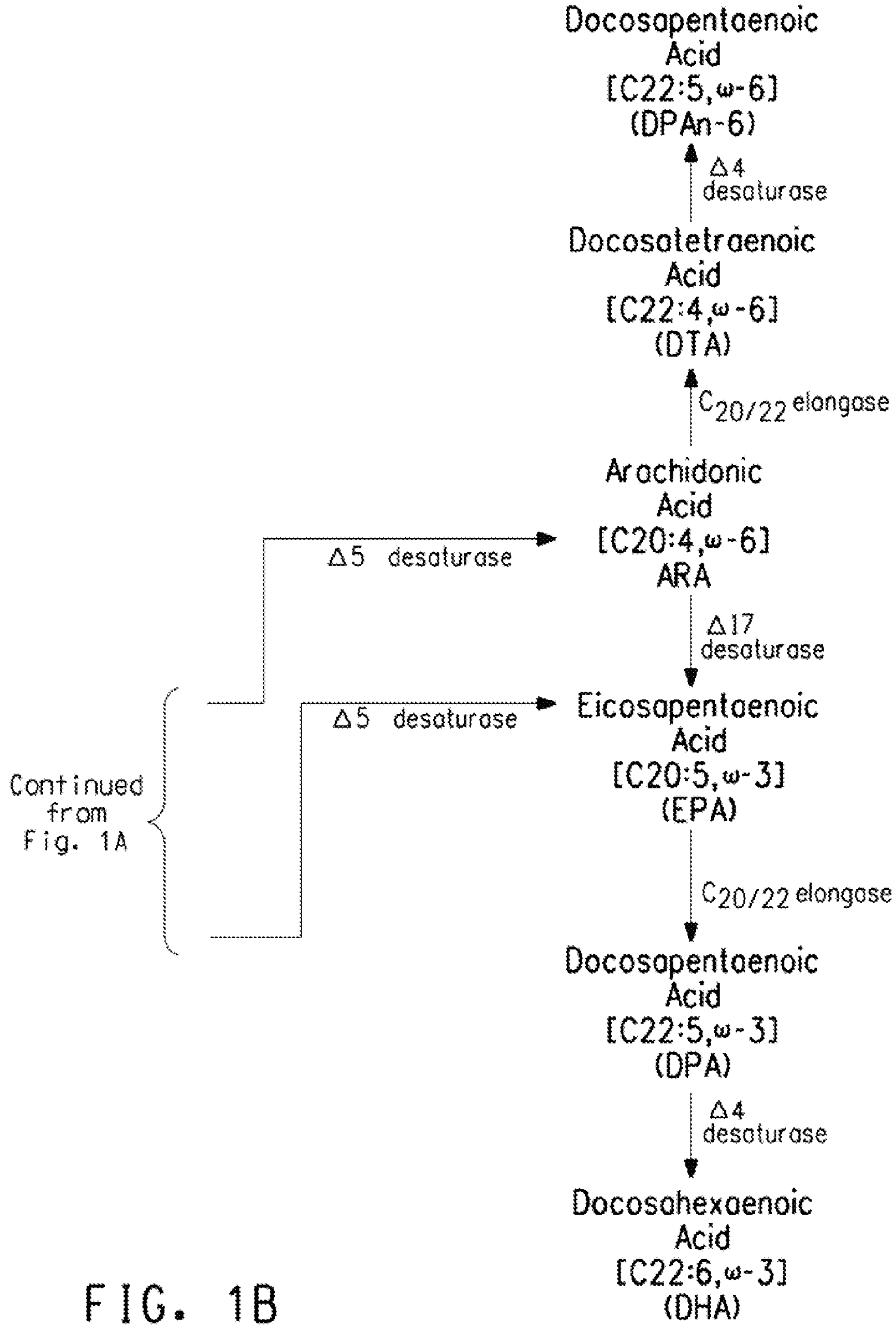

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, ω-6 fatty acids.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the PUFA biosynthetic pathway enzyme genes are required, as a number of fatty acid products will only require the expression of a subset of the genes of this pathway.

The term "Δ6 desaturase/Δ6 elongase pathway" will refer to a PUFA biosynthetic pathway that minimally includes at least one Δ6 desaturase and at least one $C_{18/20}$ elongase (also referred to as a Δ6 elongase), thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "Δ9 elongase/Δ8 desaturase pathway" will refer to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the Δ9 elongase/Δ8 desaturase pathway, sciadonic acid (SCI) and juniperonic acid (JUP) also can be produced by the action of a Δ5 desaturase on either EDA or ETrA, respectively. They are considered to be "by-product fatty acids" since neither can be further converted to EPA by the action of other metabolic pathway enzymes.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ5 desaturases that desaturate a fatty acid between the fifth and sixth carbon atom numbered from the carboxyl-terminal end of the molecule and that can, for example, catalyze the conversion of DGLA to ARA and/or ETA to EPA. Other fatty acid desaturases include, for example: (1) Δ8 desaturases that catalyze the conversion of EDA to DGLA and/or ERA to ETA; (2) Δ6 desaturases that catalyze the conversion of LA to GLA and/or ALA to STA; (3) Δ4 desaturases that catalyze the conversion of DPA to DHA and/or DTA to DPAn-6; (4) Δ12 desaturases that catalyze the conversion of oleic acid to LA; (5) Δ15 desaturases that catalyze the conversion of LA to ALA and/or GLA to STA; (6) Δ17 desaturases that catalyze the conversion of ARA to EPA and/or DGLA to ETA; and, (7) Δ9 desaturases that catalyze the conversion of palmitic acid to palmitoleic acid (16:1) and/or stearic acid to oleic acid (18:1). In the art, Δ15 and Δ17 desaturases are also occasionally referred to as "omega-3 desaturases", "ω-3 desaturases" and/or "ω-3 desaturases", based on their ability to convert ω-6 fatty acids into their ω-3 counterparts (e.g., conversion of LA into ALA and ARA into EPA, respectively). In some embodiments, it may be desirable to empirically determine the specificity of a particular fatty acid desaturase by transforming a suitable host with the gene for the fatty acid desaturase and determining its effect on the fatty acid profile of the host.

For the purposes herein, the terms "EaD5Des1" or "EaD5" refer to a Δ5 desaturase enzyme (SEQ ID NO:13) isolated from *Euglena anabaena*, encoded by SEQ ID NO:12 herein. Similarly, the term "EaD5S" refers to a synthetic Δ5 desaturase derived from *Euglena anabaena* that is codon-optimized for expression in *Yarrowia lipolytica* (i.e., SEQ ID NOs:25 and 26).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in U.S. Patent Publication No. 2005/0132442. Examples of reactions catalyzed by elongase systems are the conversion of GLA to DGLA, STA to ETA, LA to EDA, ALA to ETrA, ARA to DTA and EPA to DPA.

In general, the substrate selectivity of elongases is somewhat broad but segregated by both chain length and the degree of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., ARA, EPA). Similarly, a Δ9 elongase catalyzes the conversion of LA to EDA and/or ALA to ETrA. It is important to note that some elongases have broad specificity and thus a single enzyme may be capable of catalyzing several elongase reactions (e.g., thereby acting as both a $C_{16/18}$ elongase and a $C_{18/20}$ elongase). In preferred embodiments, it may be desirable to empirically determine the specificity of a fatty acid elongase by transforming a suitable host with the gene for the fatty acid elongase and determining its effect on the fatty acid profile of the host.

The term "oleaginous" refers to those organisms that tend to store their energy source in the form of lipid (Weete, In: Fungal Lipid Biochemistry, $2^{nd}$ Ed., Plenum, 1980). Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil.

The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ("euglenoids") found living in freshwater, marine, soil and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and refer to a polymer of RNA or DNA that is single- or double-stranded, optionally containing synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. U.S. Pat. No. 5,972,664 describes several distinct motifs that are associated with Δ5 desaturases.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the important factors being the ionic strength and temperature of the final wash solution. For DNA-DNA hybrids, the $T_m$ can be approximated from the equation of Meinkoth et al., *Anal. Biochem.,* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); and, low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and Current Protocols in Molecular Biology, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, CABIOS, 5:151-153 (1989); Higgins, D. G. et al., *Comput. Appl. Biosci.,* 8:189-191 (1992)) and found in the MegAlign™ program of the LASERGENE bioinformatics computing suite (supra). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant euglenoid polypeptide as set forth in SEQ ID NO:13. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed at almost all stages of development are commonly referred to as "constitutive promoters". It is further recognized that since in most cases the exact boundaries of regulatory sequences (especially at their 5' end) have not been completely defined, DNA fragments of some variation may have identical promoter activity.

A promoter sequence may consist of proximal and more distal upstream elements, the latter elements often referred to as enhancers and/or silencers. Accordingly, an "enhancer" is a DNA sequence that can stimulate promoter activity, and may be an innate element of the promoter or a heterologous element inserted to enhance the level or stage-specific activity of a promoter. A "silencer" is a DNA sequence that can repress promoter activity, and may be an innate element of the promoter or a heterologous element inserted to repress the level or stage-specific activity of a promoter.

"Translation leader sequence" refers to a polynucleotide sequence located between the transcription start site of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.,* 3:225-236 (1995)).

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA derived from the nucleic acid fragments of the invention. Expression may also refer to translation of mRNA into a protein (either precursor or mature).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: (1) a promoter sequence; (2) a coding sequence (i.e., ORF); and, (3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

A "recombinant DNA construct" (also referred to interchangeably herein as an "expression construct" or "construct") comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.,* 4:2411-2418 (1985); De Almeida et al., *Mol. Gen. Genetics,* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "introduced" means providing a nucleic acid (e.g., expression cassette) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct or expression cassette) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms or "recombinant" or "transformed" organisms.

As used herein, "transgenic" refers to a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression cassette. Transgenic is used herein to include any cell or cell line, the genotype of which has been altered by the presence of heterologous nucleic acids including those transgenics initially so altered as well as those created by mating of the initial transgenic with different mating types. The term "transgenic" as used herein does not encompass the alteration of the genome (chromosomal or extra-chromosomal) by naturally occurring events such as random cross-fertilization, non-recombinant viral infection, non-recombinant bacterial transformation, non-recombinant transposition, or spontaneous mutation.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987). Transformation methods are well known to those skilled in the art and are described infra.

An Overview: Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in U.S. Pat. No. 7,238, 482. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and, (4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ9 elongase/Δ8 desaturase pathway" and LA as substrate, long chain ω-6 fatty acids are formed as follows: (1) LA is converted to EDA by a Δ9 elongase; (2) EDA is converted to DGLA by a Δ8 desaturase; (3) DGLA is converted to ARA by a Δ5 desaturase; (4) ARA is converted to DTA by a $C_{20/22}$ elongase; and, (5) DTA is converted to DPAn-6 by a Δ4 desaturase. Alternatively, the "Δ9 elongase/Δ8 desaturase pathway" can use ALA as substrate to produce long chain ω-3 fatty acids as follows: (1) LA is converted to ALA, the first of the ω-3 fatty acids, by a Δ15 desaturase; (2) ALA is converted to ETrA by a Δ9 elongase; (3) ETrA is converted to ETA by a Δ8 desaturase; (4) ETA is converted to EPA by a Δ5 desaturase; (5) EPA is converted to DPA by a $C_{20/22}$ elongase; and, (6) DPA is converted to DHA by a Δ4 desaturase. Optionally, ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase (i.e., the "Δ6 desaturase/Δ6 elongase pathway"). More specifically, LA and ALA may be converted to GLA and STA, respectively, by a Δ6 desaturase; then, a $C_{18/20}$ elongase converts GLA to DGLA and/or STA to ETA. Downstream PUFAs are subsequently formed as described above.

It is contemplated that the particular functionalities required to be introduced into a specific host organism for production of ω-3/ω-6 fatty acids will depend on the host cell (and its native PUFA profile and/or desaturase/elongase profile), the availability of substrate, and the desired end product (s). For example, expression of the Δ9 elongase/Δ8 desaturase pathway may be preferred in some embodiments, as opposed to expression of the Δ6 desaturase/Δ6 elongase pathway, since PUFAs produced via the former pathway are devoid of GLA and/or STA.

One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; (4) co-factors required by the polypeptide; and/or, (5) whether the polypeptide was modified after its production (e.g., by a kinase or a prenyltransferase). The expressed polypeptide preferably has parameters compatible with the biochemical environment of its location in the host cell (see U.S. Pat. No. 7,238,482 for additional details).

In additional embodiments, it will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired ω-3/ω-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Δ5 Desaturases

In the present invention, nucleotide sequences encoding Δ5 desaturases have been isolated from *Euglena anabaena*, as summarized below in Table 3.

TABLE 3

Summary Of *Euglena anabaena* Δ5 Desaturases

| Abbreviation | Nucleotide SEQ ID NO | Amino Acid SEQ ID NO |
|---|---|---|
| EaD5Des1 or EaD5 | 12 | 13 |
| EaD5S | 25 | 26 |

*Note: SEQ ID NO: 26 is identical in sequence to SEQ ID NO: 13.

Thus, the present invention concerns an isolated polynucleotide comprising:

(a) a nucleotide sequence encoding a polypeptide having Δ5 desaturase activity, wherein the polypeptide has at least 80% amino acid identity, based on the Clustal V method of alignment, when compared to an amino acid sequence as set forth in SEQ ID NO:13;

(b) a nucleotide sequence encoding a polypeptide having Δ5 desaturase activity, wherein the nucleotide sequence has at least 80% sequence identity, based on the BLASTN method of alignment, when compared to a nucleotide sequence as set forth in SEQ ID NO:12 or SEQ ID NO:25; or, (c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having Δ5 desaturase activity, wherein the nucleotide sequence has at least 90% sequence identity, based on the BLASTN method of alignment, when compared to a nucleotide sequence as set forth in SEQ ID NO:12 or SEQ ID NO:25.

More preferred amino acid fragments that are at least about 80%-90% identical are particularly suitable and those sequences that are at least about 90%-95% identical are most preferred. Similarly, preferred Δ5 desaturase encoding nucleic acid sequences corresponding to the instant ORFs are those encoding active proteins and which are at least about 80%-90% identical; those sequences that are at least about 90%-95% identical are most preferred.

In alternate embodiments, the instant EaD5Des1 sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In one embodiment of the invention herein, EaD5Des1 (SEQ ID NO:12) was codon-optimized for expression in *Yarrowia lipolytica*. This was possible based on previous determination of the *Y. lipolytica* codon usage profile, identification of those codons that were preferred, and determination of the consensus sequence around the 'ATG' initiation codon (see U.S. Pat. No. 7,238,482 and U.S. Pat. No. 7,125,672). The resultant synthetic gene is referred to as EaD5S (SEQ ID NO:25). The protein sequence encoded by the codon-optimized Δ5 desaturase gene (i.e., SEQ ID NO:26) is identical to that of the wildtype protein sequence (i.e., SEQ ID NO:13).

One skilled in the art would be able to use the teachings herein to create various other codon-optimized Δ5 desaturase proteins suitable for optimal expression in alternate hosts (i.e., other than *Yarrowia lipolytica*), based on the wildtype EaD5Des1 sequence. Accordingly, the instant invention relates to any codon-optimized Δ5 desaturase protein that is derived from the wildtype nucleotide sequence of EaD5Des1 (i.e., encoded by SEQ ID NO:12). This includes, but is not limited to, the nucleotide sequence set forth in SEQ ID NO:25, which encodes a synthetic Δ5 desaturase protein (i.e., EaD5S) that was codon-optimized for expression in *Yarrowia lipolytica*. In alternate embodiments, it may be desirable to modify a portion of the codons encoding EaD5Des1 to enhance expression of the gene in a host organism including, but not limited to, a plant or plant part, algae, bacteria, alternate yeast, euglenoid, stramenopiles or fungi.

Identification and Isolation of Homologs

Any of the instant desaturase sequences (i.e., EaD5Des1 or EaD5S) or portions thereof may be used to search for Δ5 desaturase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ5 desaturase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ5 desaturase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., *Proc. Acad. Sci. U.S.A.,* 82:1074 (1985); or strand displacement amplification (SDA), Walker et al., *Proc. Natl. Acad. Sci. U.S.A.,* 89:392 (1992)]; and, (3) methods of library construction and screening by complementation.

For example, genes encoding similar proteins or polypeptides to the Δ5 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing ARA and/or EPA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl Acad. Sci. U.S.A.,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Natl Acad. Sci. U.S.A.,* 86:5673 (1989); Loh et al., *Science,* 243:217 (1989)).

In other embodiments, any of the Δ5 desaturase nucleic acid fragments described herein (or any homologs identified thereof) may be used for creation of new and/or improved fatty acid desaturases. As is well known in the art, in vitro mutagenesis and selection, chemical mutagenesis, "gene shuffling" methods or other means can be employed to obtain mutations of naturally occurring desaturase genes (wherein such mutations may include deletions, insertions and point mutations, or combinations thereof). This would permit production of a polypeptide having desaturase activity, respectively, in vivo with more desirable physical and kinetic parameters for function in the host cell such as a longer half-life or a higher rate of production of a desired PUFA. Or, if desired, the regions of a polypeptide of interest (i.e., a Δ5 desaturase) important for enzymatic activity can be determined through routine mutagenesis, expression of the resulting mutant polypeptides and determination of their activities. An overview of these techniques is described in U.S. Pat. No. 7,238,482. All such mutant proteins and nucleotide sequences encoding them that are derived from EaD5 and EaD5S are within the scope of the present invention.

Alternatively, improved fatty acids may be synthesized by domain swapping, wherein a functional domain from any of the Δ5 desaturase nucleic acid fragments described herein is exchanged with a functional domain in an alternate desaturase gene to thereby result in a novel protein. As used herein, "domain" or "functional domain" refer to nucleic acid sequence(s) that are capable of eliciting a biological response in microbes.

Methods for Production of Various Omega-3 and/or Omega-6 Fatty Acids

It is expected that introduction of chimeric genes encoding the Δ5 desaturases described herein (i.e., EaD5Des1, EaD5S or other mutant enzymes, codon-optimized enzymes or homologs thereof), under the control of the appropriate promoters will result in increased production of ARA and/or EPA in the transformed host organism, respectively. As such, the present invention encompasses a method for the direct production of PUFAs comprising exposing a fatty acid substrate (i.e., DGLA and/or ETA) to the desaturase enzymes described herein (e.g., EaD5Des1 or EaD5S), such that the substrate is converted to the desired fatty acid product (i.e., ARA and/or EPA, respectively).

More specifically, it is an object of the present invention to provide a method for the production of ARA in a microbial host cell (e.g., yeast, algae, bacteria, euglenoids, stramenopiles and fungi), wherein the microbial host cell comprises:

a) a recombinant nucleotide molecule encoding a Δ5 desaturase polypeptide having at least 80% amino acid identity when compared to a polypeptide having the amino acid sequence as set forth in SEQ ID NO:13, based on the Clustal V method of alignment; and, b) a source of DGLA;

wherein the microbial host cell is grown under conditions such that the nucleic acid fragment encoding the Δ5 desaturase is expressed and the DGLA is converted to ARA, and wherein the ARA is optionally recovered.

In alternate embodiments of the present invention, the Δ5 desaturase may be used for the conversion of ETA to EPA.

Accordingly the invention provides a method for the production of EPA, wherein the microbial host cell comprises:

a) a recombinant nucleotide molecule encoding a Δ5 desaturase polypeptide having at least 80% amino acid identity when compared to a polypeptide having the amino acid sequence as set forth in SEQ ID NO:13, based on the Clustal V method of alignment; and, b) a source of ETA;

wherein the microbial host cell is grown under conditions such that the nucleic acid fragment encoding the Δ5 desaturase is expressed and the ETA is converted to EPA, and wherein the EPA is optionally recovered.

Alternatively, each Δ5 desaturase gene and its corresponding enzyme product described herein can be used indirectly for the production of various ω-6 and ω-3 PUFAs (see FIG. 1 and U.S. Pat. No. 7,238,482). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ5 desaturases described herein (i.e., EaD5Des1, EaD5S or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ8 desaturases, Δ15 desaturases, Δ9 desaturases, Δ12 desaturases, $C_{14/16}$ elongases, $C_{16/18}$ elongases, Δ9 elongases, Δ5 desaturases, Δ4 desaturases, $C_{20/22}$ elongases) to result in higher levels of production of longer-chain ω-3/ω-6 fatty acids (e.g., ARA, EPA, DTA, DPAn-6, DPA and/or DHA).

In preferred embodiments, the Δ5 desaturases of the present invention will minimally be expressed in conjunction with a Δ9 elongase and a Δ8 desaturase. The Δ5 desaturases could also be minimally expressed in conjunction with a Δ6 desaturase and a $C_{18/20}$ elongase. However, the particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ5 desaturase, based on the complete sequences described herein, the complement of those complete sequences, substantial portions of those sequences, codon-optimized desaturases derived therefrom and those sequences that are substantially homologous thereto.

Microbial Expression Systems, Cassettes and Vectors

The Δ5 desaturase genes and gene products described herein (i.e., EaD5Des1, EaD5, or other mutant enzymes, codon-optimized enzymes or homologs thereof) may be expressed in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors (e.g., constructs, plasmids) and DNA expression cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcription (e.g., a promoter), the gene coding sequence, and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Transcriptional control regions (also initiation control regions or promoters) which are useful to drive expression of the instant Δ5 desaturase ORFs in the desired microbial host cell are numerous and familiar to those skilled in the art. Virtually any promoter (i.e., native, synthetic, or chimeric) capable of directing expression of these genes in the selected host cell is suitable for the present invention, although transcriptional and translational regions from the host species are particularly useful. Expression in a microbial host cell can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest. As an example, when the host cell is yeast, transcriptional and translational regions functional in yeast cells are provided, particularly from the host species (e.g., see Patent Publication No. US-2006-0115881-A1, for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. In alternate embodiments, the 3'-region can also be synthetic, as one of skill in the art can utilize available information to design and synthesize a 3'-region sequence that functions as a transcription terminator. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the genome of the host cell; the final cellular location of the synthesized foreign protein; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell. Each of these types of modifications are encompassed in the present invention, as means to further optimize expression of the Δ5 desaturase described herein.

Transformation of Microbial Host Cells

Once a DNA cassette that is suitable for expression in an appropriate microbial host cell has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a microbial host cell by any standard technique. These techniques include transformation (e.g., lithium acetate transformation [*Methods in Enzymology,* 194:186-187 (1991)]), protoplast transformation, bolistic impact, electroporation, microinjection, or any other method that introduces the gene(s) of interest into the host cell.

For convenience, a host cell that has been manipulated by any method to take up a DNA sequence (e.g., an expression cassette) will be referred to as "transformed", "transformant" or "recombinant" herein. Thus, the term "transformed" and "recombinant" are used interchangeably herein. The transformed host will have at least one copy of the expression construct and may have two or more, depending upon whether the expression cassette is integrated into the genome or is present on an extrachromosomal element having multiple copy numbers.

The transformed host cell can be identified by various selection techniques, as described in U.S. Pat. No. 7,238,482, U.S. Pat. No. 7,259,255 and PCT Publication No. WO 2006/052870.

Following transformation, substrates suitable for the instant Δ5 desaturase (and, optionally other PUFA enzymes that are co-expressed within the host cell) may be produced by the host either naturally or transgenically, or they may be provided exogenously.

Preferred Microbial Hosts for Recombinant Expression

Microbial host cells for expression of the instant genes and nucleic acid fragments may include hosts that grow on a variety of feedstocks, including simple or complex carbohydrates, fatty acids, organic acids, oils, glycerol and alcohols, and/or hydrocarbons over a wide range of temperature and pH values. The genes described in the instant invention have been expressed in an oleaginous yeast (and in particular *Yarrowia lipolytica*). However, it is contemplated that because transcription, translation and the protein biosynthetic apparatus are highly conserved, any bacteria, yeast, algae, euglenoid, stramenopiles and/or fungus will be a suitable microbial host for expression of the present nucleic acid fragments.

Preferred microbial hosts, however, are oleaginous organisms, such as oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*). In alternate embodiments, oil biosynthesis may be genetically engineered such that the microbial host cell (e.g., a yeast) can produce more than 25% oil of the cellular dry weight, and thereby be considered oleaginous.

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.,* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for transformation of oleaginous yeasts (i.e., *Yarrowia lipolytica*) include U.S. Pat. No. 4,880,741 and U.S. Pat. No. 5,071,764 and Chen, D. C. et al. (Appl. Microbiol. Biotechnol., 48(2):232-235 (1997)). Specific teachings applicable for engineering ARA, EPA and DHA production in *Y. lipolytica* are provided in U.S. patent application Ser. No. 11/264,784, U.S. patent application Ser. No. 11/265,761, and U.S. patent application Ser. No. 11/264,737, respectively.

The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (GenBank Accession No. Z50020), the Lip2 gene locus (GenBank Accession No. AJ012632), the SCP2 gene locus (GenBank Accession No. AJ431362), and/or the Pex10 gene locus (GenBank Accession No. CAG81606)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast $Ura^-$ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997; see also PCT Publication No. WO 2006/052870 for 5-FOA use in *Yarrowia*).

An alternate preferred selection method for use in *Yarrowia* relies on a dominant, non-antibiotic marker for *Yarrowia lipolytica* based on sulfonylurea (chlorimuron ethyl; E.I. duPont de Nemours & Co., Inc., Wilmington, Del.) resistance. More specifically, the marker gene is a native acetohydroxyacid synthase (AHAS or acetolactate synthase; E.C. 4.1.3.18) that has a single amino acid change (W497L) that confers sulfonyl urea herbicide resistance (PCT Publication No. WO 2006/052870). AHAS is the first common enzyme in the pathway for the biosynthesis of branched-chain amino acids (i.e., valine, leucine, isoleucine) and it is the target of the sulfonylurea and imidazolinone herbicides.

Other preferred microbial hosts include oleaginous bacteria, algae, euglenoids, stramenopiles and other fungi; and, within this broad group of microbial hosts, of particular interest are microorganisms that synthesize ω-3/ω-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present Δ5 desaturase genes under the control of inducible or regulated promoters could yield a transformant organism capable of synthesizing increased quantities of EPA. The method of transformation of M. alpina is described by Mackenzie et al. (*Appl. Environ. Microbiol.,* 66:4655 (2000)). Similarly, methods for transformation of Thraustochytriales microorganisms (e.g., *Thraustochytrium, Schizochytrium*) are disclosed in U.S. Pat. No. 7,001,772.

Irrespective of the host selected for expression of the Δ5 desaturases described herein, multiple transformants must be screened in order to obtain a strain displaying the desired expression level and pattern. Such screening may be accomplished by Southern analysis of DNA blots (Southern, *J. Mol. Biol.,* 98:503 (1975)), Northern analysis of mRNA expression (Kroczek, *J. Chromatogr. Biomed. Appl.,* 618(1-2):133-145 (1993)), Western and/or Elisa analyses of protein expression, phenotypic analysis or GC analysis of the PUFA products.

Based on the teachings described above, in one embodiment this invention is drawn to a method of producing either ARA or EPA, respectively, comprising:

(a) providing an oleaginous yeast (e.g., *Yarrowia lipolytica*) comprising:
  (i) a first recombinant nucleotide molecule encoding a Δ5 desaturase polypeptide, operably linked to at least one regulatory sequence; and,
  (ii) a source of desaturase substrate consisting of DGLA and/or ETA, respectively; and,
(b) growing the yeast of step (a) in the presence of a suitable fermentable carbon source wherein the gene encoding the Δ5 desaturase polypeptide is expressed and DGLA is converted to ARA and/or ETA is converted to EPA, respectively; and,
(c) optionally recovering the ARA and/or EPA, respectively, of step (b).

Substrate feeding may be required.

The nucleotide sequence of the gene encoding a Δ5 desaturase may be as set forth in SEQ ID NO:12. In alternate embodiments, the nucleotide sequence of the gene encoding a Δ5 desaturase polypeptide is set forth in SEQ ID NO:25 (wherein at least 174 codons have been optimized for expression in *Yarrowia* relative to SEQ ID NO:12).

Since naturally produced PUFAs in oleaginous yeast are limited to 18:2 fatty acids (i.e., LA), and less commonly, 18:3 fatty acids (i.e., ALA), the oleaginous yeast will be genetically engineered to express multiple enzymes necessary for long-chain PUFA biosynthesis (thereby enabling production of e.g., ARA, EPA, DPA and DHA), in addition to the Δ5 desaturases described herein.

Specifically, in one embodiment this invention concerns an oleaginous yeast comprising:

(a) a first recombinant DNA construct comprising an isolated polynucleotide encoding a Δ5 desaturase polypeptide, operably linked to at least one regulatory sequence; and,
(b) at least one additional recombinant DNA construct comprising an isolated polynucleotide, operably linked to at least one regulatory sequence, encoding a polypeptide selected from the group consisting of: a Δ4 desaturase, Δ6 desaturase, a Δ9 desaturase, a Δ12 desaturase, a Δ15 desaturase, a Δ17 desaturase, a Δ8 desaturase, a Δ9 elongase, a $C_{14/16}$ elongase, a $C_{16/18}$ elongase, a $C_{18/20}$ elongase and a $C_{20/22}$ elongase.

Metabolic Engineering of Omega-3 and/or Omega-6 Fatty Acid Biosynthesis in Microbes Knowledge of the sequences of the present Δ5 desaturases will be useful for manipulating ω-3 and/or ω-6 fatty acid biosynthesis in various host cells. Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This manipulation may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art.

For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in U.S. Patent Publication No. 2006-0094092-A1, U.S. Patent Publication No. 2006-0115881-A1 and U.S. Patent Publication No. 2006-0110806-A1, respectively, as are desirable manipulations in the TAG biosynthetic pathway and the TAG degradation pathway.

Within the context of the present invention, it may be useful to modulate the expression of the fatty acid biosynthetic pathway by any one of the strategies described above. For example, the present invention provides methods whereby genes encoding key enzymes in the Δ9 elongase/Δ8 desaturase biosynthetic pathway and Δ6 desaturase/Δ6 elongase biosynthetic pathway are introduced into oleaginous yeasts for the production of ω-3 and/or ω-6 fatty acids. It will be particularly useful to express the present the Δ5 desaturase genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

Microbial Fermentation Processes for PUFA Production

The transformed microbial host cell is grown under conditions that optimize expression of chimeric desaturase and elongase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in U.S. Pat. No. 7,238,482. Although it is contemplated that the source of carbon utilized in the present invention may encompass a wide variety of carbon-containing sources, preferred carbon sources are sugars (e.g., glucose), glycerol, and/or fatty acids.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in U.S. Pat. No. 7,238,482, as are various suitable fermentation process designs (i.e., batch, fed-batch and continuous) and considerations during growth.

Purification and Processing of PUFA Oils

PUFAs may be found in the host microorganisms as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology,* 12(5/6):463-491 (1992)). A brief review of downstream processing is also available by A. Singh and O. Ward (*Adv. Appl. Microbiol.,* 45:271-312 (1997)).

In general, means for the purification of PUFAs may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. One is referred to the teachings of U.S. Pat. No. 7,238,482 for additional details.

PUFA-Containing Oils for Use in Foodstuffs, Health Food Products, Pharmaceuticals and Animal Feeds The market place currently supports a large variety of food and feed products, incorporating ω-3 and/or ω-6 fatty acids (particularly e.g., ALA, GLA, ARA, EPA, DPA and DHA). It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils of the invention containing ω-3 and/or ω-6 fatty acids will be suitable for use in a variety of food and feed products including, but not limited to: food analogs, meat products, cereal products, baked foods, snack foods and dairy products (see Patent Publication No. US-2006-0094092 for details).

Additionally, the present compositions may be used in formulations to impart health benefit in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by: 1.) Sambrook, J., Fritsch, E. F. and Maniatis, T.,

*Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and, 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2nd ed., Sinauer Associates: Sunderland, M A (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" or "hr" means hour(s), "d" means day(s), "μL" means microliter(s), "mL" means milliliter(s), "L" means liter(s), "μM" means micromolar, "mM" means millimolar, "M" means molar, "mmol" means millimole(s), "pmole" mean micromole(s), "g" means gram(s), "μg" means microgram(s), "ng" means nanogram(s), "U" means unit(s), "bp" means base pair(s) and "kB" means kilobase(s).

Nomenclature for Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica:*

*Yarrowia lipolytica* strains with ATCC Accession Nos. #20362, #76982 and #90812 were purchased from the American Type Culture Collection (Rockville, Md.). *Yarrowia lipolytica* strains were typically grown at 28-30° C. in several media, according to the recipes shown below. Agar plates were prepared as required by addition of 20 g/L agar to each liquid media, according to standard methodology.

YPD agar medium (per liter): 10 g of yeast extract [Difco], 20 g of Bacto peptone [Difco]; and 20 g of glucose.

Basic Minimal Media (MM) (per liter): 20 g glucose; 1.7 g yeast nitrogen base without amino acids; 1.0 g proline; and pH 6.1 (not adjusted).

Minimal Media+Uracil (MM+uracil or MMU) (per liter): Prepare MM media as above and add 0.1 g uracil and 0.1 g uridine.

Minimal Media+Leucine (MM+leucine or MMLeu) (per liter): Prepare MM media as above and add 0.1 g leucine.

Minimal Media+Leucine+Uracil (MMLeuUra) (per liter): Prepare MM media as above and add 0.1 g leucine, 0.1 g uracil and 0.1 g uridine.

Minimal Media+5-Fluoroorotic Acid (MM+5-FOA) (per liter): 20 g glucose, 6.7 g Yeast Nitrogen base, 75 mg uracil, 75 mg uridine and appropriate amount of FOA (Zymo Research Corp., Orange, Calif.), based on FOA activity testing against a range of concentrations from 100 mg/L to 1000 mg/L (since variation occurs within each batch received from the supplier).

High Glucose Media (HGM) (per liter): 80 glucose, 2.58 g $KH_2PO_4$ and 5.36 g $K_2HPO_4$, pH 7.5 (do not need to adjust).

Transformation of *Yarrowia lipolytica* was performed according to the method of Chen, D. C. et al. (*Appl. Microbiol. Biotechnol.,* 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer, comprising: 2.25 mL of 50% PEG, average MW 3350; 0.125 mL of 2 M lithium acetate, pH 6.0; 0.125 mL of 2 M DTT; and (optionally) 50 μg sheared salmon sperm DNA. Then, approximately 500 ng of linear DNA (preferably comprising at least one chimeric gene) (or 100 ng circular plasmid) was incubated in 100 μL of resuspended cells, and maintained at 39° C. for 1 h with vortex mixing at 15 min intervals. The cells were plated onto selection media plates and maintained at 30° C. for 2 to 3 days.

Fatty Acid Analysis of *Yarrowia lipolytica:*

For fatty acid analysis, cells were collected by centrifugation and lipids were extracted as described in Bligh, E. G. & Dyer, W. J. (*Can. J. Biochem. Physiol.,* 37:911-917 (1959)). Fatty acid methyl esters were prepared by transesterification of the lipid extract with sodium methoxide (Roughan, G. and Nishida I., *Arch Biochem Biophys.,* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Construction of *Yarrowia lipolytica* Strain Y4036U

Figure 2A:
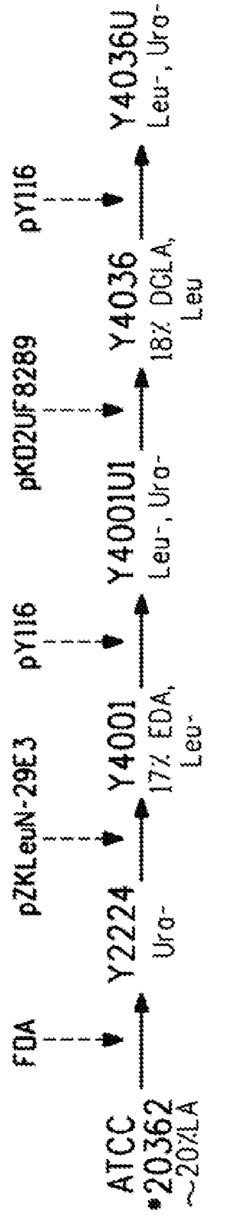

*Y. lipolytica* strain Y4036U was used as the host in Example 6, infra. The following description is a summary of the construction of strain Y4036U, derived from *Yarrowia lipolytica* ATCC #20362, capable of producing about 18% DGLA relative to the total lipids via expression of a Δ9 elongase/Δ8 desaturase pathway and having a Leu- and Ura-phenotype (FIG. 2A).

The development of strain Y4036U required the construction of strain Y2224 (a FOA resistant mutant from an autonomous mutation of the Ura3 gene of wildtype *Yarrowia* strain ATCC #20362), strain Y4001 (producing 17% EDA with a Leu-phenotype), strain Y4001U1 (producing 17% EDA with a Leu- and Ura-phenotype) and strain Y4036 (producing 18% DGLA with a Leu-phenotype).

Generation Of Strain Y2224: Strain Y2224 was isolated in the following manner: *Yarrowia lipolytica* ATCC #20362 cells from a YPD agar plate were streaked onto a MM plate (75 mg/L each of uracil and uridine, 6.7 g/L YNB with ammonia sulfate, without amino acids, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Figure 2B:
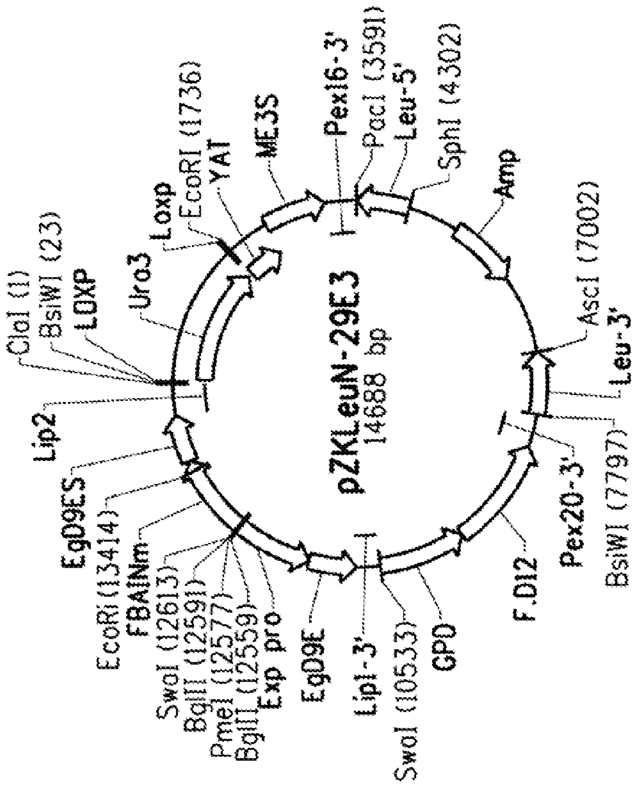

Generation Of Strain Y4001 To Produce About 17% EDA Of Total Lipids: Strain Y4001 was created via integration of construct pZKLeuN-29E3 (FIG. 2B). This construct, comprising four chimeric genes (i.e., a Δ12 desaturase, a $C_{16/18}$ elongase and two Δ9 elongases), was integrated into the Leu2 loci of strain Y2224 to thereby enable production of EDA.

Construct pZKLeuN-29E3 contained the components shown below in Table 4.

TABLE 4

Description of Plasmid pZKLeuN-29E3 (SEQ ID NO: 28)

| RE Sites And Nucleotides Within SEQ ID NO: 28 | Description Of Fragment And Chimeric Gene Components |
|---|---|
| BsiW I/Asc I (7797-7002) | 788 bp 3' portion of *Yarrowia* Leu2 gene (GenBank Accession No. AF260230) |
| Sph I/Pac I (4302-3591) | 703 bp 5' portion of *Yarrowia* Leu2 gene (GenBank Accession No. AF260230) |
| Swa I/BsiW I (10533-7797) | GPD::FmD12::Pex20, comprising:<br>GPD: *Yarrowia lipolytica* GPD promoter (U.S. Pat. No. 7,259,255);<br>FmD12: *Fusarium moniliforme* Δ12 desaturase gene (SEQ ID NO: 29) (labeled as "F.D12" in Figure; PCT Publication No. WO 2005/047485);<br>Pex20: Pex20 terminator sequence from Yarrowia Pex20 gene (GenBank Accession No. AF054613) |
| Bgl II/Swa I (12559-10533) | EXP1::EgD9eS::Lip1, comprising:<br>EXP1: *Yarrowia lipolytica* export protein (EXP1) promoter (labeled as "Exp pro" in Figure; PCT Publication No. WO 2006/052870 and U.S. Patent Application No. 11/265,761);<br>EgD9eS: codon-optimized Δ9 elongase (SEQ ID NO: 31), derived from *Euglena gracilis* (labeled as "EgD9E" in Figure; PCT Publication No. WO 2007/061742);<br>Lip1: Lip1 terminator sequence from *Yarrowia* Lip1 gene (GenBank Accession No. Z50020) |
| Pme I/Cla I (12577-1) | FBAINm::EgD9eS::Lip2, comprising:<br>FBAINm: *Yarrowia lipolytica* FBAINm promoter (U.S. Pat. No. 7,202,356);<br>EgD9eS: codon-optimized Δ9 elongase gene (SEQ ID NO: 31), derived from *Euglena gracilis* (labeled as "EgD9ES" in Figure; PCT Publication No. WO 2007/061742);<br>Lip2: Lip2 terminator sequence from Yarrowia Lip2 gene (GenBank Accession No. AJ012632) |
| Cla I/EcoR I (1-1736) | LoxP::Ura3::LoxP, comprising:<br>LoxP sequence (SEQ ID NO: 33);<br>*Yarrowia* Ura3 gene (GenBank Accession No. AJ306421);<br>LoxP sequence (SEQ ID NO: 33) |
| EcoR I/Pac I (1736-3591) | YAT1::ME3S::Pex16, comprising:<br>YAT1: *Yarrowia lipolytica* YAT1 promoter (labeled as "YAT" in Figure; Patent Publication No. U.S. 2006/0094102-A1);<br>ME3S: codon-optimized $C_{16/18}$ elongase gene (SEQ ID NO: 34), derived from *M. alpina* (PCT Publication No. WO 2007/046817);<br>Pex16: Pex16 terminator sequence of *Yarrowia* Pex 16 gene (GenBank Accession No. U75433) |

Plasmid pZKLeuN-29E3 was digested with AscI/SphI, and then used for transformation of *Y. lipolytica* strain Y2224 (i.e., ATCC #20362 Ura3-) according to the General Methods. The transformant cells were plated onto MMLeu media plates and maintained at 30° C. for 2 to 3 days. The colonies were picked and streaked onto MM and MMLeu selection plates. The colonies that could grow on MMLeu plates but not on MM plates were selected as Leu-strains. Single colonies of Leu-strains were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EDA in the transformants containing the 4 chimeric genes of pZKLeuN-29E3, but not in the *Yarrowia* Y2224 control strain. Most of the selected 36 Leu-strains produced about 12 to 16.9% EDA of total lipids. There were 3 strains (i.e., strains #11, #30 and #34) that produced about 17.4%, 17% and 17.5% EDA of total lipids; they were designated as strains Y4001, Y4002 and Y4003, respectively.

Single colonies of Y4001, Y4002 and Y4003 strains were inoculated in liquid MMLeu at 30° C. and shaken at 250 rpm/min for 2 days. The cells were collected by centrifugation, resuspended in High Glucose Media (HGM) and then shaken at 250 rpm/min for 5 days. The cells were collected by centrifugation, lipids were extracted, and fatty acid methyl esters were prepared by trans-esterification, and subsequently analyzed with a Hewlett-Packard 6890 GC. GC analyses showed that the Y4001, Y4002 and Y4003 strains produced about 24% EDA of total lipids.

Figure 3A:
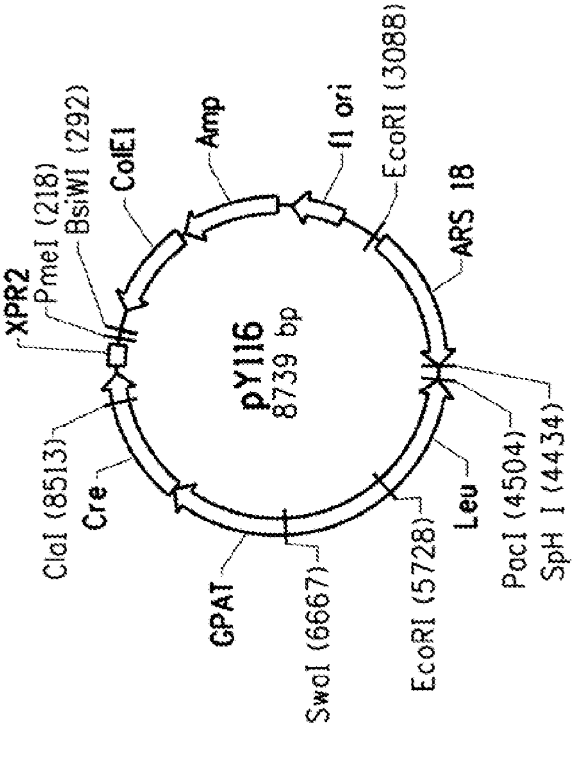

Generation Of Strain Y4001U (Leu-, Ura-): Strain Y4001U was created via temporary expression of the Cre recombinase enzyme in plasmid pY116 (FIG. 3A) within strain Y4001 to produce a Leu- and Ura-phenotype. Construct pY116 contained the following components:

TABLE 5

Description of Plasmid pY116 (SEQ ID NO: 36)

| RE Sites And Nucleotides Within SEQ ID NO: 36 | Description Of Fragment And Chimeric Gene Components |
|---|---|
| 1328-448 | ColE1 plasmid origin of replication |
| 2258-1398 | Ampicillin-resistance gene ($Amp^R$) for selection in *E. coli* |
| 3157-4461 | *Yarrowia* autonomous replication sequence (ARS18; GenBank Accession No. A17608) |
| SwaI/PacI 6667-4504 | *Yarrowia* Leu2 gene (GenBank Accession No. AF260230) |
| Swa I/Pme I (6667-218) | GPAT::Cre::XPR2, comprising:<br>GPAT: *Yarrowia lipolytica* GPAT promoter (U.S. Pat. No. 7,264,949);<br>Cre: Enterobacteria phage P1 Cre gene for recombinase protein (GenBank Accession No. X03453);<br>XPR2: ~100 bp of the 3' region of the *Yarrowia* Xpr gene (GenBank Accession No. M17741) |

Plasmid pY116 was used for transformation of freshly grown Y4001 cells according to the General Methods. The transformant cells were plated onto MMLeuUra plates containing 280 μg/mL sulfonylurea (chlorimuron ethyl, E.I. duPont de Nemours & Co., Inc., Wilmington, Del.) and maintained at 30° C. for 3 to 4 days. Four colonies were picked, inoculated into 3 mL liquid YPD media at 30° C. and shaken at 250 rpm/min for 1 day. The cultures were diluted to 1:50,000 with liquid MMLeuUra media, and 100 μL was plated onto new YPD plates and maintained at 30° C. for 2 days. Colonies were picked and streaked onto MMLeu and MMLeuUra selection plates. The colonies that could grow on MMLeuUra plates but not on MMLeu plates were selected and analyzed by GC to confirm the presence of C20:2 (EDA). Several strains, each having a Leu- and Ura-phenotype, produced about 17% EDA of total lipids and collectively, were designated as Y4001U. One of these strains was designated as Y4001U1.

Figure 3B:
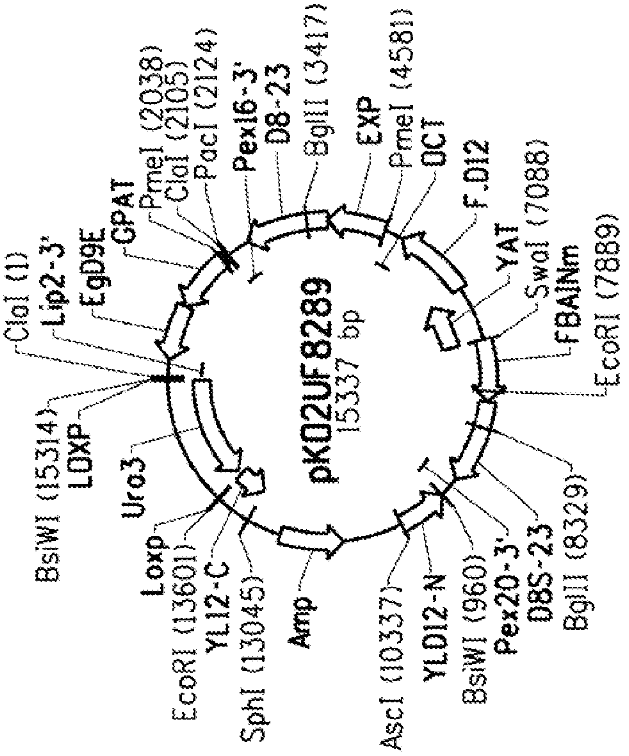

Generation Of Y4036 Strain To Produce About 18% DGLA Of Total Lipids: Construct pKO2UF8289 (FIG. 3B; SEQ ID NO:37) was generated to integrate four chimeric genes (comprising a Δ12 desaturase, one Δ9 elongase and two mutant Δ8 desaturases) into the Δ12 loci of strain Y4001U1, to thereby enable production of DGLA. Construct pKO2UF8289 contained the following components:

TABLE 6

Description of Plasmid pKO2UF8289 (SEQ ID NO: 37)

| RE Sites And Nucleotides Within SEQ ID NO: 37 | Description Of Fragment And Chimeric Gene Components |
|---|---|
| AscI/BsiWI (10337-9600) | 5' portion of *Yarrowia* Δ12 desaturase gene (SEQ ID NO: 38) (labeled as "YLD12-N" in Figure; U.S. Pat. No. 7,214,491) |
| EcoRI/SphI (13601-13045) | 3' portion of *Yarrowia* Δ12 desaturase gene (SEQ ID NO: 38) (labeled as "YL12-C" in Figure; U.S. Pat. No. 7,214,491) |
| SwaI/BsiWI (7088-9600) | FBAINm::EgD8M::Pex20, comprising:<br>FBAINm: *Yarrowia lipolytica* FBAINm promoter (U.S. Pat. No. 7,202,356);<br>EgD8M: Synthetic mutant Δ8 desaturase (SEQ ID NO: 40) (labeled as "D8D-23" in Figure; U.S. Patent Application No. 11/635,258), derived from *Euglena gracilis* ("EgD8S"; U.S. Pat. No. 7,256,033);<br>Pex20: Pex20 terminator sequence from *Yarrowia* Pex20 gene (GenBank Accession No. AF054613) |
| SwaI/PmeI (7088-4581) | YAT1::FmD12::OCT, comprising:<br>YAT1: *Yarrowia lipolytica* YAT1 promoter (labeled as "YAT" in Figure; Patent Publication No. U.S. 2006/0094102-A1);<br>FmD12: *Fusarium moniliforme* Δ12 desaturase gene (SEQ ID NO: 29) (labeled as "F.D12" in Figure; PCT Publication No. WO 2005/047485);<br>OCT: OCT terminator sequence of *Yarrowia* OCT gene (GenBank Accession No. X69988) |
| PmeI/PacI (4581-2124) | EXP1::EgD8M::Pex16, comprising:<br>EXP1: *Yarrowia lipolytica* export protein (EXP1) promoter (PCT Publication No. WO 2006/052870 and U.S. Patent Application No. 11/265,761);<br>EgD8M: Synthetic mutant Δ8 desaturase (SEQ ID NO: 40) (labeled as "D8-23" in Figure; U.S. Patent Application No. 11/635,258), derived from *Euglena gracilis* ("EgD8S"; U.S. Pat. No. 7,256,033);<br>Pex16: Pex16 terminator sequence from *Yarrowia* Pex16 gene (GenBank Accession No. U75433) |
| PmeI/ClaI (2038-1) | GPAT::EgD9e::Lip2, comprising:<br>GPAT: *Yarrowia lipolytica* GPAT promoter (U.S. Pat. No. 7,264,949);<br>EgD9e: *Euglena gracilis* Δ9 elongase gene (SEQ ID NO: 42) (labeled as "EgD9E" in Figure; PCT Publication No. WO 2007/061742);<br>Lip2: Lip2 terminator sequence from *Yarrowia* Lip2 gene (GenBank Accession No. AJ012632) |
| ClaI/EcoRI (13601-1) | LoxP::Ura3::LoxP, comprising:<br>LoxP sequence (SEQ ID NO: 33);<br>*Yarrowia* Ura3 gene (GenBank Accession No. AJ306421);<br>LoxP sequence (SEQ ID NO: 33) |

The pKO2UF8289 plasmid was digested with AscI/SphI, and then used for transformation of strain Y4001U1 according to the General Methods. The transformant cells were plated onto MMLeu plates and maintained at 30° C. for 2 to 3 days. The colonies were picked and streaked onto MMLeu selection plates at 30° C. for 2 days. These cells were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKO2UF8289, but not in the parent Y4001U1 strain. Most of the selected 96 strains produced between 7% and 13% DGLA of total lipids. There were 6 strains (i.e., #32, #42, #60, #68, #72 and #94) that produced about 15%, 13.8%, 18.2%, 13.1%, 15.6% and 13.9% DGLA of total lipids. These six strains were designated as Y4034, Y4035, Y4036, Y4037, Y4038 and Y4039, respectively.

Generation Of Strain Y4036U (Leu-, Ura3-): Construct pY116 (FIG. 3A; SEQ ID NO:36) was utilized to temporarily express a Cre recombinase enzyme in strain Y4036. This released the LoxP sandwiched Ura3 gene from the genome.

Plasmid pY116 was used to transform strain Y4036 according to the General Methods. Following transformation, the cells were plated onto MMLeuUra plates and maintained at 30° C. for 2 to 3 days. The individual colonies grown on MMLeuUra plates were picked, and streaked into YPD liquid media at 30° C. and shaken at 250 rpm/min for 1 day to cure the pY116 plasmid. The grown cultures were streaked on MMLeuUra plates. After two days at 30° C., the individual colonies were re-streaked on MMLeuUra, MMU and MMLeu plates. Those colonies that could grow on MMLeuUra, but not on MMU or MMLeu plates were selected. One of these strains with Leu- and Ura-phenotypes was designated as Y4036U.

Example 1

Synthesis of a cDNA Library from *Euglena anabaena* UTEX 373

The present Example describes the synthesis of a cDNA library from *Euglena anabaena* UTEX 373. This work included the preparation of RNA, synthesis of cDNA, and generation of a cDNA library.

Growth of *Euglena anabaena* UTEX 373 and Preparation of RNA

Figure 4:
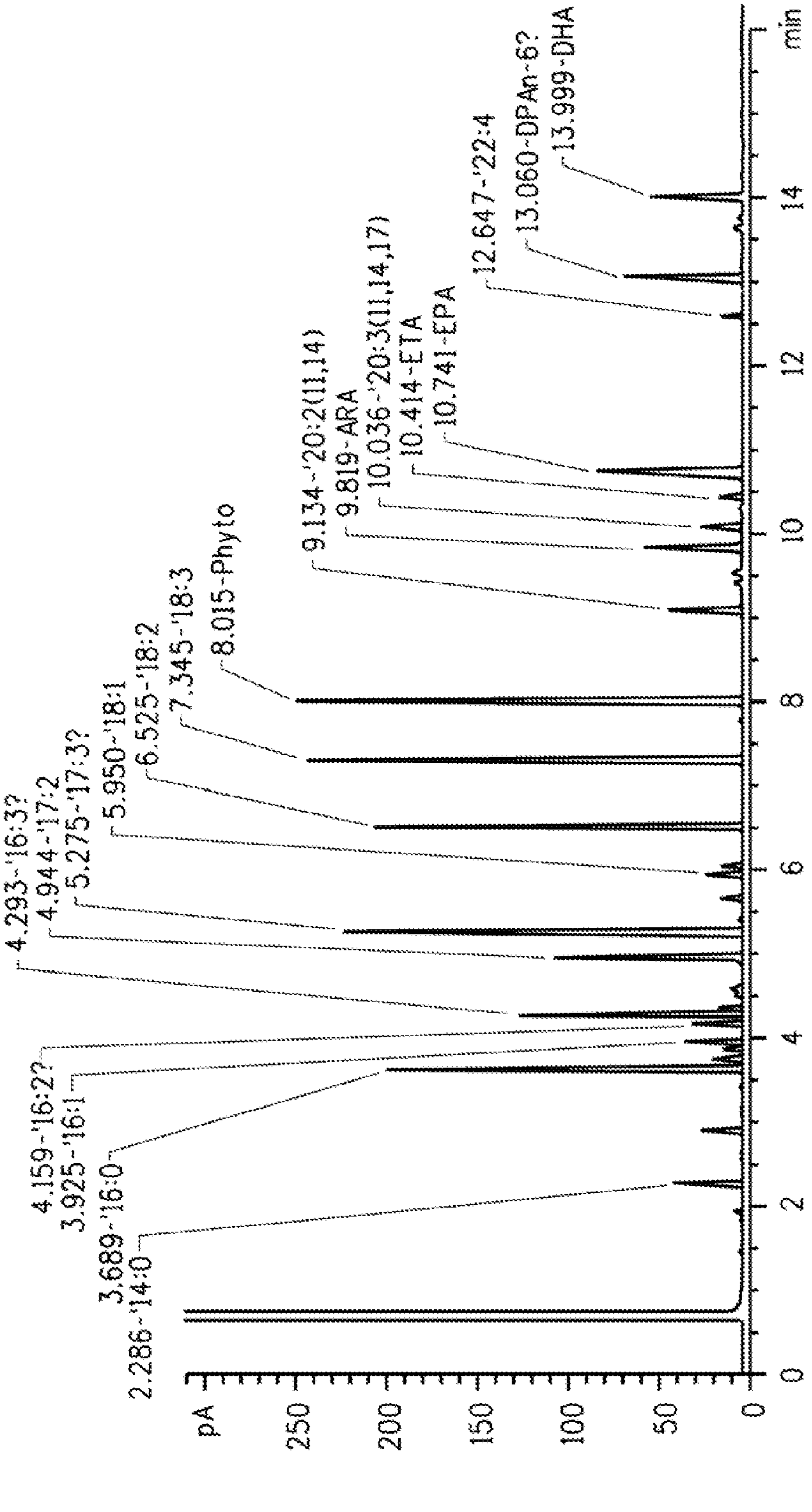
FIG. 4 shows a chromatogram of the lipid profile of an *Euglena anabaena* cell extract as described in Example 1.

*Euglena anabaena* UTEX 373 was obtained from Dr. Richard Triemer's lab at Michigan State University (East Lansing, Mich.). Approximately 2 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this step, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Catalog No. 24152). The oven temperature was programmed to hold at 170° C. for 1.0 min, increase to 240° C. at 5° C./min and then hold for an additional 1.0 min. Carrier gas was supplied by a Whatman hydrogen generator. Retention times were compared to those for methyl esters of standards commercially available (Nu-Chek Prep, Inc. Catalog No. U-99-A) and the resulting chromatogram is shown in FIG. 4. The presence of EDA, ERA, EPA and DHA in the fatty acid profile, with the absence of GLA and STA, suggested that *Euglena anabaena* uses the Δ9 elongase/Δ8 desaturase pathway for long-chain (LC) PUFA biosynthesis and would be a good source for LC-PUFA biosynthetic genes such as, but not limited to, Δ5 desaturases.

The remaining 5 mL of an actively growing culture was transferred into 25 mL of AF-6 Medium (Watanabe & Hiroki, NIES-Collection List of Strains, 5th ed., National Institute for Environmental Studies, Tsukuba, 127 pp (2004)) in a 125 mL glass flask. *Euglena anabaena* cultures were grown at 22° C. with a 16 h light, 8 h dark cycle for 2 weeks with very gentle agitation.

After 2 weeks, the culture (25 mL) was transferred to 100 mL of AF-6 medium in a 500 mL glass bottle and the culture was grown for 1 month as described above. After this time, two 50 mL aliquots were transferred into two separate 500 mL glass bottles containing 250 mL of AF-6 medium and the cultures were grown for two months as described above (giving a total of ~600 mL of culture). Next, the cultures were pelleted by centrifugation at 1,800×g for 10 min, washed once with water and re-centrifuged. Total RNA was extracted from one of the resulting pellets using the RNA STAT-60™ reagent (TEL-TEST, Inc., Friendswood, Tex.) and following the manufacturer's protocol provided (use 5 mL of reagent, dissolved RNA in 0.5 mL of water). In this way, 340 μg of total RNA (680 μg/mL) was obtained from the pellet. The remaining pellet was frozen in liquid nitrogen and stored at −80° C. The mRNA was isolated from all 340 μg of total RNA using the mRNA Purification Kit (Amersham Biosciences, Piscataway, N.J.) following the manufacturer's protocol provided. In this way, 9.0 μg of mRNA was obtained.

Preparation of *Euglena anabaena* cDNA and Generation of cDNA Library eug1c

A cDNA library was generated using the Cloneminer™ cDNA Library Construction Kit (Catalog No. 18249-029, Invitrogen Corporation, Carlsbad, Calif.) and following the manufacturer's protocol provided (Version B, 25-0608). Using the non-radiolabeling method, cDNA was synthesized from 5.12 μg of mRNA (described above) using the Biotin-attB2-Oligo(dT) primer. After synthesis of the first and second strand, the attB1 adapter was added, ligated and the cDNA was size fractionated using column chromatography. DNA from fractions were concentrated, recombined into PDONR™222 and transformed into *E. coli* ElectroMAX™ DH10B™ T1 Phage-Resistant cells (Invitrogen Corporation). The *Euglena anabaena* library was named eug1c.

The cDNA library eug1c was plated onto LB+Kanamycin plates (approx. 100,000 colonies), the colonies were scraped off and DNA was isolated using the QIAprep® Spin Miniprep Kit (Qiagen Inc., Valencia, Calif.) following the manufacturer's protocol. In this way, a plasmid DNA sub-library from eug1c was obtained.

Example 2

Isolation of a Full-Length Δ5 Desaturase from *Euglena anabaena* UTEX 373

The present Example describes the identification of a cDNA (SEQ ID NO:3) encoding Δ5 desaturase from *Euglena anabaena* UTEX 373. This work included the generation of a probe derived from the *Euglena gracilis* Δ5 desaturase (EgD5; SEQ ID NO:1; which is described in U.S. patent application Ser. No. 11/748,629 (U.S. Publication No. 2007-0292924-A1 and PCT Publication No. WO 2007/136671)) and the hybridization of the probe to the cDNA library eug1c in order to identify Δ5 desaturase homologs from *Euglena anabaena* UTEX 373.

Generation of Construct pDMW367, Comprising EgD5

Figure 5A:
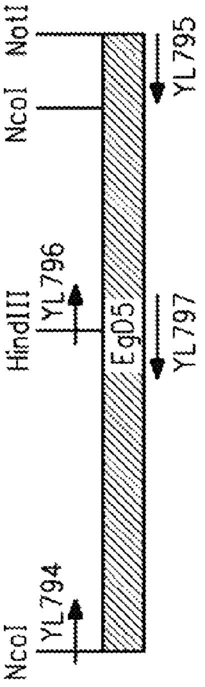
FIG. 5A illustrates the cloning strategy utilized for amplification of the *Euglena gracilis* Δ5 desaturase gene (EgD5).
Figure 5B:
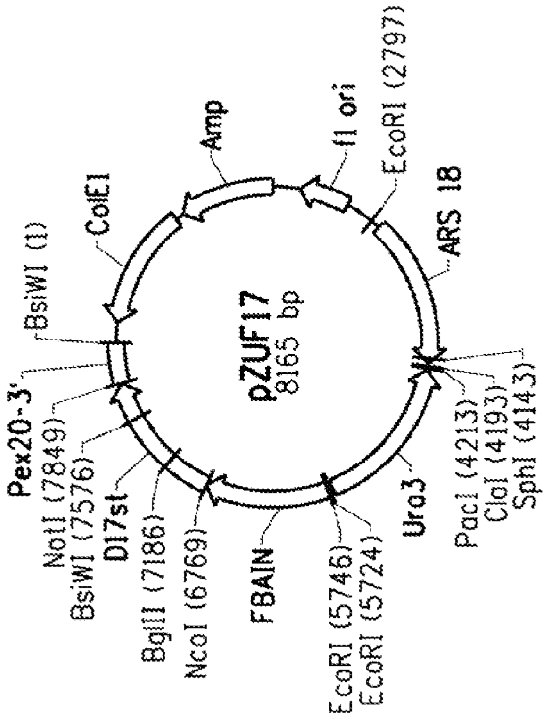
Figure 5C:
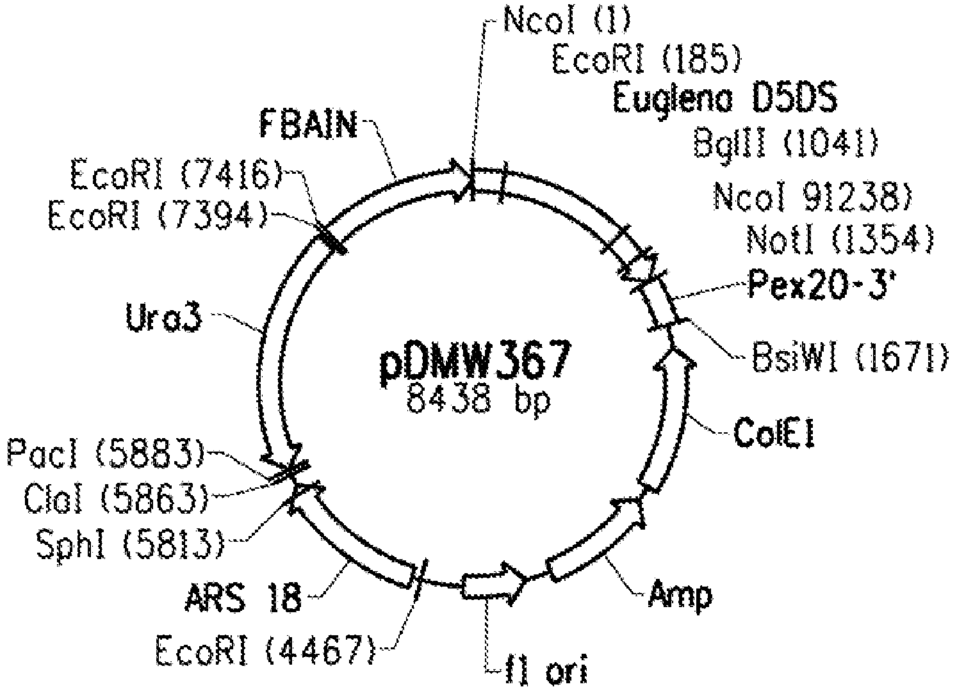
FIG. 5C is a plasmid map of pDMW367.

Based on the cDNA sequence of the *Euglena gracilis* Δ5 desaturase (EgD5; SEQ ID NO:1) oligonucleotides YL794 and YL797 (SEQ ID NOs:4 and 5, respectively) were used as primers to amplify the first portion of EgD5 (FIG. 5A). Primer YL794 contained a NcoI site and primer YL797 contained a HindIII site. Then, primers YL796 and YL795 (SEQ ID NOs:6 and 7, respectively) were used as primers to amplify the second portion of EgD5. Primer YL796 contained a HindIII site, while primer YL797 contained a NotI site. The PCR reactions, using primer pairs YL794/YL797 or YL796/YL795, with *Euglena gracilis* cDNA (the generation of which is described in U.S. Publication No. 2007-0292924-A1) as template, were individually carried out in a 50 μL total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 7° C. for 10 min. The individual PCR products were purified using a Qiagen PCR purification kit. The PCR product from the reaction amplified with primers YL794/797 was digested with NcoI and HindIII, while the PCR product from the reaction amplified with primers YL796/YL795 was digested with HindIII and NotI. The NcoI/HindIII and the HindIII/NotI digested DNA fragments were purified following gel electrophoresis in 1% (w/v) agarose, and then directionally ligated with NcoI/NotI digested pZUF17 (FIG. 5B; SEQ ID NO:8; comprising a synthetic Δ17 desaturase gene ["D17st"] derived from *S. diclina* (U.S. Publication No. 2003/0196217 A1), codon-optimized for *Yarrowia lipolytica* (U.S. Pat. No. 7,125,672)). The product of this ligation was pDMW367 (FIG. 5C; SEQ ID NO:9), which thereby contained the following components:

TABLE 7

Components Of Plasmid pDMW367 (SEQ ID NO: 9)

| RE Sites and Nucleotides Within SEQ ID NO: 9 | Description Of Fragment And Chimeric Gene Components |
|---|---|
| EcoR I/BsiW I (7416-1617) | FBAIN::EgD5::Pex20, comprising:<br>FBAIN: *Yarrowia lipolytica* FBAIN promoter (U.S. Pat. No. 7,202,356);<br>EgD5: *Euglena gracilis* Δ5 desaturase (SEQ ID NO: 1; PCT Publication No. WO 2007/136671);<br>Pex20: Pex20 terminator sequence of *Yarrowia* Pex20 gene (GenBank Accession No. AF054613) |
| 2707-1827 | ColE1 plasmid origin of replication |
| 3637-2777 | ampicillin-resistance gene ($Amp^R$) for selection in *E. coli* |
| 4536-5840 | *Yarrowia* autonomous replication sequence (ARS18; GenBank Accession No. A17608) |
| 7373-5886 | *Yarrowia* Ura 3 gene (GenBank Accession No. AJ306421) |

The term "FBAIN promoter" or "FBAIN promoter region" refers to the 5' upstream untranslated region in front of the 'ATG' translation initiation codon of the *Yarrowia lipolytica* fructose-bisphosphate aldolase enzyme (E.C. 4.1.2.13) encoded by the fba1 gene and that is necessary for expression, plus a portion of 5' coding region that has an intron of the fba1 gene.

Colony Lifts

Approximately 17,000 clones of *Euglena anabaena* cDNA library eug1c were plated onto three large square (24 cm×24 cm) petri plates (Corning, Corning, N.Y.) each containing LB+50 μg/mL kanamycin agar media. Cells were grown overnight at 37° C. and plates were then cooled to room temperature.

Biodyne B 0.45 μm membrane (Catalog No. 60207, Pall Corporation, Pensacola, Fla.) was trimmed to approximately 22 cm×22 cm and the membrane was carefully layed on top of the agar to avoid air bubbles. After incubation for 2 min at room temperature, the membrane was marked for orientation, lifted off with tweezers and placed colony-side up on filter paper soaked with 0.5 M sodium hydroxide and 1.5 M sodium chloride. After denaturation for 4 min, the sodium hydroxide was neutralized by placing the membrane on filter paper soaked with 0.5 M Tris-HCL (pH 7.5) and 1.5 M sodium chloride for 4 min. This step was repeated and the membrane was rinsed briefly in 2×SSC buffer (20×SSC is 3 M sodium chloride, 0.3 M sodium citrate; pH 7.0) and air dried on filter paper.

Hybridization

Membranes were pre-hybridized at 65° C. in 200 mL hybridization solution for 2 hr. Hybridization solution contained 6×SSPE (20×SSPE is 3 M sodium chloride, 0.2 M sodium phosphate, 20 mM EDTA; pH 7.4), 5×Denhardt's reagent (100×Denhardt's reagent is 2% (w/v) Ficoll, 2% (w/v) polyvinylpyrrolidone, 2% (w/v) acetylated bovine serum albumin), 0.5% sodium dodecyl sulfate (SDS), 100 μg/mL sheared salmon sperm DNA and 5% dextran sulfate.

A DNA probe was made using an agarose gel purified NcoI/NotI DNA fragment, containing the *Euglena gracilis* Δ5 desaturase gene, from pDMW367 (SEQ ID NO:9) labeled with $P^{32}$ dCTP using the RadPrime DNA Labeling System (Catalog No. 18428-011, Invitrogen, Carlsbad, Calif.) following the manufacturer's instructions. Unincorporated $P^{32}$ dCTP was separated using a NICK column (Catalog No. 17-0855-02, Amersham Biosciences, Piscataway, N.J.) following the manufacturer's instructions. The probe was denatured for 5 min at 100° C., placed on ice for 3 min and half was added to the hybridization solution.

The membrane was hybridized with the probe overnight at 65° C. with gentle shaking and then washed the following day twice with 2×SSC containing 0.5% SDS (5 min each) and twice with 0.2×SSC containing 0.1% SDS (15 min each). After washing, hyperfilm (Catalog No. RPN30K, Amersham Biosciences, Piscataway, N.J.) was exposed to the membrane overnight at −80° C.

Based on alignment of plates with the exposed hyperfilm, positive colonies were picked using the blunt end of a Pasteur pipette into 1 mL of water and vortexed. Several dilutions were made and plated onto small round Petri dishes (82 mm) containing LB media plus 50 μg/mL kanamycin to obtain around 100 well isolated colonies on a single plate. Lifts were done as described above except NytranN membrane circles (Catalog No. 10416116, Schleicher & Schuell, Keene, N.H.) were used and hybridization was carried out in 100 mL using the remaining radiolabeled probe. In this way, positive clones were confirmed.

Individual positive clones were grown at 37° C. in LB+50 μg/mL kanamycin liquid media and plasmid was purified using the QIAprep® Spin Miniprep Kit (Qiagen Inc.) following the manufacturer's protocol.

DNA inserts were end-sequenced in 384-well plates, using vector-primed M13F universal primer (SEQ ID NO:10), M13rev-28 primer (SEQ ID NO:11) and the poly(A) tail-primed WobbleT oligonucleotides, with the ABI BigDye version 3 Prism sequencing kit. For the sequencing reaction, 100-200 ng of template and 6.4 μmol of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers. The WobbleT primer is an equimolar mix of 21 mer poly(T)A, poly(T)C, and poly(T)G, used to sequence the 3' end of cDNA clones.

Sequences were aligned and compared using Sequencher™ (Version 4.2, Gene Codes Corporation, Ann Arbor, Mich.) and in this way, it was determined that all of the CDS in each cDNA were identical. A representative clone containing a cDNA (i.e., plasmid pLF119) is shown in SEQ ID NO:14 and the gene contained within the cDNA was designated EaD5Des1. The coding sequence for EaD5Des1 is shown in SEQ ID NO:12; while the corresponding amino acid sequence for EaD5Des1 is shown in SEQ ID NO:13.

Example 3

Primary Sequence Analysis of the Δ5 Desaturase Sequence of *Euglena anabaena* UTEX 373 (EaD5Des1) and Comparison to the Δ5 Desaturase Sequence of *Euglena gracilis* (EgD5)

The amino acid sequence for EaD5Des1 (SEQ ID NO:13) was evaluated by BLASTP (Basic Local Alignment Search Tool; Altschul et al., *J. Mol. Biol.,* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases) using default parameters with the filter turned off. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

BLASTP analysis with EaD5Des1 yielded a pLog value of 76.52 (P value of 3e-77) versus the *Thalassiosira pseudonana* Δ8 fatty acid desaturase (TpsD8; SEQ ID NO:15) (NCBI Accession No. AAX14502 (GI 60172920), locus AAX14502, CDS AY817152; Tonon et al., *FEBS J.,* 272: 3401-3412 (2005)) when compared to the "nr" database. Although identified as a Δ8 fatty acid desaturase in the NCBI database, AY817152 was identified as a Δ5 desaturase in Tonon et al. and the NCBI designation as a Δ8 fatty acid desaturase is likely an error. BLASTP analysis with EaD5Des1 also yielded a pLog value of 75.70 (P value of 2e-76) versus the *Phaeodactylum tricornutum* Δ5 fatty acid desaturase (SEQ ID NO:16) (NCBI Accession No. AAL92562 (GI 19879687), locus AAL92562, CDS AY082392; Domergue et al., *Eur. J. Biochem.,* 269:4105-4113 (2002)) when compared to the "nr" database.

The amino acid sequence for EaD5Des1 (SEQ ID NO:13) was compared to the *Thalassiosira pseudonana* Δ8 fatty acid desaturase (SEQ ID NO:15) and the *Euglena gracilis* Δ5 desaturase amino acid sequence (EgD5; SEQ ID NO:2; which is described in U.S. Publication No. 2007-0292924-A1) using BlastP, Clustal V and the Jotun Hein methods of sequence comparison. The % identity against TpsD8 and EgD5 using each method is shown in Table 8 and Table 9, respectively.

Sequence percent identity calculations performed by the BlastP method are as described above. Sequence percent identity calculations were performed by the Clustal V method (Higgins, D. G. and Sharp, P. M., *Comput. Appl. Biosci.,* 5:151-153 (1989); Higgins et al., *Comput. Appl. Biosci.,* 8:189-191 (1992)) using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10).

Sequence percent identity calculations performed by the Jotun Hein method (Hein, J. J., *Meth. Enz.,* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2).

TABLE 8

Sequence Comparison of EaD5Des1 (SEQ ID NO: 13) to TpsD8 (SEQ ID NO: 15)

| Desaturase | % Identity to TpsD8 by BLASTP | % Identity to TpsD8 by the Jotun Hein Method | % Identity to TpsD8 by the Clustal V Method |
|---|---|---|---|
| EaD5Des1 | 37% | 40.8% | 30.8% |

TABLE 9

Sequence Comparison of EaD5Des1 (SEQ ID NO: 13) to EgD5 (SEQ ID NO: 2)

| Desaturase | % Identity to EgD5 by BLASTP | % Identity to EgD5 by the Jotun Hein Method | % Identity to EgD5 by the Clustal V Method |
|---|---|---|---|
| EaD5Des1 | 73% | 72.4% | 77.1% |

Example 4

Functional Analysis of the *Euglena anabaena* UTEX 373 Δ5 Desaturase (EaD5Des1) in *Yarrowia lipolytica*

The present Example describes functional analysis of EaD5Des1 (SEQ ID NO:13) in *Yarrowia lipolytica*. This work included the following steps: (1) construction of Gateway®-compatible *Yarrowia* expression vector pY159; (2) transfer of EaD5Des1 into pY159 to produce pY169; and, (3) comparison of lipid profiles within transformant organisms comprising pY169.

Construction of Gateway®-Compatible *Yarrowia* Expression Vector pY159

Plasmid pY5-30 (which was previously described in U.S. Pat. No. 7,259,255), is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (AmpR), for selection in *E. coli*; a *Yarrowia* LEU2 gene, for selection in *Yarrowia*; and a chimeric TEF::GUS::XPR gene. Plasmid pDMW263 (SEQ ID NO:17) was created from pY5-30, by replacing the TEF promoter with the *Yarrowia lipolytica* FBAINm promoter (U.S. Pat. No. 7,202,356) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 10 summarizes the components of pDMW263 (SEQ ID NO:17).

TABLE 10

Components Of Plasmid pDMW263 (SEQ ID NO: 17)

| RE Sites and Nucleotides Within SEQ ID NO: 17 | Description of Fragment and Chimeric Gene Components |
|---|---|
| 4992-4296 | ARS18 sequence (GenBank Accession No. A17608) |
| SalI/SacII (8505-2014) | FBAINm::GUS::XPR, comprising:<br>FBAINm: *Yarrowia lipolytica* FBAINm promoter (U.S. Pat. No. 7,202,356);<br>GUS: *E. coli* gene encoding β-glucuronidase (Jefferson, R. A. Nature, 14: 342: 837-838 (1989);<br>XPR: ~100 bp of the 3' region of the *Yarrowia* Xpr gene (GenBank Accession No. M17741) |
| 6303-8505 | *Yarrowia* Leu2 gene (GenBank Accession No. AF260230) |

Figure 6B:
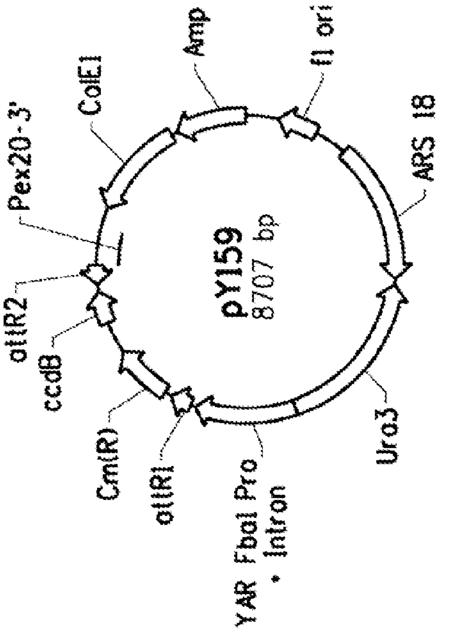
Figure 6A:
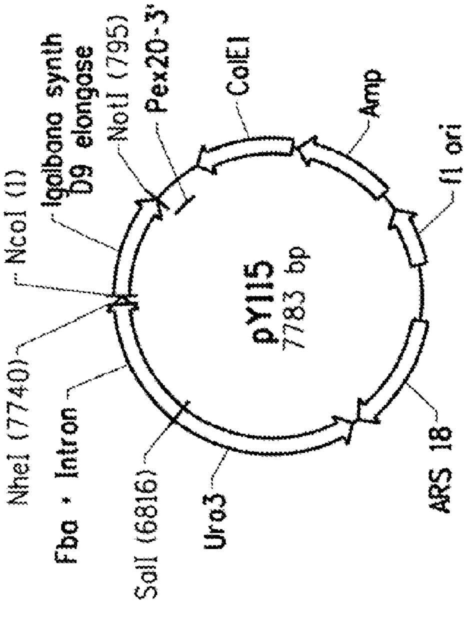

The NcoI/SalI DNA fragment from pDMW263 (SEQ ID NO:17), containing the *Yarrowia lipolytica* FBAINm promoter, was cloned into the NcoI/SalI DNA fragment of pDMW237 (SEQ ID NO:18), previously described in PCT Publication No. WO 2006/012325 (the contents of which are hereby incorporated by reference), containing a synthetic Δ9 elongase gene derived from *Isochrysis galbana* and codon-optimized for expression in *Yarrowia lipolytica* (IgD9eS), to produce pY115 (SEQ ID NO:19; FIG. 6A). In FIG. 6A, the modified FBAINm promoter is labeled as FBA1+Intron, while it is labeled as YAR FBA1 PRO+Intron in FIGS. 6B and 6C.

The FBAINm promoter was amplified from plasmid pY115 (SEQ ID NO:19), using PCR with oligonucleotide primers oYFBA1 (SEQ ID NO:20) and oYFBA1-6 (SEQ ID NO:21). Primer oYFBA1 (SEQ ID NO:20) was designed to introduce a BglII site at the 5' end of the promoter and primer oYFBA1-6 (SEQ ID NO:21) was designed to introduce a NotI site at the 3' end of the promoter while removing the NcoI site and thus, the ATG start codon. The resulting PCR fragment was digested with BglII and NotI and cloned into the BglII/NotI fragment of pY115, containing the vector backbone, to form pY158 (SEQ ID NO:22).

Plasmid pY158 (SEQ ID NO:22) was digested with NotI and the resulting DNA ends were filled. After filling to form blunt ends, the DNA fragments were treated with calf intestinal alkaline phosphatase and separated using agarose gel electrophoresis. The 6992 bp fragment containing the *Yarrowia lipolytica* FBAINm promoter was excised from the agarose gel and purified using the QIAquick® Gel Extraction Kit (Qiagen Inc., Valencia, Calif.) following the manufacturer's protocol. The purified 6992 bp fragment was ligated with cassette rfA using the Gateway Vector Conversion System (Catalog No. 11823-029, Invitrogen Corporation) following the manufacturer's protocol to form *Yarrowia lipolytica* Gateway® destination vector pY159 (SEQ ID NO:23; FIG. 6B).

Construction of *Yarrowia* Expression Vector pY169

Figure 6C:
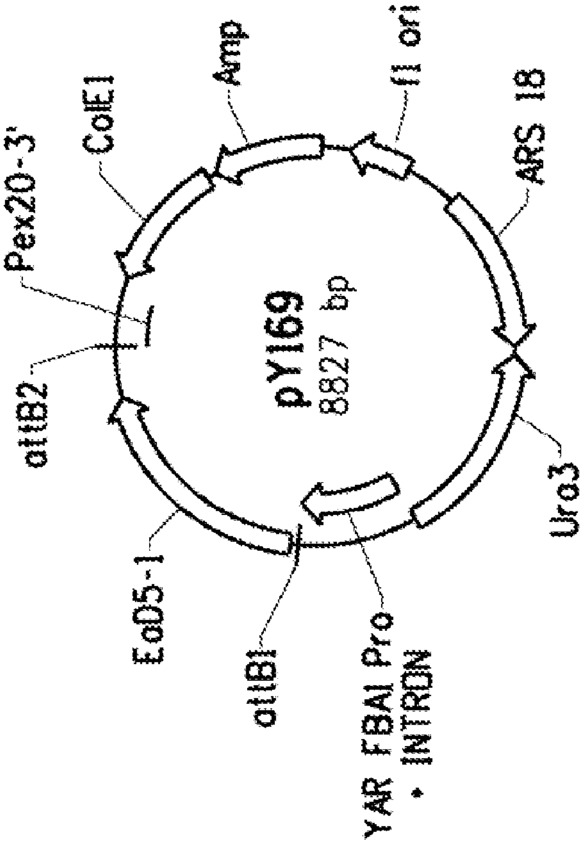

Using the Gateway® LR Clonase™ II enzyme mix (Catalog No. 11791-020, Invitrogen Corporation) and following the manufacturer's protocol, the cDNA insert from pLF119 (SEQ ID NO:14; Example 2) was transferred to pY159 (SEQ ID NO:23) to form pY169 (SEQ ID NO:24, FIG. 6C). In FIG. 6C, EaD5Des1 is identified as EaD5-1 but they are identical.

Functional Analysis of EaD5Des1 in *Yarrowia lipolytica* Strain Y2224

Strain Y2224 was transformed with pY169 (SEQ ID NO:24, FIG. 6C) as described in the General Methods.

Single colonies of transformant *Yarrowia lipolytica* containing pY169 were grown in 3 mL minimal media lacking uracil supplemented with 0.2% tergitol at 30° C. for 1 day. After this, 0.1 mL was transferred to 3 mL of the same medium supplemented with either ALA, EDA, ERA, DGLA, ETA, EPA, DPA or no fatty acid. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.,* 276 (1):38-46 (1990)) with 500 μL of 1% sodium methoxide for 30 min at 50° C. after which 500 μL of 1 M sodium chloride and 100 μL of heptane were added. After thorough mixing and centrifugation, fatty acid methyl esters (FAMEs) were analyzed by GC. FAMEs (5 μL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. In the case of DPA feeding, GC analysis was carried out in a similar way except that the oven temperature was programmed to hold at 170° C. for 1.0 min, increase to 240° C. at 5° C./min and then hold for an additional 1.0 min. Retention times were compared to those for methyl esters of standards commercially available (Nu-Chek Prep, Inc.).

The fatty acid profiles for *Yarrowia lipolytica* expressing pY169 and fed various substrates are shown in FIG. 7. Substrates (i.e., either LA—when no fatty acid fed, ALA, EDA, ERA, DGLA, ETA or DPA) were fed to assess Δ4 (i.e., DPA to DHA conversion), Δ5 (i.e., DGLA to ARA, DTA to EPA, EDA to SCI and/or ERA to JUP conversion), Δ6 (i.e., LA to GLA and/or ALA to STA conversion), Δ8 (i.e., EDA to DGLA and/or ERA to ETA conversion) or ω-3 (i.e., LA to ALA, EDA to ERA and/or DGLA to ETA conversion) desaturase activities. In FIG. 7 shading indicates the substrates fed and products produced.

Percent desaturation (% desat) was calculated by dividing the weight % (wt %) for substrate (either LA—when no fatty acid fed, ALA, EDA, ERA, DGLA, ETA or DPA) by the sum of the wt % for the substrate (either LA—when no fatty acid fed, ALA, EDA, ERA, DGLA, ETA or DPA) and product (either GLA, STA, DGLA, ETA, ARA, EPA or DHA, respectively) and multiplying by 100 to express as a %, depending on which substrate was fed. From the results in FIG. 7, it is clear that EaD5Des1 functions as a Δ5 desaturase with preference for DGLA and ETA over EDA and ERA.

The ratio of desaturation of ω-6 substrate to ω-3 substrate (Ratio n-6/n-3) is calculated by dividing the average percent desaturation (Ave. % desat) for either DGLA by ETA or EDA by ERA. In both cases, EaD5Des1 prefers n-6 substrates over n-3 substrates. The ratio of desaturation of the preferred substrate to that of the non-preferred substrate (Ratio Prod/By-Prod) is calculated by dividing the Ave. % desat for either DGLA by EDA or ETA by ERA. In both cases, EaD5Des1 has an approximately 3.5-fold preference for DGLA or ETA over EDA or ERA, respectively.

Example 5

Synthesis of a Codon-Optimized Δ5 Desaturase Gene for *Yarrowia lipolytica* (EaD5S)

Figure 9B:
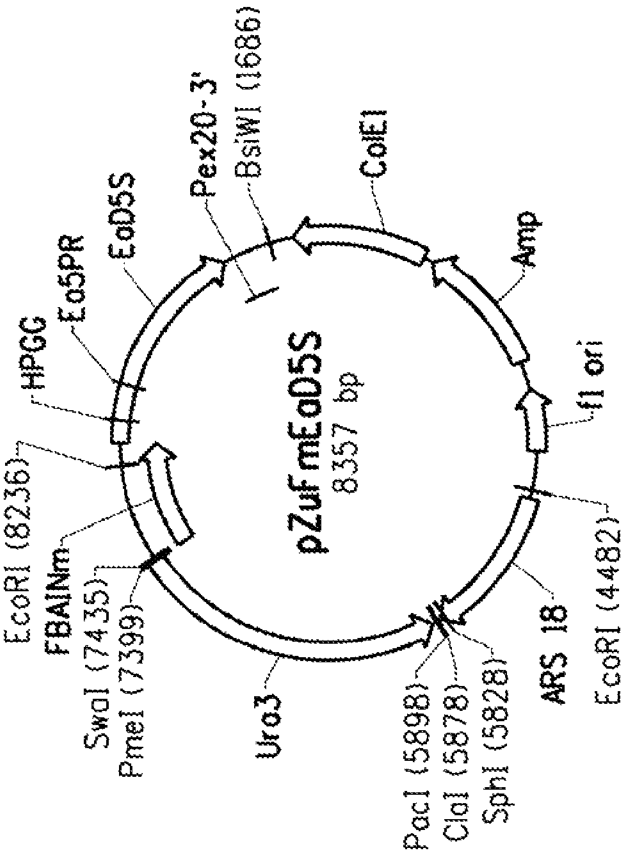
Figure 9A:
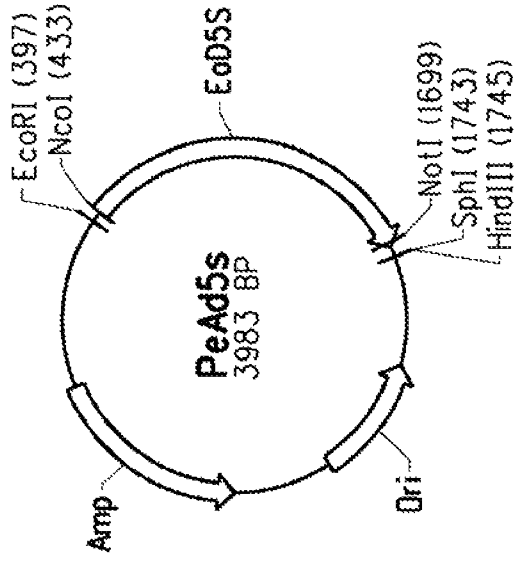

The codon usage of the Δ5 desaturase gene (EaD5Des1) of *Euglena anabaena* was optimized for expression in *Yarrowia lipolytica*, in a manner similar to that described in PCT Publication No. WO 2004/101753 and U.S. Pat. No. 7,125,672. Specifically, a codon-optimized Δ5 desaturase gene (designated "EaD5S", SEQ ID NO:25) was designed based on the coding sequence of EaD5Des1 (SEQ ID NO:12), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 183 bp of the 1362 bp coding region were modified (13.4%) and 174 codons were optimized (38.3%). The GC content was reduced from 57.6% within the wild type gene (i.e., EaD5Des1) to 54.6% within the synthetic gene (i.e., EaD5S). A NcoI site and NotI sites were incorporated around the translation initiation codon and after the stop codon of EaD5S (SEQ ID NO:25), respectively. FIGS. 8A, 8B and 8C show a comparison of the nucleotide sequences of EaD5Des1 (SEQ ID NO:12) and EaD5S (SEQ ID NO:25). The protein sequence encoded by the codon-optimized gene (i.e., SEQ ID NO:26) is identical to that of the wildtype protein sequence (i.e., SEQ ID NO:13). The designed EaD5S gene was synthesized by GenScript Corporation (Piscataway, N.J.) and cloned into pUC57 (GenBank Accession No. Y14837) to generate pEaD5S (SEQ ID NO:27; FIG. 9A).

Example 6

Construction and Functional Analysis of *Yarrowia lipolytica* Expression Vector pZUFmEaD5S, Comprising a Synthetic Δ5 Desaturase Gene (Derived from *Euglena anabaena*), Codon-Optimized for Expression in *Yarrowia lipolytica* (EaD5S)

The present Example describes the functional expression of *Yarrowia lipolytica* vector pZUFmEaD5S, comprising a chimeric FBAINm::EaD5S::Pex20 gene, wherein EaD5S is a synthetic Δ5 desaturase derived from *Euglena anabaena* and codon-optimized for expression in *Yarrowia*. The plasmid pZUFmEaD5S (FIG. 9B) contained the following components:

TABLE 11

Components Of Plasmid pZUFmEaD5S (SEQ ID NO: 44)

| RE Sites And Nucleotides Within SEQ ID NO: 44 | Description Of Fragment And Chimeric Gene Components |
|---|---|
| Swa I/BsiW I (7435-1686) | FBAINm::EaD5S::Pex20, comprising:<br>FBAINm: *Yarrowia lipolytica* FBAIN promoter (U.S. Pat. No. 7,202,356);<br>EaD5S: codon-optimized Δ5 desaturase (SEQ ID NO: 25), derived from *Euglena anabaena*;<br>Pex20: Pex20 terminator sequence of *Yarrowia* Pex20 gene (GenBank Accession No. AF054613) |
| 2722-1842 | ColE1 plasmid origin of replication |
| 3652-2792 | Ampicillin-resistance gene ($Amp^R$) for selection in *E. coli* |
| 4551-5855 | *Yarrowia* autonomous replication sequence (ARS18; GenBank Accession No. A17608) |
| 7399-5898 | Yarrowia Ura 3 gene (GenBank Accession No. AJ306421) |

Functional Analysis of *Yarrowia lipolytica* Transformants Comprising pZUFmEaD5S Plasmid pZUFmEaD5S (SEQ ID NO:44; FIG. 9B) was transformed into strain Y4036U as described in the General Methods. The transformants were selected on MMLeu plates. After 2 days growth at 30° C., transformants were picked and re-streaked onto fresh MM plates. Once grown, these strains were individually inoculated into 3 mL liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 2.2% ARA and 7.4% DGLA of total lipids produced in all 8 transformants, wherein the conversion efficiency of DGLA to ARA in these 8 strains was determined to be about 22.9%. Thus, this experimental data demonstrated that the synthetic *Euglena anabaeana* Δ5 desaturase codon-optimized for expression in *Yarrowia lipolytica* (EaD5S, as set forth in SEQ ID NO:25) can efficiently desaturate DGLA to ARA.

What is claimed is:

1. A microbial host cell comprising an isolated polynucleotide comprising:

(a) a nucleotide sequence encoding a polypeptide having Δ5 desaturase activity, wherein the polypeptide has at least 90% amino acid identity, based on the Clustal V method of alignment provided by the MegAlign™ program of the DNASTAR LASERGENE bioinformatics computing suite (default parameters: KTUPLE=1, GAP PENALTY=3, WINDOW=5 and DIAGONALS SAVED=5), when compared to an amino acid sequence as set forth in SEQ ID NO:13;

(b) a nucleotide sequence encoding a polypeptide having Δ5 desaturase activity, wherein the nucleotide sequence has at least 90% sequence identity, based on the Basic Local Alignment Search Tool ["BLASTN"] method of alignment provided by the National Center for Biotechnology Information (default parameters: short queries=automatically adjust parameters for short input sequences, expect threshold=10, word size=11, match/mis-match scores=2, −3, gap costs=(existence: 5, extension: 2), and filter=low complexity regions), when compared to a nucleotide sequence as set forth in SEQ ID NO:12 or SEQ ID NO:25;

(c) a nucleotide sequence encoding a polypeptide having Δ5 desaturase activity, wherein the nucleotide sequence hybridizes under stringent conditions to a nucleotide sequence as set forth in SEQ ID NO:12 or SEQ ID NO:25, wherein said stringent conditions include hybridization in 50% formamide, 1 M NaCl, 1% SDS at 37° C. and a wash in 0.1×SSC at 60° C. to 65° C.; or, (d) a complement of the nucleotide sequence of (a), (b) or (c), wherein the complement and the nucleotide sequence consist of the same number of nucleotides and are 100% complementary.

2. The microbial host cell of claim 1 wherein the isolated polynucleotide encodes an amino acid sequence as set forth in SEQ ID NO:13.

3. The microbial host cell of claim 1 wherein the microbial host cell is selected from the group consisting of yeast, algae, bacteria, euglenoids, stramenopiles and fungi.

4. The microbial host cell of claim 3 wherein the cell is a fungus of the genus *Mortierella*.

5. The microbial host cell of claim 3 wherein the cell is a stramenopiles from the group consisting of: *Thraustochytrium* and *Schizochytrium*.

6. The microbial host cell of claim 3 wherein the yeast is an oleaginous yeast.

7. The microbial host cell of claim 6 wherein the oleaginous yeast is selected from the group consisting of: *Yarrowia, Candida, Rhodotorula, Rhodosporidium, Cryptococcus, Trichosporon* and *Lipomyces*.

8. A method for the production of arachidonic acid comprising:

a) providing a microbial host cell comprising:

(i) a recombinant nucleotide molecule encoding a Δ5 desaturase polypeptide having at least 90% amino acid identity when compared to a polypeptide having the amino acid sequence as set forth in SEQ ID NO:13, based on the Clustal V method of alignment provided by the MegAlign™ program of the DNASTAR LASERGENE bioinformatics computing suite (default parameters: KTUPLE=1, GAP PENALTY=3, WINDOW=5 and DIAGONALS SAVED=5); and, (ii) a source of dihomo-γ-linolenic acid;

b) growing the microbial host cell of step (a) under conditions wherein the recombinant nucleic acid molecule encoding the Δ5 desaturase polypeptide is expressed and the dihomo-γ-linolenic acid is converted to arachidonic acid; and, c) optionally recovering the arachidonic acid of step (b).

9. A method for the production of eicosapentaenoic acid comprising:

a) providing a microbial host cell comprising:

(i) a recombinant nucleotide molecule encoding a Δ5 desaturase polypeptide having at least 90% amino acid identity when compared to a polypeptide having the amino acid sequence as set forth in SEQ ID NO:13, based on the Clustal V method of alignment provided by the MegAlign™ program of the DNASTAR LASERGENE bioinformatics computing suite (default parameters: KTUPLE=1, GAP PENALTY=3, WINDOW=5 and DIAGONALS SAVED=5); and, (ii) a source of eicosatetraenoic acid;

b) growing the microbial host cell of step (a) under conditions wherein the recombinant nucleic acid molecule encoding the Δ5 desaturase polypeptide is expressed and the eicosatetraenoic acid is converted to eicosapentaenoic acid; and, c) optionally recovering the eicosapentaenoic acid of step (b).

10. The method of either of claim 8 or 9 wherein the microbial host cell is a *Yarrowia*, comprising a recombinant nucleotide molecule encoding a Δ5 desaturase polypeptide as set forth in SEQ ID NO:25 wherein the recombinant nucleotide molecule comprises at least 174 codons which are optimized for expression in *Yarrowia*.

11. A method according to either of claim 8 or 9 wherein:

a.) the recombinant nucleic acid molecule has a nucleic acid sequence selected from the group consisting of SEQ ID NO:12 or SEQ ID NO:25; and, b.) the host cell is *Yarrowia lipolytica*.

12. An isolated nucleic acid molecule which encodes a Δ5 desaturase as set forth in SEQ ID NO:25 wherein at least 174 codons are codon-optimized for expression in *Yarrowia*.

* * * * *